US012589124B2

(12) United States Patent
Groeger et al.

(10) Patent No.: US 12,589,124 B2
(45) Date of Patent: Mar. 31, 2026

(54) BIFIDOBACTERIUM LONGUM

(71) Applicant: PRECISIONBIOTICS GROUP LIMITED, Cork (IE)

(72) Inventors: David Groeger, County Cork (IE); Barry Kiely, County Cork (IE)

(73) Assignee: PRECISIONBIOTICS GROUP LIMITED, Cork (IE)

( * ) Notice: Subject to any disclaimer, the term of this patent is extended or adjusted under 35 U.S.C. 154(b) by 566 days.

(21) Appl. No.: 17/910,852

(22) PCT Filed: Mar. 12, 2021

(86) PCT No.: PCT/EP2021/056431
§ 371 (c)(1),
(2) Date: Sep. 12, 2022

(87) PCT Pub. No.: WO2021/180973
PCT Pub. Date: Sep. 16, 2021

(65) Prior Publication Data
US 2023/0106819 A1 Apr. 6, 2023

(30) Foreign Application Priority Data

| Mar. 13, 2020 | (EP) | .................................... | 20163197 |
| Mar. 3, 2021 | (EP) | .................................... | 21160580 |
| Mar. 4, 2021 | (EP) | .................................... | 21160660 |

(51) Int. Cl.

| *A61K 35/745* | (2015.01) |
| *A61K 31/593* | (2006.01) |
| *A61K 45/06* | (2006.01) |
| *A61P 31/14* | (2006.01) |

(52) U.S. Cl.
CPC .......... *A61K 35/745* (2013.01); *A61K 31/593* (2013.01); *A61K 45/06* (2013.01); *A61P 31/14* (2018.01)

(58) Field of Classification Search
None
See application file for complete search history.

(56) References Cited

U.S. PATENT DOCUMENTS

| 4,157,278 | A | 6/1979 | Ross et al. |
| 4,464,362 | A | 8/1984 | Kludas et al. |
| 2005/0100559 | A1* | 5/2005 | Myatt ...................... C12N 1/04 |
| | | | 424/234.1 |
| 2009/0060878 | A1 | 3/2009 | Clymer et al. |
| 2009/0196921 | A1 | 8/2009 | Ebel et al. |
| 2010/0278793 | A1 | 11/2010 | Gueniche et al. |
| 2011/0020284 | A1 | 1/2011 | Macsharry et al. |
| 2011/0020400 | A1 | 1/2011 | Macsharry et al. |
| 2011/0046084 | A1 | 2/2011 | Grant et al. |
| 2012/0128644 | A1* | 5/2012 | Hillman ................... A61P 31/12 |
| | | | 424/93.4 |
| 2012/0201798 | A1 | 8/2012 | Kekkonen et al. |
| 2012/0230956 | A1 | 9/2012 | Mclean et al. |
| 2012/0276143 | A1 | 11/2012 | O'Mahony et al. |
| 2013/0165470 | A1 | 6/2013 | Isfort |
| 2013/0180524 | A1 | 7/2013 | Shahaf et al. |
| 2013/0224253 | A1 | 8/2013 | Petit et al. |
| 2015/0044188 | A1 | 2/2015 | Griffiths |
| 2016/0106937 | A1 | 4/2016 | Shahaf et al. |
| 2016/0250265 | A1 | 9/2016 | Petit et al. |
| 2017/0128678 | A1 | 5/2017 | Shahaf et al. |
| 2018/0177834 | A1 | 6/2018 | Griffiths |

FOREIGN PATENT DOCUMENTS

| AU | 2010288546 B2 | 8/2015 |
| CN | 1433811 A | 8/2003 |
| CN | 102321187 A | 1/2012 |
| EP | 2181703 A1 | 5/2010 |
| EP | 2455092 A1 | 5/2012 |
| JP | 2005508617 A | 4/2005 |
| JP | 2007169200 A | 7/2007 |
| JP | 2010522552 A | 7/2010 |
| JP | 2010522553 A | 7/2010 |
| JP | 2013507431 A | 3/2013 |
| JP | 2017081853 A | 5/2017 |
| RU | 2151606 C1 | 6/2000 |
| RU | 2216588 C1 | 1/2004 |
| RU | 2314341 C1 | 1/2008 |
| RU | 2557310 C2 | 12/2013 |
| WO | 2008053444 A2 | 5/2008 |
| WO | 2008053444 A3 | 5/2008 |
| WO | WO-2009100331 A2 * | 8/2009 ............. A61K 35/74 |
| WO | 2012029064 A1 | 3/2012 |

(Continued)

OTHER PUBLICATIONS

Xu et al., "Pathological Findings of COVID-19 Associated with Acute Respiratory Distress Syndrome", Lancet Respir Med. Feb. 18, 2020. pii: S2213-2600(20)30076-X.

Leth-Larsen et al., "The SARS Coronavirus Spike Glycoprotein is Selectively Recognized by Lung Surfactant Protein D and Activates Macrophages", Immunobiology. 2007;212(3):201-11. Epub Jan. 26, 2007.

Xu et al., "Management of COVID-19: the Zhejiang experience", Zhejiang Da Xue Xue Bao Yi Xue Ban. Feb. 21, 2020;49(2):147-57, DOI: 10.3785/j.issn.1008-9292.2020.02.02. PMID: 32391658; PMCID: PMC8800711.

Channappanavar et al., "Dysregulated Type I Interferon and Inflammatory Monocyte-Macrophage Responses Cause Lethal Pneumonia in SARS-COV-Infected Mice", Cell Host Microbe. Feb. 10, 2016;19(2):181-93.

(Continued)

*Primary Examiner* — Oluwatosin A Ogunbiyi
(74) *Attorney, Agent, or Firm* — Bookoff McAndrews, PLLC

(57) ABSTRACT

*Bifidobacterium longum* strains and cell wall fractions isolated from *Bifidobacterium longum* strains are useful in the prophylaxis or treatment of an infection in a subject caused by a coronavirus such as SARS-CoV-2. They are also useful in the prophylaxis of a secondary bacterial infection associated with an infection in a subject caused by a coronavirus, especially a subject who is susceptible to respiratory infections.

12 Claims, 56 Drawing Sheets
Specification includes a Sequence Listing.

(56) References Cited

FOREIGN PATENT DOCUMENTS

| WO | 2012062780 A1 | 5/2012 |
| WO | 2015021530 A1 | 2/2015 |
| WO | 2015140299 A1 | 9/2015 |
| WO | 2016009377 A1 | 1/2016 |
| WO | 2016120320 A1 | 8/2016 |
| WO | 2016142767 A1 | 9/2016 |
| WO | 2017032897 A1 | 3/2017 |
| WO | 2018047106 A1 | 3/2018 |
| WO | 2018158306 A1 | 9/2018 |
| WO | 2018158306 A8 | 9/2018 |
| WO | 2018158309 A1 | 9/2018 |
| WO | 2018168449 A2 | 9/2018 |
| WO | WO-2021168577 A1 * | 9/2021 ............. A61K 39/00 |

OTHER PUBLICATIONS

Channappanavar et al., "IFN-I Response Timing Relative to Virus Replication Determines MERS Coronavirus Infection Outcomes", J Clin Invest. Jul. 29, 2019;130:3625-39.

Ding et al., "The Clinical Pathology of Severe Acute Respiratory Syndrome (SARS): a Report from China", J Pathol 2003; 200: 282-89.

Ng et al., "Clinicopathologic, Immunohistochemical, and Ultrastructural Findings of a Fatal case of Middle East Respiratory Syndrome Coronavirus Infection in the United Arab Emirates", Apr. 2014. Am J Pathol 2016; 186: 652-58.

Thevarajan et al., "Breadth of Concomitant Immune Responses Underpinning Viral Clearance and Patient Recovery in a Non-Severe Case of COVID-19", medRxiv 2020.02.20.20025841; doi: https://doi.org/10.1101/2020.02.20.20025841.

Song et al., "From SARS to MERS", Thrusting Coronaviruses into the Spotlight, Jan. 2019; 11(1): 59.

Scheuplein et al., "High Secretion of Interferons by Human Plasmacytoid Dendritic Cells Upon Recognition of Middle East Respiratory Syndrome Coronavirus", J Virol. Apr. 2015;89(7):3859-69. doi: 10.1128/JVI.03607-14.

Zhao et al., "Identification of Residues Controlling Restriction versus Enhancing Activities of IFITM Proteins on Entry of Human Coronaviruses", J Virol. Feb. 26, 2018;92(6). pii: e01535-17. doi: 10.1128/JVI.01535-17. Print Mar. 15, 2018.

Channappanavar et al., "Pathogenic Human Coronavirus Infections: Causes and Consequences of Cytokine Storm and Immunopathology", Semin Immunopathol (2017) 39:529-539, DOI: 10.1007/s00281-017-06290x.

Liao et al., "The Landscape of Lung Bronchoalveolar Immune Cells in COVID-19 Revealed by Single-cell RNA Sequencing", Institute for Hepatology, National Clinical Research Center for Infectious Disease, China, MedRXIV, Feb. 2020.

Liu et al., "Overlapping and Discrete Aspects of the Pathology and Pathogenesis of the Emerging Human Pathogenic Coronaviruses SARS-CoV, MERS-CoV, and 2019-nCoV", J Med Virol. Feb. 13, 2020.

Blanco-Melo et al., "Imbalanced Host Response to SARS-CoV-2 Drives Development of COVID-19" Cell. Epub May 15, 2020. PMID: 32416070; PMCID: PMC7227586. May 28, 2020;181(5):1036-1045.e9. DOI: 10.1016/j.cell.2020.04.026.

Zhou et al., "Heightened Innate Immune Responses in the Respiratory Tract of COVID-19 patients", Cell Host Microbe 27, 883-890 (2020).

Wilk et al., "A Single-Cell Atlas of the Peripheral Immune Response in Patients with Severe COVID-19", Nat. Med. 26, 1070-1076 (2020).

Lee et al., "Immunophenotyping of COVID-19 and Influenza Highlights the Role of Type I Interferons in Development of Severe COVID-19", Sci. Immunol. 5 (2020).

Lucas et al., "Longitudinal Analyses Reveal Immunological Misfiring in Severe COVID-19", Nature Journal, Jul. 27, 2020, https://doi.org/10.1038/s41586-020-2588-y.

Park et al., "Type I Interferons and the Cytokine TNF Cooperatively Reprogram the Macrophage Epigenome to Promote Inflammatory Activation", Nat. Immunol. 18, 1104-1116 (2017).

Wang et al., Retrospective Multicenter Cohort Study Shows Early Interferon Therapy is Associated with Favorable Clinical Responses in COVID-19 Patients. Cell Host Microbe https://doi.org/10.1016/j.chom.2020.07.005 (2020).

Dinnon III et al., "A Mouse-Adapted Model of SARS-CoV-2 to Test COVID-19 Countermeasures." Nature Journal. 2020; 586: 560-566.

Vanderheiden et al., "Type I and Type III Interferons Restrict SARS-CoV-2 Infection of Human Airway Epithelial Cultures.", J Virol. 2020; 94: e00985-e001020.

Feld et al., "Peginterferon Lambda for the Treatment of Outpatients with COVID-19: a Phase 2, Placebo-Controlled Randomised Trial", Lancet Respir Med, (2021).

Busnadiego et al., "Antiviral Activity of Type I, II, and III Interferons Counterbalances ACE2 Inducibility and Restricts SARS-CoV-2", mBio 11, (2020).

Stanifer et al., "Critical Role of Type III Interferon in Controlling SARS-CoV-2Infection in Human Intestinal Epithelial Cells", Cell Rep 32, 107863 (2020).

Galani et al., "Untuned Antiviral Immunity in COVID-19 Revealed by Temporal Type I/III Interferon Patterns and Flu Comparison", Nat Immunol 22, 32-40 (2021).

Felgenhauer et al., "Inhibition of SARS-CoV-2 by Type I and Type III Interferons", J Biol Chem 295, 13958-13964 (2020).

O'Brien et al., "Weak Induction of Interferon Expression by Severe Acute Respiratory Syndrome Coronavirus 2 Supports Clinical Trials of Interferon-lambda to Treat Early Coronavirus Disease 2019", Clinical Infectious Diseases, 71, 1410-1412 (2020).

Kerget et al., "Are Serum Interleukin 6 and Surfactant Protein D Levels Associated with the Clinical Course of COVID-19?", Lung. 2020;198(5):777-784. doi:10.1007/s00408-020-00393-8.

Watson et al., "Dual Functioning Immune Molecules With Antiviral and Immunomodulatory Properties", Front Immunol. Jan. 19, 2021;11:622598. doi: 10.3389/fimmu.2020.622598.

Dijkman et al., "Effective Interferon Lambda Treatment Regimen to Control Lethal MERS-CoV Infection in Mice." J Virol. Jun. 8, 2022;96(11):e0036422. doi: 10.1128/jvi.00364-22. Epub May 19, 2022. PMID: 35588276; PMCID: PMC9175626.

Sullivan et al., "The Microbiome and the Pathophysiology of Asthma", Respir Res 17, 163 (2016). https://doi.org/10.1186/s12931-016-0479-4.

International Search Report for PCT Application PCT/EP2021056431, Apr. 23, 2021, 6 pages.

Almond M. H., et al. "Obesity and Susceptibility to Severe Outcomes Following Respiratory Viral Infection", Thorax. Jul. 2013, 68 (7); pp. 684-686. doi: 10.1136/thoraxjnl-2012-203009.

Allen, AP, et al., "Bifidobacterium longum 1714 as a Translational Psychobiotic: Modulation of Stress, Electrophysiology and Neurocognition in Healthy Volunteers", Translational Psychiatry, 2016, vol. 6, pp. 1-6.

Amrouche T., et al., "Effects of Bifidobacterial Cytoplasm, Cell Wall and Exopolysaccharide on Mouse Lymphocyte Proliferation and Cytokine Production", International Dairy Journal, 2006, 16; pp. 70-80.

Bartlett N. W., et al., "Mouse Models of Rhinovirus Infection and Airways Disease", Methods in Molecular Biology., 2015;1221, pp. 181-188. doi: 10.1007/978-1-4939-1571-2_14.

Bouhnik Y., "Survie et Effets Chez L'homme des Bactéries Ingérées Dans Les Laits Fermentés", Lait 1993, 73, pp. 241-247.

Chasset, F., et al., Type I Interferons in Systems Autoimmune Diseases: Distinguishing Between Afferent and Efferent Functions for Precision Medicine and Individualized Treatment, Frontiers in Pharmacology, 2021, vol. 1, pp. 1-18.

Cole, S. L., et al., "Contribution of Innate Immune Cells to Pathogenesis of Severe Influenza Virus Infection", Clinical Science, 2017, vol. 131, 269-83.

Davidson S., et al., "Pathogenic Potential of Interferon $\alpha\beta$ in Acute Influenza Infection", Nature Communications, May 21, 2014; 5:3864, pp. 1-15.

(56)                References Cited

OTHER PUBLICATIONS

Davidson S., et al., "IFNλ Is a Potent Anti-Influenza Therapeutic Without The Inflammatory Side Effects of IFNα treatment", EMBO Molecular Medicine., Sep. 1, 2016;8(9):pp. 1099-1112.

Davidson, S.A., "Unique and Overlapping Actions of Type I and III IFNs in Influenza A Virus Infection and Implications for Therapy", 2016, The Open University.

Dunning, J., et al., "Seasonal and Pandemic Influenza: 100 Year of Progress, Still Much to Learn", Mucosal Immunology, 2020, vol. 13, pp. 566-573.

Durbin R. K., et al, "Interferon Induction and Function at the Muscol Surface", Immunol Rev. Sep. 2013; 255 (1): pp. 25-39.

Galani I.E., et al, "Interferon-λ Mediates Non-Redundant Front-Line Antiviral Protection Against Influenza Virus Infection Without Compromising Host Fitness", Immunity, May 16, 2017; 46(5): pp. 875-890.

Groeger D., et al., "Bifidobacterium infantis 35624 Modulates Host Inflammatory Processes Beyond The Gut", Gut Microbes, Jul.-Aug. 2013; 4(4): pp. 325-339. doi: 10.4161/gmic.25487.

Hartshorn K.L., et al., "Mechanisms of Anti-influenza Activity of Surfactant Proteins A and D: Comparison With Serum Collectins", American Journal of Physiological Society, 1997; 273: L1156-L1166.

Hartshorn K.L., et al., "Mechanism of Binding of Surfactant Protein D to Influenza A Viruses: Importance of Binding to Haemagglutinin to Antiviral Activity", Biochem J 2000; 351 (Pt 2): pp. 449-458.

Hawgood S. et al., "Pulmonary Collectins Modulate Strain-Specific Influenza A Virus Infection and Host Responses", Journal of Virology, 2004; 78: pp. 8565-8572.

Hewitt R., et al., "The Role of Viral Infections in Exacerbations of Chronic Obstructive Pulmonary Disease and Asthma", Therapeutic Advances in Respiratory Disease, Apr. 2016;10(2): pp. 158-174. doi: 10.1177/1753465815618113.

Holvoet, S., et al., "Characterization of Candidate Anti-Allergic Probiotic Strains in a Model of Th2-Skewed Human Peripheral Blood Mononuclear Cells", Int Arch Allergy Immunol, 2013, vol. 161, pp. 142-154.

Homayouni A. R., et al., "Can Probiotics Prevent or Improve Common Cold and Influenza?", Nutrition 2019, 29; pp. 805-806.

Ichikawa A., et al., "CXCL10-CXCR3 Enhances the Development of Neutrophil-Mediated Fulminant Lung Injury of Viral and Nonviral Origin", American Journal of Respiratory and Critical Care Medicine, Jan. 1, 2013;187(1): pp. 65-77.

Ivashkiv L. B., et al., "Regulation of Type I Interferon Responses", Nat Rev Immunol, Jan. 2014; 14(1): pp. 36-49.

Iwabuchi, N., et al., "Effects of Intranasal Administration of Bifidobacterium longum BB536 on Mucosal Immune System in Respiratory Tract and Influenza Virus Infection in Mice", Milk Science ,2009, vol. 58, No. 3; pp. 129-133.

Iwabuchi, N., et al., "Immuno-modulating effects of Bifidobacterium longum BB536 and the mechanisms", Milk Science, 2010, vol. 59, No. 3; pp. 275-281.

Iwabuchi N., et al., "Oral Administration of Bifidobacterium longum Ameliorates Influenza Virus Infection in Mice", Biol. Pharm. Bull , 2011. 34(8) pp. 1352-1355.

Iwabuchi, N., et al., "Suppressive Effects of Bifidobacterium longum on the Production of Th2-attracting Chemokines Induced with T Cell-Antigen-Presenting Cell Interactions", FEMS Immunol Med Microbiol, 2009, vol. 55, pp. 324-334.

Jartti T., et al., "Role of Viral Infections in the Development and Exacerbation of Asthma in Children", J Allergy Clin Immunol. Oct. 2017;140(4): pp. 895-906.

Jounblat R., et al., "The Role of Surfactant Protein D in the Colonisation of the Respiratory Tract and Onset of Bacteraemia During Pneumococcal Pneumonia", Respiratory Research, Oct. 28, 2005;6:126, pp. 1-12.

Kawahara T., et al., "Consecutive Oral Administration of Bifidobacterium longum MM-2 Improves the Defense System Against Influenza Virus Infection by Enhancing Natural Killer Cell Activity in a Murine Model", Microbiology and Immunology, 2015: 59: pp. 1-12.

Konieczna P., et al., "Bifidobacterium linfantis 35624 Administration Includes Foxp3 T Regulatory Cells in Human Peripheral Blood: Potential Role for Myeloid and Plasmacytoid Dendritic Cells", Gut Microbiota, Mar. 2012;61(3): pp. 354-366. doi: 10.1136/gutjnl-2011-300936.

Lazear H. M., et al., "Interferon-λ Immune Functions at Barrier Surfaces and Beyond", Immunity, Jul. 21, 2015;43(1): pp. 15-28.

Lei, W., et al., "Effect of Probiotics and Prebiotics on Immune Response to Influenza Vaccination in Adults: a Systematic Review and Meta-Analysis of Randomized Controlled Trials", Nutrients, 2017, 9, 1175, pp. 1-17.

Levine A. M., et al., "Surfactant Protein D Enhances Clearance of Influenza A Virus From the Lung in In Vivo Mouse Models", The Journal of Immunology, 2001; 167: pp. 5868-5873.

Levine A. M., et al., "Surfactant Protein-D Enhances Phagocytosis and Pulmonary Clearance of Respiratory Syncytial Virus", American Journal of Respiratory Cell and Molecular Biology, Aug. 2004;31(2): pp. 193-199.

Li W., et al., "Type I Interferon Induction During Influenza Virus Infection Increases Susceptibility to Secondary Streptococcus pneumoniae Infection by Negative Regulation of Gammadelta T Cells", Journal of Virology, 2012; 86: pp. 12304-12312.

Lopez, P. et al., "Distinct Bifidobacerium Strains Drive Different Immune Responses In Vitro," International Journal of Food Microbiology, 138, pp. 157-165 (2010).

Medina, M. et al., "Differential Immunomodulatory Properties of Bifidobacterium logum Strains: Relevance to Probiotic Selection and Clinical Applications," Clinical and Experimental Immunology, vol. 150, pp. 531-538 (2007).

Mendoza J. L.et al., "The IFN-λ-IFN-λR1-IL-10Rβ Complex Reveals Structural Features Underlying Type III IFN Functional Plasticity", Immunity, Mar. 21, 2017;46(3): pp. 379-392.

Molenkamp G.C., et al., "Effects of Antibiotics on Metabolism of Peptidoglycan, Protein, and Lipids in Bifidobacterium bifidum subsp. pennsulvanicus", Antimicrobial Agents and Chemotherapy, vol. 10, No. 5, (Nov. 1, 1976), pp. 786-794, XP55461829.

Monticelli, L.A., et al., "Innate Lymphoid Cells Promote Lung-Tissue Homeostasis After Infection with Influenza Virus", Nature Immunology, 2011, vol. 12, No. 11, pp. 1045-1056.

Nakamura S. et al., "Synergistic Stimulation of Type I Interferons During Influenza Virus Coinfection Promotes Streptococcus pneumoniae Colonization in Mice", The Journal of Clinical Investigation 2011;121: pp. 3657-3665.

Namba K., et al. "Effects of Bifidobacterium longum BB536 Administration of Influenza Infection, Influenza Vaccine Antibody Titer, and Cell-Mediated Immunity in the Elderly", Biosci. Biotechnol. Biochem 2010. 74, pp. 939-945.

O'Mahony C., et al., "Commensal-Induced Regulatory T Cells Mediate Protection Against Pathogen-Stimulated NF-kB Activation", PLOS Pathogens, Aug. 2008, vol. 4, Issue 8, pp. 1-10.

O'Mahony L., et al., "Lactobacillus and Bifidobacterium in Irritable Bowel Syndrome: Symptom Responses and Relationship to Cytokine Profiles", Gastroenterology. Mar. 2005;128(3): pp. 541-551.

Pegram, H.J., et al. "Activating and Inhibitory Receptors of Natural Killer Cells", Immunology and Cell Biology, 2011, vol. 89, 216-24.

Reading P.C., et al., "Collectin-Mediated Antiviral Host Defense of the Lung: Evidence From Influenza Virus Infection of Mice", Journal of Virology, Nov. 1997;71: pp. 8204-8212.

Rich H., et al., "The Role of Interferon Lambda During Influenza, Staphylococcus aureus Super-Infection", The Journal of Immunology, May 1, 2017, 198(1 Supplement) 77.16.

Sastry K., et al., "Collectins: Pattern Recognition Molecules Involved in First Line Host Defense", Current Opinion in Immunology, 5: pp. 59-66.

Schiavi E., et al., "The Surface-Associated Exopolysaccharide of Bifidobacterium longum 35624 Plays an Essential Role in Dampening Host Proinflammatory Responses and Repressing Local TH17 Responses", Applied and Environmental Microbiology, vol. 82, No. 24, Dec. 15, 2016; pp. 7185-7196.

(56)                    References Cited

OTHER PUBLICATIONS

Sekine K., et al., "A New Morphologically Characterized Cell Wall Preparation (Whole Peptidoglycan) From Bifidobacterium infantis With a Higher Efficacy on the Regression of an Established Tumor in Mice", Cancer Research, AACR—American Association for Cancer Research, US, vol. 45, No. 3, Jan. 1, 1985; pp. 1300-1307.
Shahangian A. et al., "Type I IFNs Mediate Development of Postinfluenza Bacterial Pneumonia in Mice", The Journal of Clinical Investigation, 2009;119: pp. 1910-1920.
Shi X., et al., "Inhibition of the Inflammatory Cytokine Tumor Necrosis Factor-Alpha With Etanercept Provides Protection Against Lethal H1N1 Influenza Infection in Mice", Critical Care, 2013; 17(6);R301, pp. 1-9.
Steinke J. W., et al., "Immune Responses in Rhinovirus-Induced Asthma Exacerbations", Curr Allergy Asthma Rep. Nov. 2016;16(11):78, pp. 1-14.
Sun, J., "Effector T Cells Control Lung Inflammation During Acute Influenza Virus Infection by Producing IL-10", Nature Medicine, 2009, vol. 15, No. 3, pp. 277-284.
Tecle T., et al., "Inhibition of Influenza Viral Neuraminidase Activity by Collectins", Archives of Virology 2007; 152: pp. 1731-1742.
Thiel S., et al., "Structures and Functions Associated With the Group of Mammalian Lectins Containing Collagen-Like Sequences", FEBS Letter 07262, Jun. 1989, vol. 250, No. 1, pp. 78-84.
Vigerust D.J., et al., "N-Linked Glycosylation Attenuates H3N2 Influenza Viruses", Journal of Virology, 2007; 81: pp. 8593-8600.
Wack A., et al., "Guarding the Frontiers: the Biology of the Type III Interferons", Nature Immunology. Jul. 2015, 16 (8): pp. 802-809.
Wang W., et al., "Monoclonal Antibody Against CXCL-10/IP-10 Ameliorates Influenza A (H1N1) Virus Induced Acute Lung Injury", Cell Research (2013) 23: pp. 577-580.
World Health Organization 2007. "Global Surveillance, Prevention and Control of Chronic Respiratory Diseases, a Comprehensive Approach", (Editors Jean Bousquet and Nikolai Khaltaev), pp. 1-155.

Yang J. W., et al., "Corticosteroids for the Treatment of Human Infection With Influenza Virus: a Systematic Review and Meta-Analysis", Clinical Microbiology and Infection, Oct. 2015; 21(10): pp. 956-963.
Yeh, T., et al., "The Influence of Prebiotic and Probiotic Supplementation on Antibody Titers After Influenza Vaccination: a Systematic Review and Meta-Analysis of Randomized Controlled Trials", Drug Design, Development and Therapy, Jan. 2018:12; pp. 217-230.
Zeleya H., et al., "Respiratory Antiviral Immunity and Immunobiotics: Beneficial Effects on Inflammation-Coagulation Interaction During Influenza Virus Infection", Frontiers In Immunology, Dec. 2016, vol. 7, Article 633.
Zhou X., et al., "Exacerbation of Chronic Obstructive Pulmonary Disease", Cell Biochem Biophys, Nov. 2015; 73(2): pp. 349-355.
International Search Report in PCT/EP2018/054914, dated Apr. 17, 2018 (3 pages).
Mordstein, M. et al., "Lambda interferon renders epithelial cells of the respiratory and gastrointestinal tracts resistant to viral infections", Journal of Virology, vol. 84, Issue 11, pp. 5670-5677, Jun. 2010.
Madan, T. et al., "A Recombinant Fragment of Human Surfactant Protein D Binds Spike Protein and Inhibits Infectivity and Replication of SARS-CoV-2 in Clinical Samples," Am. J. Respir. Cell Mol. Biol., vol. 65, Iss. 1, pp. 41-53 (Jul. 2021).
Phetsouphanh, C. et al., "Immunological dysfunction persists for 8 months following initial mild-to-moderate SARS-CoV-2 infection," Nature Immunology, vol. 23, pp. 210-216 (Feb. 2022).
Sposito, B. et al., "The interferon landscape along the respiratory tract impacts the severity of COVID-19," Cell, vol. 184, pp. 4953-4968 (Sep. 2021).
Talla, A. et al., "Persistent serum protein signatures define an inflammatory subset of long COVID," Nature Communications, vol. 14, pp. 1-16 (Jun. 2023).

* cited by examiner

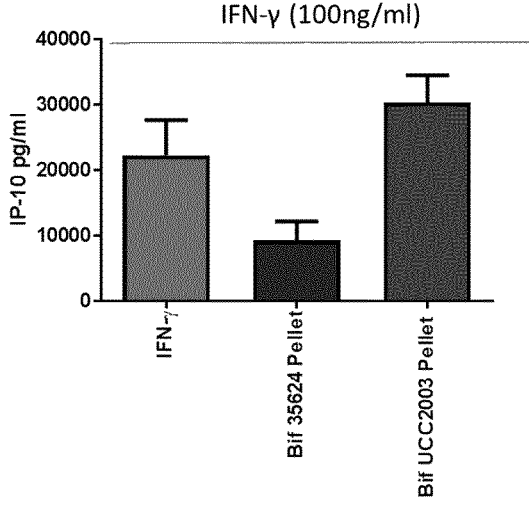
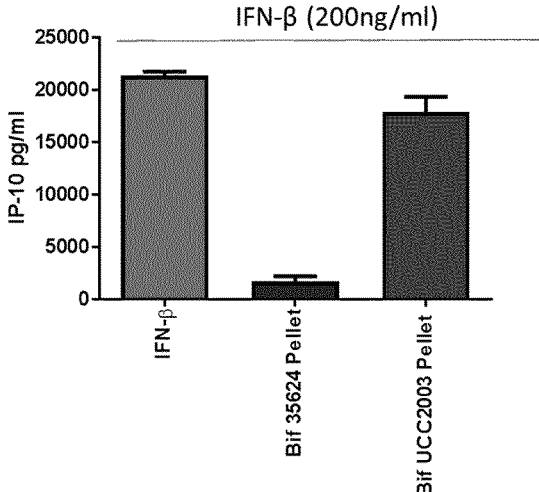
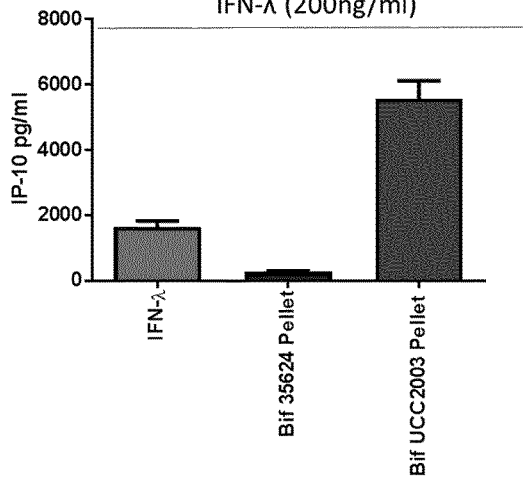
Fig. 6 n=35 animals per group up to day 5 n=15 animals per group

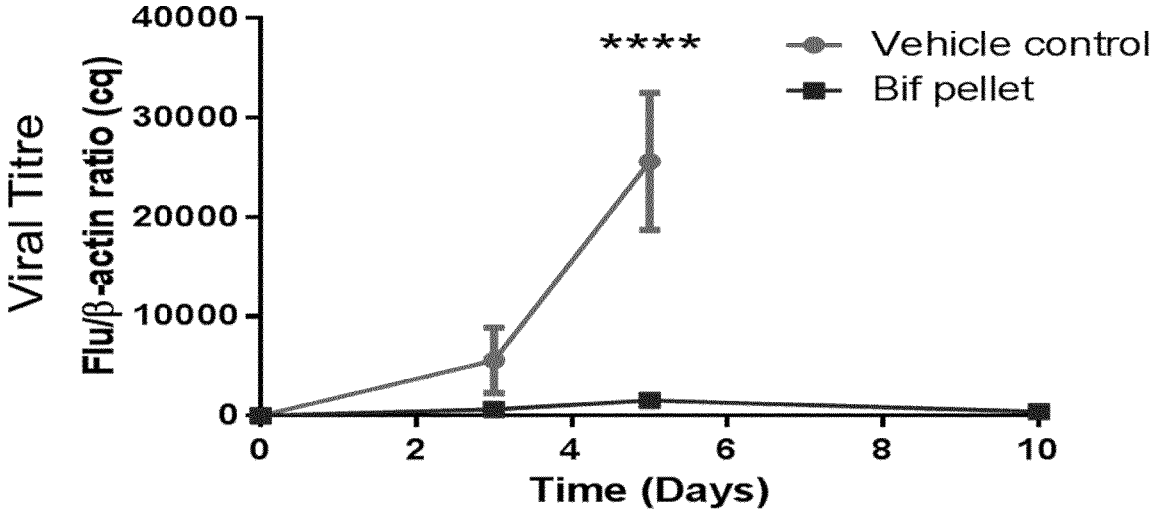
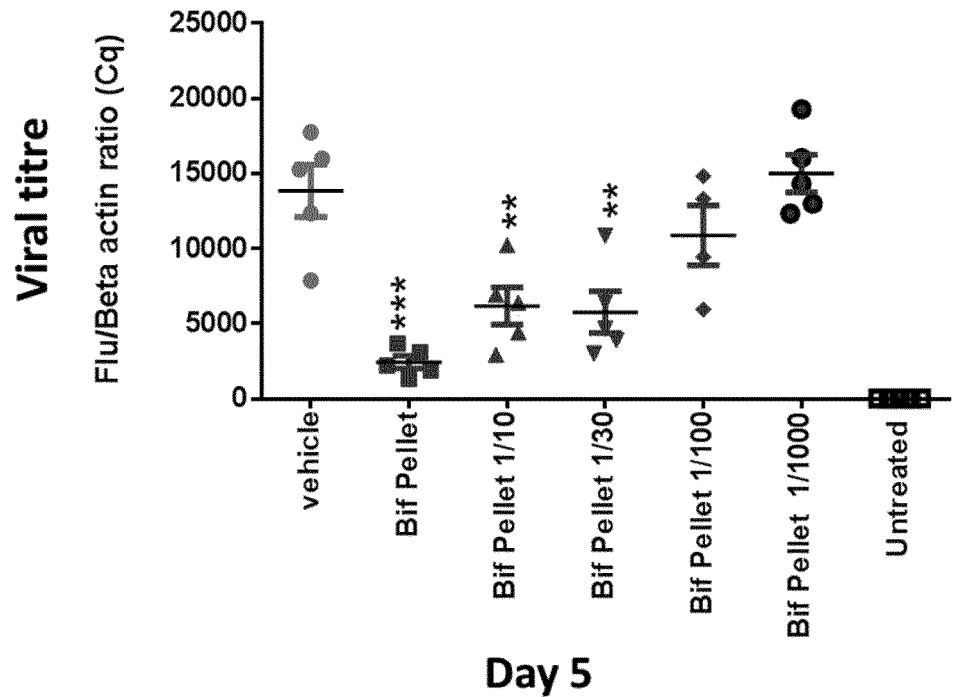
<u>Fig. 10</u>

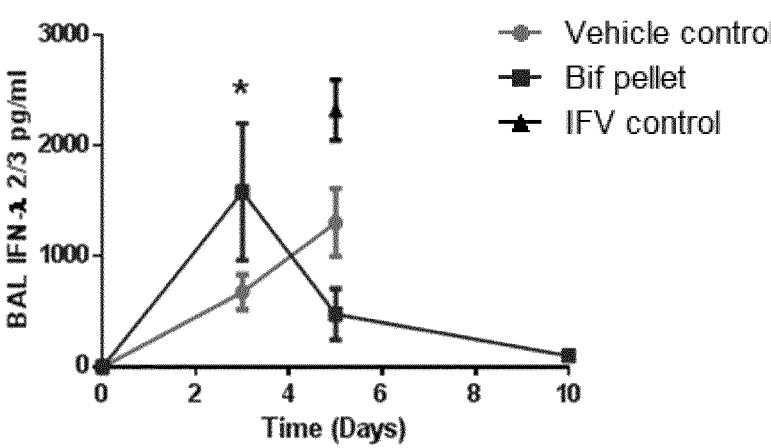
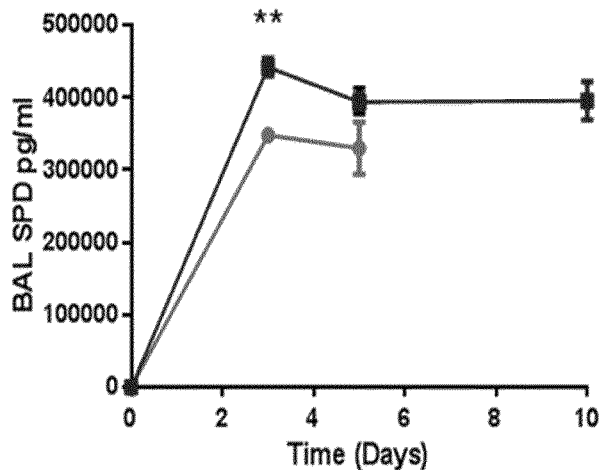
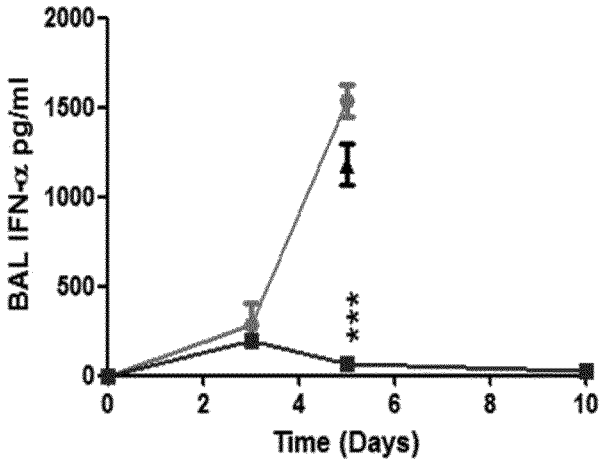
Fig. 11

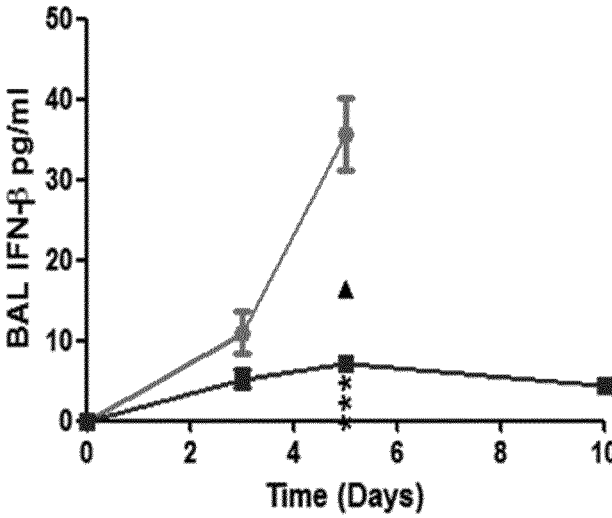
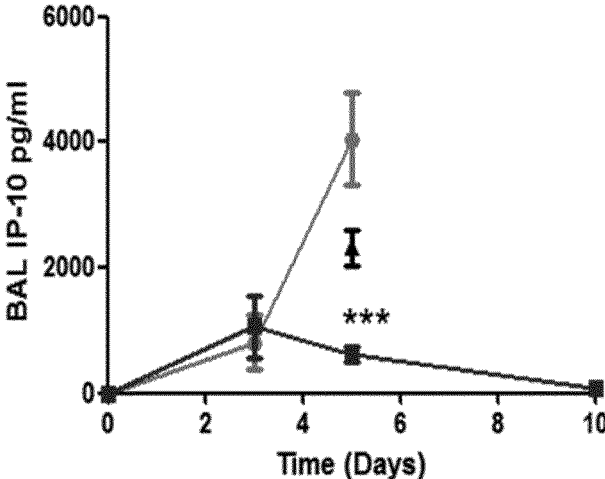
Fig. 11 continued

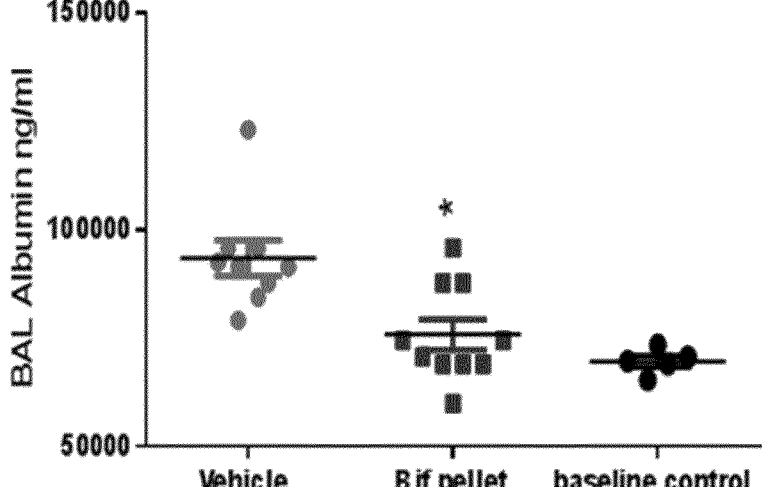
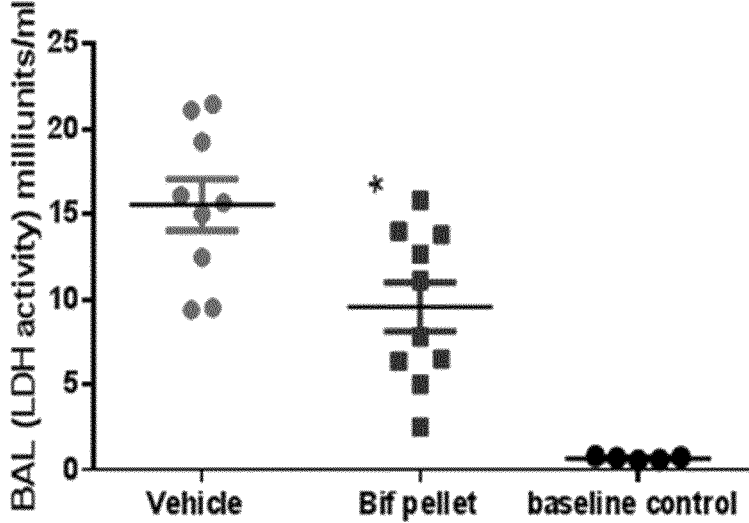
Fig. 13

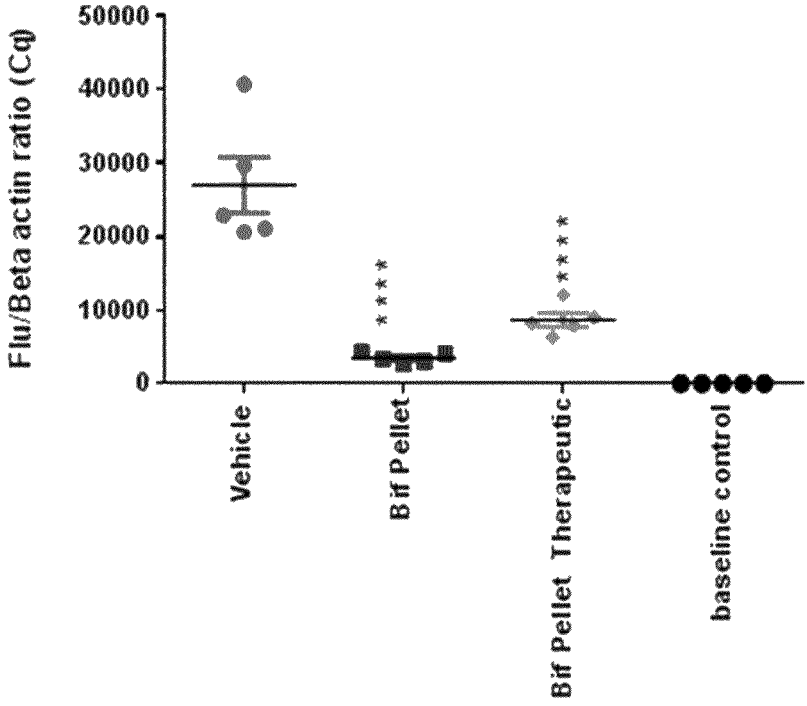
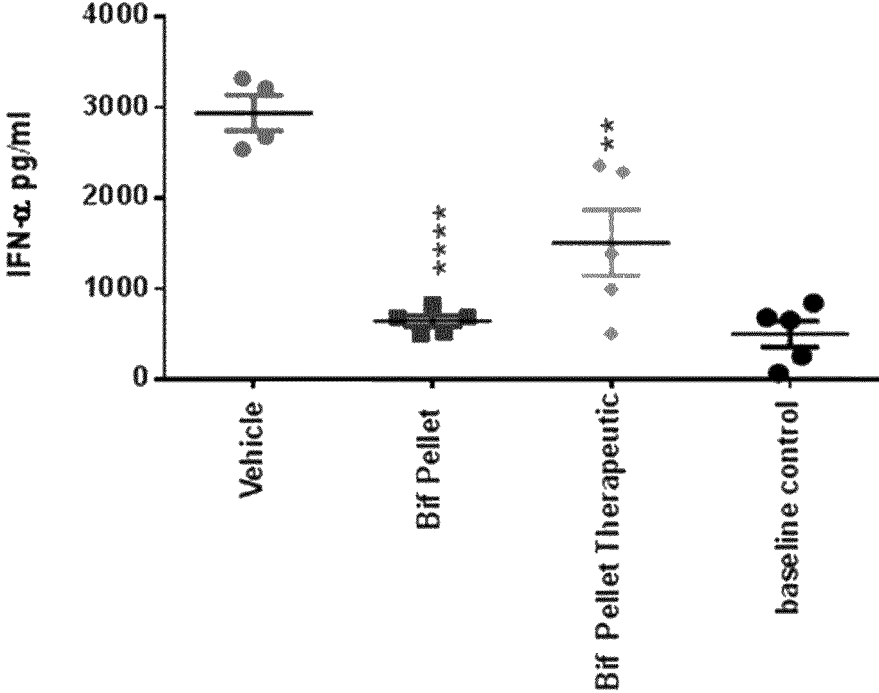
Fig. 15

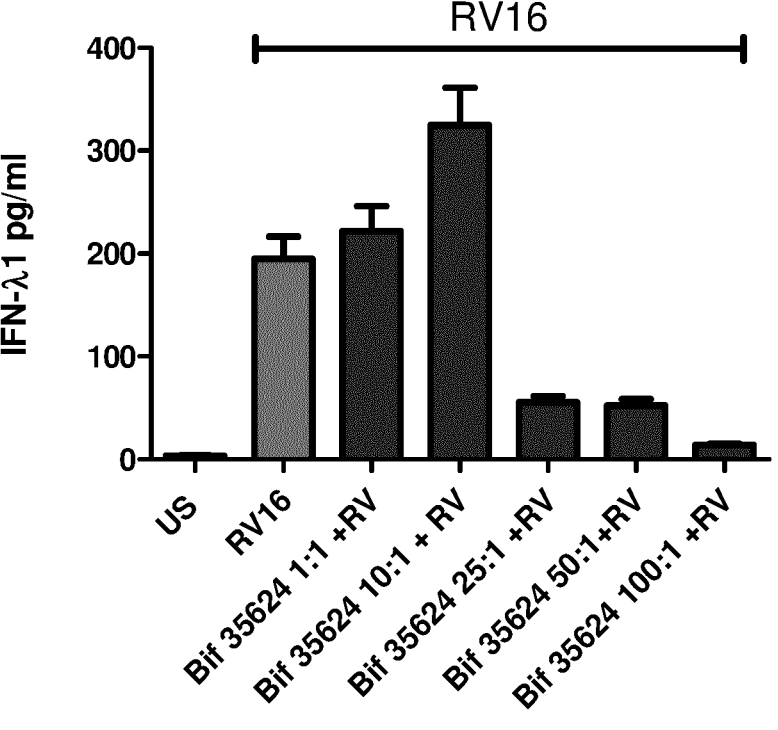
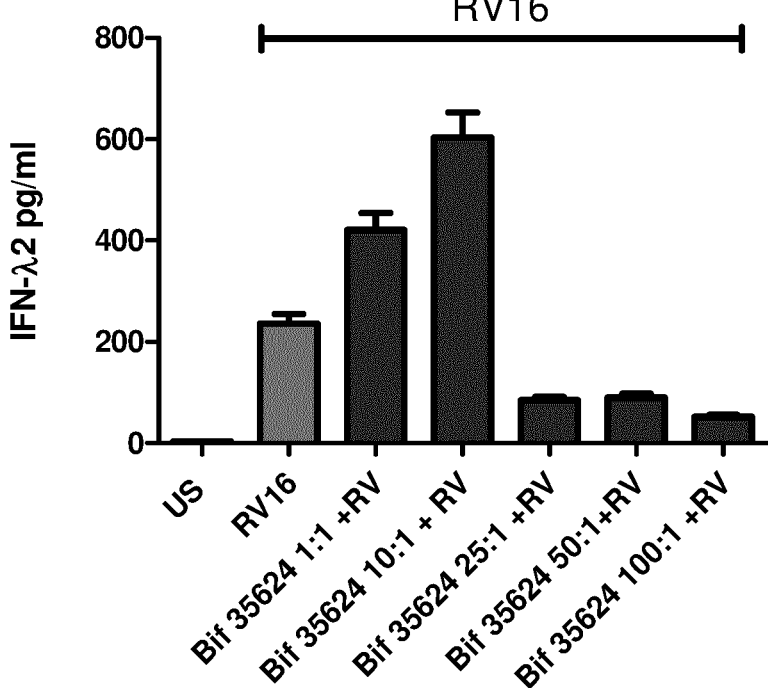
Fig. 18

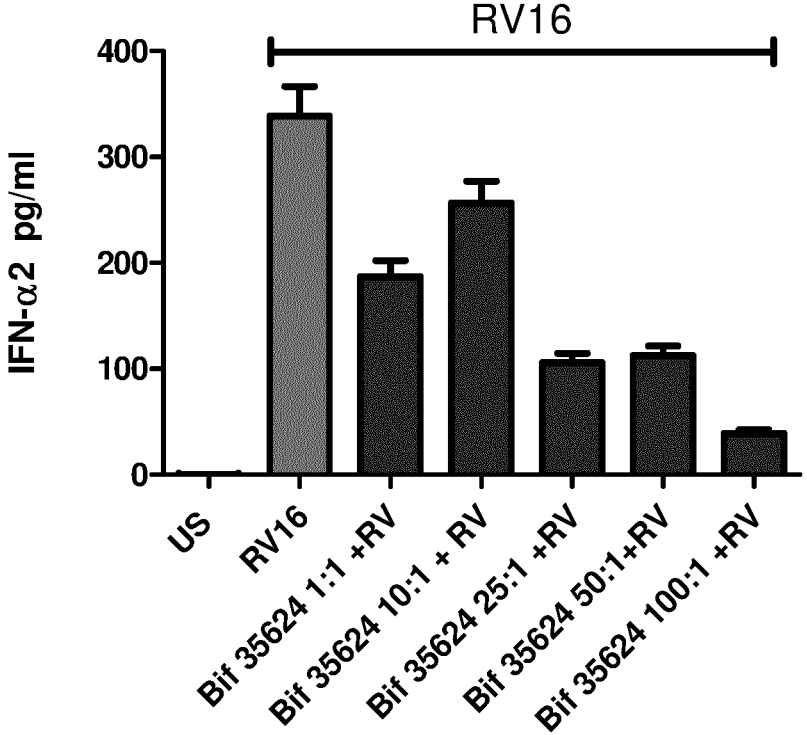
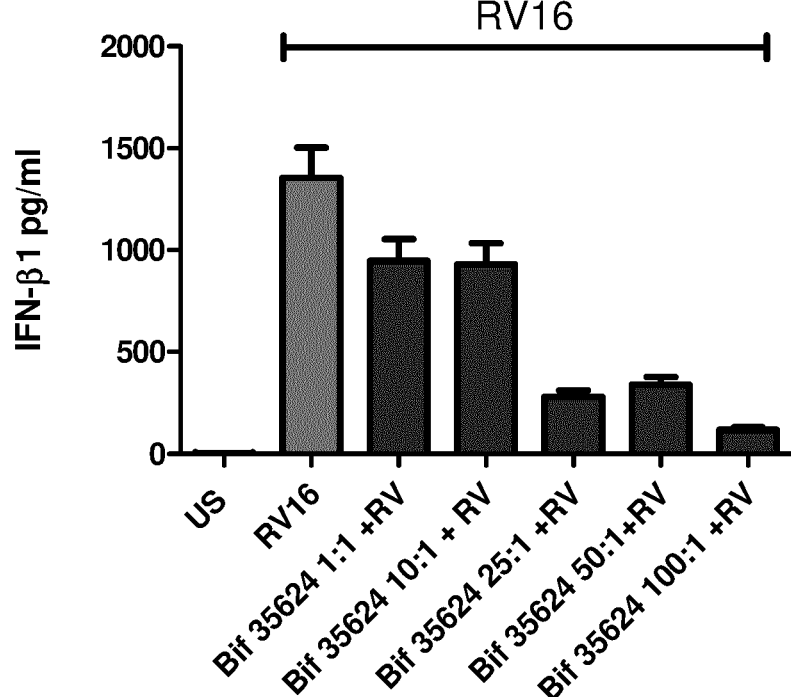
Fig. 18 continued

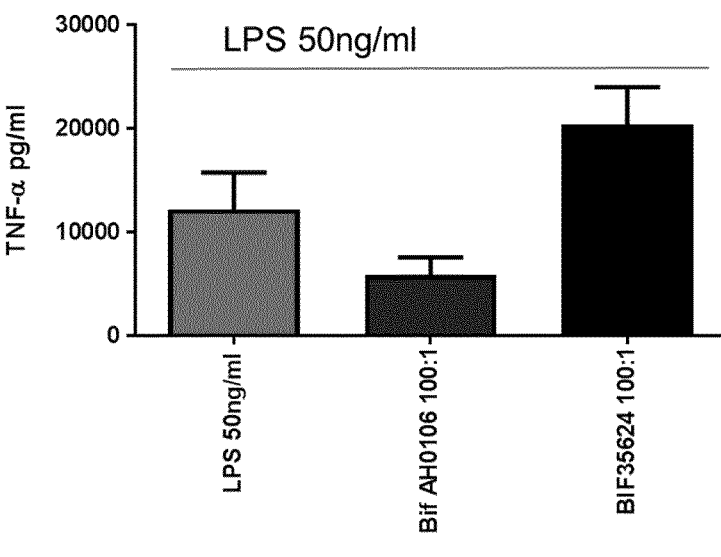
Fig. 28
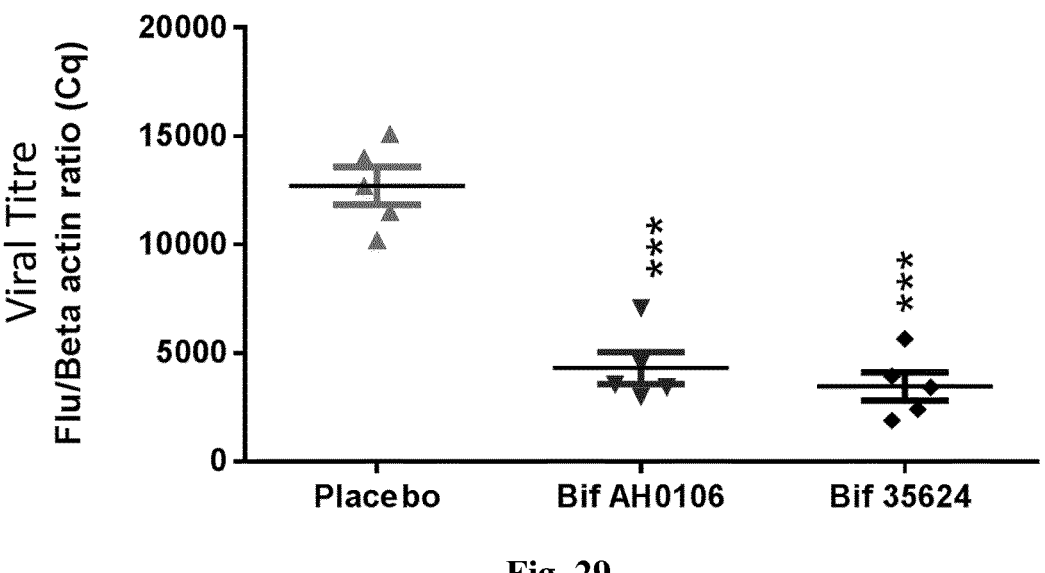
Fig. 29
| % Survival /Days | | | | | |
|---|---|---|---|---|---|
| | Days 1-6 | Day7 | Days 8 | Days 9 | Days 10 |
| Placebo | 100 | 40 | 40 | 20 | 0 |
| Bif AH0106 | 100 | 60 | 60 | 60 | 60 |
| Bif 35624 | 100 | 60 | 40 | 20 | 20 |
Fig. 30

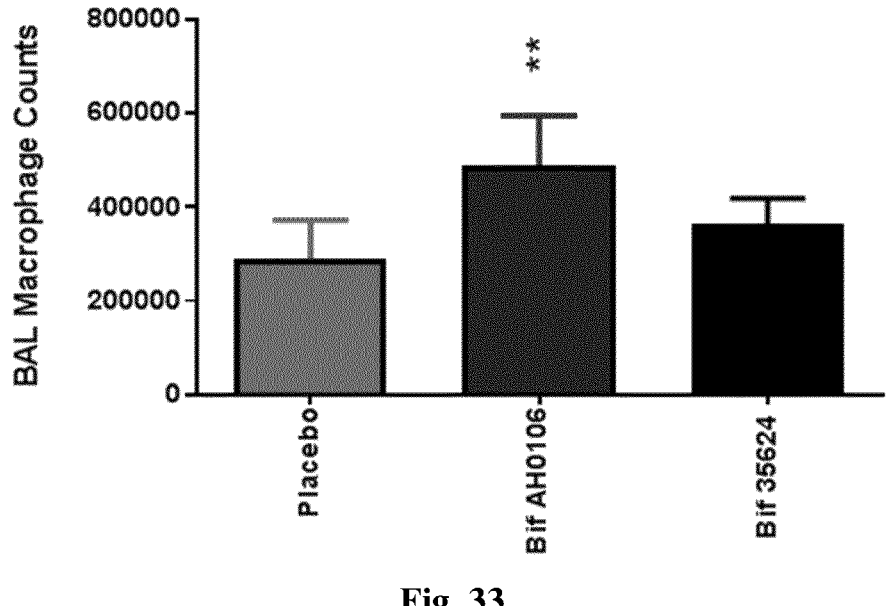
<u>Fig. 33</u>

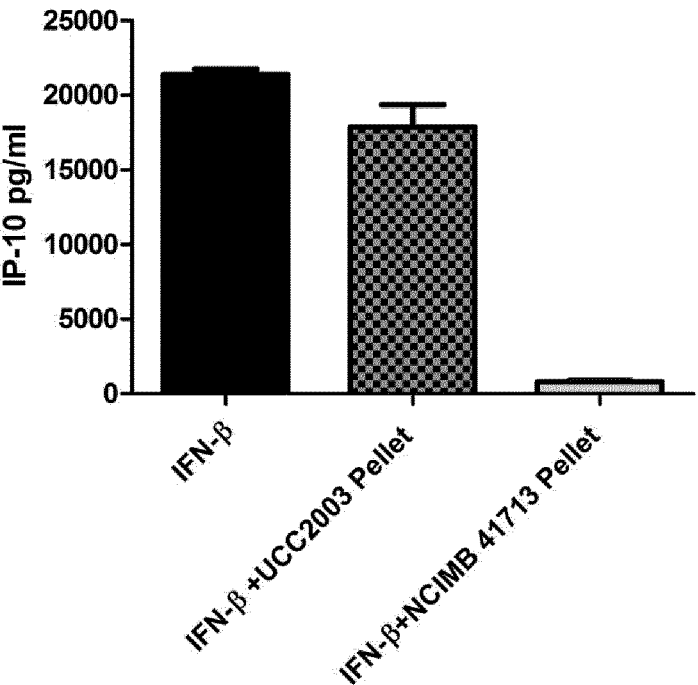
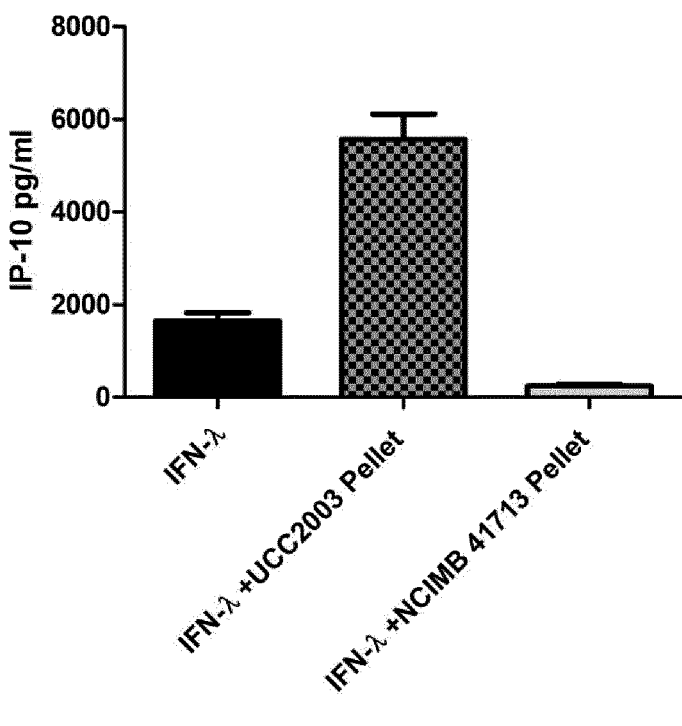
Fig 40

BIFIDOBACTERIUM LONGUM

CROSS-REFERENCE TO RELATED APPLICATIONS

This application is the U.S. national phase entry under 35 U.S.C. § 371 of International Application No. PCT/EP2021/056431, filed on Mar. 12, 2021, which claims the benefit of priority to European Application No. 20163197.5, filed on Mar. 13, 2020, European Application No. 21160580.3, filed on Mar. 3, 2021 and European Application No. 21160660.3, filed on Mar. 4, 2021.

SEQUENCE LISTING

This application contains a sequence listing, submitted electronically in ASCII format under the file name Sequence_Listing.txt, which is incorporated by reference herein in its entirety. The ASCII copy of the sequence listing was created on Sep. 9, 2022, and is 678 bytes in size.

FIELD OF THE INVENTION

The invention relates to Bifidobacteria which are one of several predominant culturable bacteria present in human colonic microflora.

BACKGROUND OF THE INVENTION

Bifidobacteria are considered to be probiotics as they are living organisms which exert healthy effects beyond basic nutrition when ingested in sufficient numbers. A high level of ingested bifidobacteria must reach their site of action in order to exert a probiotic effect. A minimum level of approximately $10^6$-$10^7$ viable bifidobacteria per gram intestinal contents has been suggested (Bouhnik, Y., Lait 1993). There are reports in the literature which show that in vivo studies completed in adults and in infants indicate that some strains of bifidobacteria are capable of surviving passage through the gastrointestinal tract. Significant differences have been observed between the abilities of different bifidobacteria strains to tolerate acid and bile salts, indicating that survival is an important criterion for the selection of potential probiotic strains.

Ingestion of bifidobacteria can improve gastrointestinal transit and may prevent or assist in the treatment of illnesses which may be caused by deficient or compromised microflora such as gastrointestinal tract (GIT) infections, constipation, irritable bowel syndrome (IBS), inflammatory bowel disease (IBD)—Crohn's disease and ulcerative colitis, food allergies, antibiotic-induced diarrhoea, cardiovascular disease, and certain cancers (e.g. colorectal cancer).

Viral infections are a major cause of morbidity and mortality. Virus infections of the respiratory tract account for a substantial increase in morbidity and mortality in the elderly. Coronaviruses are highly infectious viruses that usually are successfully cleared by an appropriate host immune response in healthy individuals. However much of the issue with these infections is not the initial virus but rather the secondary infections that often accompany it e.g. bacterial infections causing pneumonia, infection of sinus tissue etc. In recent times pathogenic human CoVs such as severe acute respiratory syndrome CoV (SARS-CoV) and SARS-Cov-2 and Middle East respiratory syndrome CoV (MERS-CoV) have originated from bats and transmitted to humans from an intermediate host such as civet cats and dromedary camels or an unknown zoonotic source animal in the food market in Wuhan China. SARS-CoV-2 seems to have a predilection for the elderly male population and for patients with co-morbidities such as cardiovascular diseases, hypertension and diabetes. Other risk factors include smoking, old age and co infection with bacterial infections which can all lead to lethal viral pneumonia. Impaired innate and adaptive antiviral responses are, in part, responsible for increased disease severity in the elderly.

Susceptible individuals respond very poorly to these SARS-Cov or MERS-CoV infections and subsequent secondary infections are serious and can be life threatening to such individuals. These SARS-Cov or MERS-CoV-induced exacerbations in individuals are associated with substantial healthcare costs and significant suffering. Initially, the pandemic COVID-19, caused by SARS-CoV-2, was considered to be an exclusive lung disease, eventually leading to serious respiratory symptoms. In the meantime, accumulating experimental and clinical studies have suggested that SARS-CoV-2 may also cause lesions in the kidneys, heart, brain, and gastrointestinal and endocrine organs. Development of new and effective therapies for these exacerbations would be beneficial as there is a major unmet clinical need.

STATEMENTS OF INVENTION

The invention provides a *Bifidobacterium longum* strain for use in the prophylaxis or treatment of a coronavirus infection in a subject.

The invention also provides a *Bifidobacterium longum* strain for use in the prophylaxis of a secondary bacterial infection associated with a coronavirus infection in a subject.

The *Bifidobacterium longum* may attenuate the IP-10 response to a coronavirus.

The *Bifidobacterium longum* may enhance the type III interferon response to a coronavirus.

The *Bifidobacterium longum* may enhance the interferon lambda response to a coronavirus.

The *Bifidobacterium longum* may suppress the interferon type I response to a coronavirus.

The *Bifidobacterium longum* may suppress the interferon alpha response to a coronavirus.

The *Bifidobacterium longum* may suppress the interferon beta response to a coronavirus.

The *Bifidobacterium longum* may enhance the surfactant protein D response to a coronavirus.

In one case the coronavirus is a respiratory coronavirus. The coronavirus may be SARS-CoV-2.

The subject may have been diagnosed with an inflammatory lung disease.

The subject may have increased susceptibility to a respiratory infection.

The subject may be an acute respiratory distress syndrome (ARDS) patient.

The subject may be an asthma patient.

The subject may be obese.

The subject may be a chronic obstructive pulmonary disease (COPD) patient.

The subject may be an elderly person greater than 60 years of age.

The *Bifidobacterium longum* may be strain NCIMB 41003.

The *Bifidobacterium longum* may be strain NCIMB 41715.

The *Bifidobacterium longum* may be strain NCIMB 41713.

The invention also provides a formulation comprising a strain of *Bifidobacterium longum* wherein the *Bifidobacterium longum* attenuates a response, such as the IP-10 response, to a coronavirus.

In one case the coronavirus is a respiratory coronavirus such as SARS-CoV-2.

The formulation may be adapted for administration to the lung or to the nose.

The formulation may comprise a nasal spray.

The formulation may comprise an oral spray.

The formulation may comprise a prebiotic material, a carrier, an adjuvant, a drug entity, and/or a biological compound.

The *Bifidobacterium longum* may be strain NCIMB 41003.

The *Bifidobacterium longum* may be strain NCIMB 41715.

The *Bifidobacterium longum* may be strain NCIMB 41713.

The *Bifidobacterium longum* may be strain NCIMB 42020.

The formulation may have a viscosity of from 1 cps to 2000 cps.

Also provided is a cell wall fraction isolated from a strain of *Bifidobacterium longum* which enhances a response to a coronavirus.

The cell wall fraction may attenuate the IP-10 response to the coronavirus.

The cell wall fraction may enhance the type III interferon response to the coronavirus.

The cell wall fraction may enhance the interferon lambda response to the coronavirus.

The cell wall fraction may suppress the interferon type I response to the coronavirus.

The cell wall fraction may suppress the interferon alpha response to the coronavirus.

The cell wall fraction may suppress the interferon beta response to the coronavirus.

The cell wall fraction may enhance the surfactant protein D response to the coronavirus.

In one case the coronavirus is a respiratory coronavirus.

The coronavirus may be SARS-CoV-2.

The molecular weight of the cell wall fraction may be greater than 100 kDa.

The cell wall fraction may be less than 0.45 μm in size.

The cell wall fraction may be isolated by opening the *Bifidobacterium longum* and separating the cell wall fraction from a cytoplasmic fraction.

The opening of the *Bifidobacterium longum* may comprise at least one of:— treating with a chelating agent;

treating with an enzyme; and applying shear force.

The chelating agent may be a calcium chelating agent such as ethylenediaminetetraacetic acid (EDTA).

The enzyme may be a glycoside hydrolase such as lysozyme.

The enzyme may be a muralytic enzyme such as mutanolysin.

The shear force may be applied by sonication and/or by pressure such as by a French press.

In one case the separation comprises centrifugation.

After separation the cell wall fraction may be filtered to provide a fraction with a size of less than 0.45 μm.

The *Bifidobacterium longum* may be strain NCIMB 41003.

The *Bifidobacterium longum* may be strain NCIMB 41715.

The *Bifidobacterium longum* may be strain NCIMB 41713.

The *Bifidobacterium longum* may be strain NCIMB 42020.

The invention also provides a formulation which comprises a cell wall fraction as defined The formulation may comprise a prebiotic material.

The formulation may comprise an ingestible carrier. The ingestible carrier may be a pharmaceutically acceptable carrier such as a capsule, tablet or powder. The ingestible carrier may be a food product such as acidified milk, yoghurt, frozen yoghurt, milk powder, milk concentrate, ice-cream, cheese spreads, dressings or beverages.

The formulation may comprise a protein and/or peptide, in particular proteins and/or peptides that are rich in glutamine/glutamate, a lipid, a carbohydrate, a vitamin, mineral and/or trace element.

In one embodiment the formulation comprises Vitamin D.

The Vitamin D may be present in the formulation in an amount of at least 5 μg (0.005 mg). In one case the Vitamin D is present in the formulation in an amount of about 10 μg (0.01 mg).

In one embodiment the formulation is in the form of a tablet, especially a chewable/suckable tablet.

The formulation may comprise an adjuvant, a drug entity, and/or a biological compound.

The formulation may be adapted for administration to the lung or to the nose.

The formulation may comprise a nasal spray.

The formulation may comprise a spray for spraying orally into the nasopharynx region.

The formulation may have viscosity of from 1 cps to 2000 cps.

Also provided is a cell wall fraction isolated from a *Bifidobacterium longum* strain for use in the prophylaxis or treatment of a coronavirus infection in a subject.

A cell wall fraction isolated from a *Bifidobacterium longum* strain is provided for use in the prophylaxis of a secondary bacterial infection associated with a coronavirus infection in a subject.

The cell wall fraction may attenuate the IP-10 response to the coronavirus.

The cell wall fraction may enhance the type III interferon response to the coronavirus.

The cell all fraction may enhance the interferon lambda response to the coronavirus.

The cell wall fraction may suppress the interferon type I response to the coronavirus.

The cell wall fraction may suppress the interferon alpha response to the coronavirus.

The cell wall fraction may suppress the interferon beta response to the coronavirus.

The cell wall fraction may enhance the surfactant protein D response to the coronavirus.

In one case the coronavirus is a respiratory coronavirus.

The coronavirus may be SARS-CoV-2.

The subject may have been diagnosed with an inflammatory lung disease.

The subject may have increased susceptibility to a respiratory infection.

The subject may be an acute respiratory distress syndrome (ARDS) patient.

The subject may be an asthma patient.

The subject may be obese.

The subject may be a chronic obstructive pulmonary disease (COPD) patient.

The subject may be an elderly person greater than 60 years of age.

The subject may be a child less than 5 years of age.

The molecular weight of the cell wall fraction may be greater than 100 kDa.

The cell wall fraction may be less than 0.45 μm in size.

The *Bifidobacterium longum* may be strain NCIMB 42020.

The *Bifidobacterium longum* may be strain NCIMB 41003.

The *Bifidobacterium longum* may be strain NCIMB 41715.

The *Bifidobacterium longum* may be strain NCIMB 41713.

The invention also provides a formulation comprising a *Bifidobacterium longum* strain and Vitamin D.

The invention further provides a formulation comprising a cell wall fraction of a *Bifidobacterium longum* strain and Vitamin D.

In one cage the *Bifidobacterium longum* is the strain having the accession number NCIMB 42020.

In another case the *Bifidobacterium longum* is the strain having the accession number NCIMB 41003.

In one case the *Bifidobacterium longum* is the strain having the accession number NCIMB 41713.

In one case the *Bifidobacterium longum* is the strain having the accession number NCIMB 41715.

The strain may be in the form of viable cells and/or in the form of non-viable cells.

The *Bifidobacterium* strain may be in the form of a freeze-dried powder.

The *Bifidobacterium* strain may be present in an amount of more than $10^6$ cfu per gram of the formulation.

The Vitamin D may be present in the formulation in an amount of at least 5 μg (0.005 mg). In one case the Vitamin D is present in the formulation in an amount of about 10 μg (0.01 mg).

In one embodiment the formulation is in the form of a tablet, especially a chewable/suckable tablet.

The formulation may be adapted for administration to the lung or to the nose.

The formulation may comprise a nasal spray.

The formulation may comprise a spray for spraying orally into the nasopharynx region.

The strain the may be isolated from faeces or gastrointestinal tract of healthy human subjects.

The strain may be in the form of a freeze-dried powder.

The strain attenuates the IP-10 response to a virus. This is important because IP-10 is secreted by several cell types in response to IFN-γ. These cell types include monocytes and endothelial cells. IP-10 has been attributed to several roles, including chemoattraction for monocytes/macrophages, T cells, NK cells, and dendritic cells, and promotion of T cell adhesion to endothelial cells and is a marker of viral induced host system activation.

The strain may enhance the type III interferon response to a virus such as the interferon lambda response to a virus.

The strain may suppress the interferon type I response to a virus such as the interferon alpha response to a virus and/or the interferon beta response to a virus.

The strain may enhance the surfactant protein D response to a virus.

The formulation may further comprise another probiotic material. In particular, the formulation may comprise more than one *Bifidobacterium longum* strain such as those mentioned herein. For example, the strain may be selected from one or more of *Bifidobacterium longum* NCIMB 42020, *Bifidobacterium longum* NCIMB 41003, *Bifidobacterium longum* NCIMB 41713, and *Bifidobacterium longum* NCIMB 41715.

Alternatively, or additionally, the formulation may comprise a prebiotic material.

The formulation may further comprise a protein and/or peptide, in particular proteins and/or peptides that are rich in glutamine/glutamate, a lipid, a carbohydrate, another vitamin, a mineral and/or a trace element.

The *Bifidobacterium* strain may be present in an amount of more than $10^6$ cfu per gram of the formulation.

The formulation may further comprise an adjuvant, a drug entity, and/or a biological compound.

The formulation may be for use in the prophylaxis and/or treatment of undesirable inflammatory activity.

The formulation may be for use in the prophylaxis or treatment of a viral infection in a subject.

The formulation may be for use in the prophylaxis of a secondary bacterial infection associated with a respiratory viral infection in a subject.

The virus in some cases is a respiratory virus which may be selected from influenza virus, rhinovirus, and respiratory syncytial virus. The virus may be a coronavirus such as SARS CoV 2.

The subject may have been diagnosed with an inflammatory lung disease.

In some cases the subject has increased susceptibility to a respiratory infection.

The subject may be one or more of obese, an acute respiratory distress syndrome (ARDS) patient, an asthma patient, or a chronic obstructive pulmonary disease (COPD) patient.

In one case the subject is a child less than 5 years of age.

In another case the subject is an elderly person greater than 60 years of age.

The strain may be in the form of viable cells. The strain may be in the form of non-viable cells. The general use of probiotic bacteria is in the form of viable cells. However, use can also be extended to non-viable cells such as killed cultures, mixtures of viable and non-viable cultures or compositions containing beneficial factors expressed by the probiotic bacteria. This could include thermally killed micro-organisms or micro-organisms killed by exposure to altered pH or subjection to pressure or gamma irradiation. With non-viable cells product preparation is simpler, cells may be incorporated easily into pharmaceuticals and storage requirements are much less limited than viable cells. *Lactobacillus casei* YIT 9018 offers an example of the effective use of heat killed cells as a method for the treatment and/or prevention of tumour growth as described in U.S. Pat. No. 4,347,240.

The invention also includes mutants and variants of the deposited strains. Throughout the specification the terms mutant, variant and genetically modified mutant include a strain whose genetic and/or phenotypic properties are altered compared to the parent strain. Naturally occurring variant includes the spontaneous alterations of targeted properties selectively isolated. Deliberate alteration of parent strain properties is accomplished by conventional (in vitro) genetic manipulation technologies, such as gene disruption, conjugative transfer, etc. Genetic modification includes introduction of exogenous and/or endogenous DNA sequences into the genome of a strain, for example by insertion into the genome of the bacterial strain by vectors, including plasmid DNA, or bacteriophages.

Natural or induced mutations include at least single base alterations such as deletion, insertion, transversion or other DNA modifications which may result in alteration of the amino acid sequence encoded by the DNA sequence.

The terms mutant, variant and genetically modified mutant also include a strain that has undergone genetic alterations that accumulate in a genome at a rate which is consistent in nature for all micro-organisms and/or genetic alterations which occur through spontaneous mutation and/or acquisition of genes and/or loss of genes which is not achieved by deliberate (in vitro) manipulation of the genome but is achieved through the natural selection of variants and/or mutants that provide a selective advantage to support the survival of the bacterium when exposed to environmental pressures such as antibiotics. A mutant can be created by the deliberate (in vitro) insertion of specific genes into the genome which do not fundamentally alter the biochemical functionality of the organism but whose products can be used for identification or selection of the bacterium, for example antibiotic resistance.

A person skilled in the art would appreciate that mutant or variant strains of can be identified by DNA sequence homology analysis with the parent strain. Strains of having a close sequence identity with the parent strain without demonstrable phenotypic or measurable functional differences are considered to be mutant or variant strains. A strain with a sequence identity (homology) of 99.5% or more with the parent DNA sequence may be considered to be a mutant or variant. Sequence homology may be determined using online homology algorithm "BLAST" program, publicly available at http://www.ncbi.nlm.nih.gov/BLAST/.

The invention will be more clearly understood from the following description thereof given by way of example only.

BRIEF DESCRIPTION OF THE DRAWINGS

The invention will be more clearly understood from the following description thereof, given by way of ex ample only, with reference to the accompanying figures in which:—

FIG. 2(*b*) is a graph of the IP-10 response to human rhinovirus (HRV16) compared to unstimulated (US) in the presence of a cell wall fraction (Bif pellet) from strain 41003 in Monocyte Derived Dendritic cells;

FIG. 2(*c*) is a graph of the IFN-α, response to human rhinovirus (HRV16) compared to unstimulated (US) in the presence of a cell wall fraction (Bif pellet) from strain 41003 in Monocyte Derived Dendritic cells;

FIG. 2(*d*) is a graph of the IFN-β response to human rhinovirus (HRV16) compared to unstimulated (US) in the presence of a cell wall fraction (Bif pellet) from strain 41003 in Monocyte Derived Dendritic cells;

FIG. 2(*e*) is a heat map of the cytokine response to human rhinovirus (HRV16) in the presence of a cell wall fraction (Bif pellet) from strain 41003 in Monocyte Derived Dendritic cells;

FIG. 2(*f*) is a bar chart of the IP-10 response to human rhinovirus (HRV16) compared to unstimulated (US) in the presence of cytoplasmic fractions compared to a cell wall fraction (Bif pellet) from strain 41003 in Monocyte Derived Dendritic cells;

FIG. 3(*b*) is a graph of the IP-10 response to human rhinovirus (HRV16) in the presence of a cell wall fraction from strain 41003 (Bif WT) and a genetically modified strain which is missing exopolysaccharide (Bif KO) in Monocyte Derived Dendritic cells;

FIG. 6 is a bar chart of the secretion of IP-10 in response to interferon gamma and interferon beta and interferon lambda in the presence of a cell wall fraction from strain UCC2003 (Bif UCC2003 pellet) compared to a cell wall fraction from strain 41003 (Bif 35624 pellet) in Monocyte Derived Dendritic cells;

FIG. 9(*b*) is a graph of survival over a time period post infection with the cell wall fraction (Bif pellet) of strain 41003;

FIG. 10 is a graph of viral replication in the lung in response to a cell wall fraction (Bif pellet) from strain 41003 following viral infection;

FIG. 11 is a series of graphs of cytokine and surfactant protein D responses in the BALF to a cell wall fraction (Bif pellet) from strain 41003 following viral infection;

FIG. 13 is a graph of lung damage markers in the BALF in response to cell wall fraction (Bif Pellet) from strain 41003 following viral infection;

FIG. 16(*b*) is an illustration of cascade of response to a viral infection mediated by a cell wall fraction or strain of the invention;

FIG. 18 is a series of bar charts of interferon lambda, interferon alpha and interferon beta responses to rhinovirus in the presence of strain 41003;

FIG. 28 is a bar chart of the TNF-α response to LPS in the presence of *B. longum* strains AH0106 and 35624;

FIG. 29 is a graph of viral replication in the lung in response to the strains *B. longum* AH0106, *B. longum* 35624 and placebo following viral infection;

FIG. 30 is a graph of survival over a time period post infection with the *B. longum* strains AH0106, 35624 and placebo;

FIG. 33 is a graph of BAL count of Macrophages in response to the strains *B. longum* strains AH0106, 35624 and placebo, following viral infection;

FIG. 34(*b*) is a graph of the IFN-α response to human rhinovirus (HRV16) in the presence of a cell wall fraction (Bif AH0106 pellet) from strain AH0106 in Monocyte Derived Dendritic cells;

FIG. 34(*c*) is a graph of the IFN-β response to human rhinovirus (HRV16) in the presence of a cell wall fraction (Bif AH0106 pellet) from strain AH0106 in Monocyte Derived Dendritic cells;

FIG. 35(*b*) is a bar chart of the IP-10 response to interferon beta (IFN-β) in the presence of a cell wall fraction from strain UCC2003 compared to a cell wall fraction from strain AH0106 in Monocyte Derived Dendritic cells;

FIG. 36(*b*) is a bar chart of the TNF-α response to Poly:IC in the presence of a cell wall fraction from strain UCC2003 compared to a cell wall fraction from *B. longum* strains AH0106 and 35624 in Monocyte Derived Dendritic cells;

FIG. 38(*b*) is a graph of the IFN-α response to rhinovirus (RV16) in the presence of a cell wall fraction (Bif AH0103 pellet) from strain AH0103 in Monocyte Derived Dendritic cells;

FIG. 38(*c*) is a graph of the IFN-β response to rhinovirus (RV16) in the presence of a cell wall fraction (Bif AH0103 pellet) from strain AH0103 in Monocyte Derived Dendritic cells;

FIG. 42(*b*) is a graph of the IFN-α response to rhinovirus (RV16) in the presence of a cell wall fraction (Bif AH1362 pellet) from strain AH1362 in Monocyte Derived Dendritic cells; and FIG. 42(*c*) is a graph of the IFN-β response to rhinovirus (RV16) in the presence of a cell wall fraction (Bif AH1362 pellet) from strain AH1362 in Monocyte Derived Dendritic cells.

DETAILED DESCRIPTION

Figure 1:
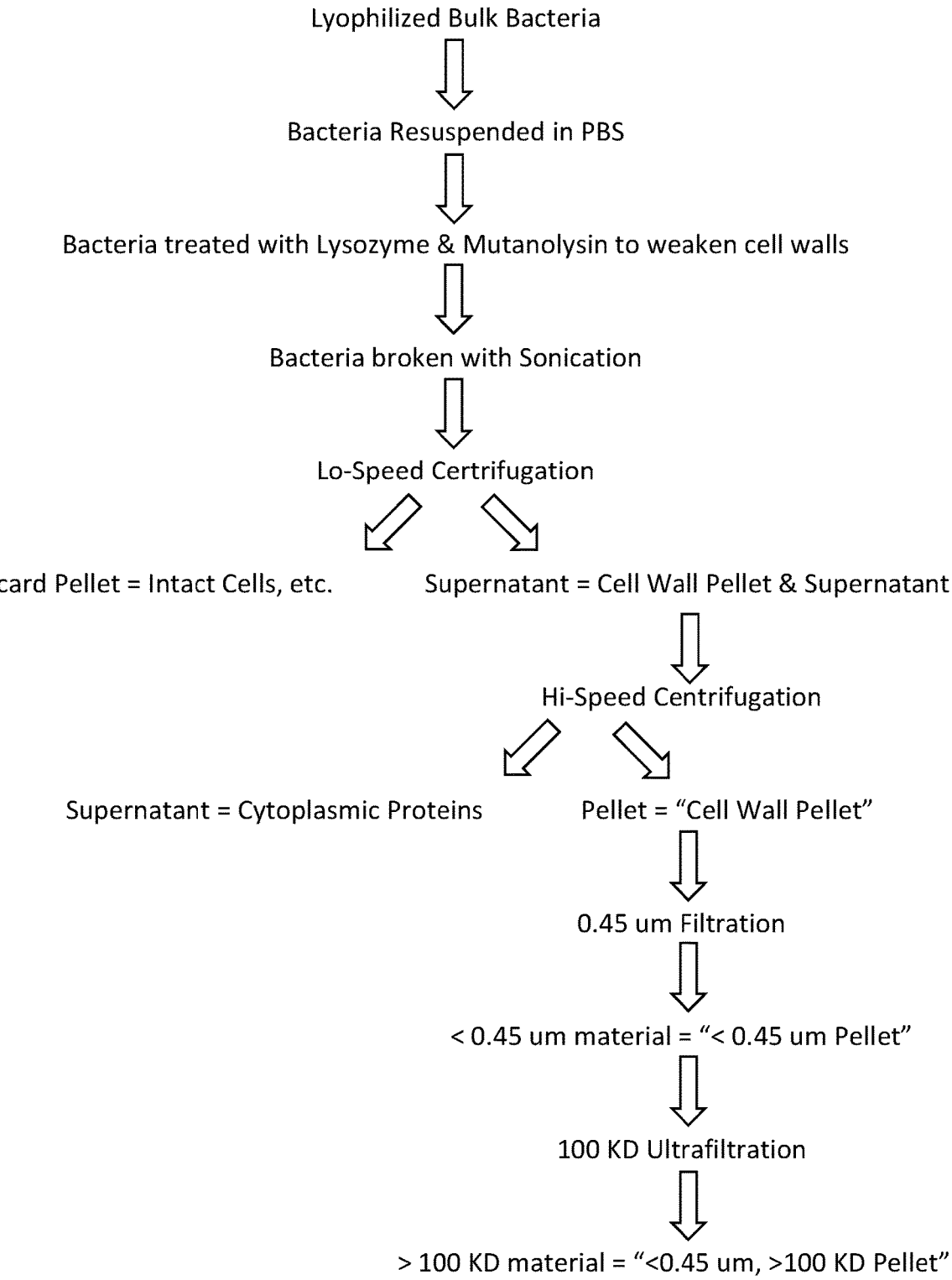
FIG. 1 is a flow chart of a process used for isolating a cell wall fraction from *Bifidobacterium longum* NCIMB 41003 (35624®)
Figure 2A:
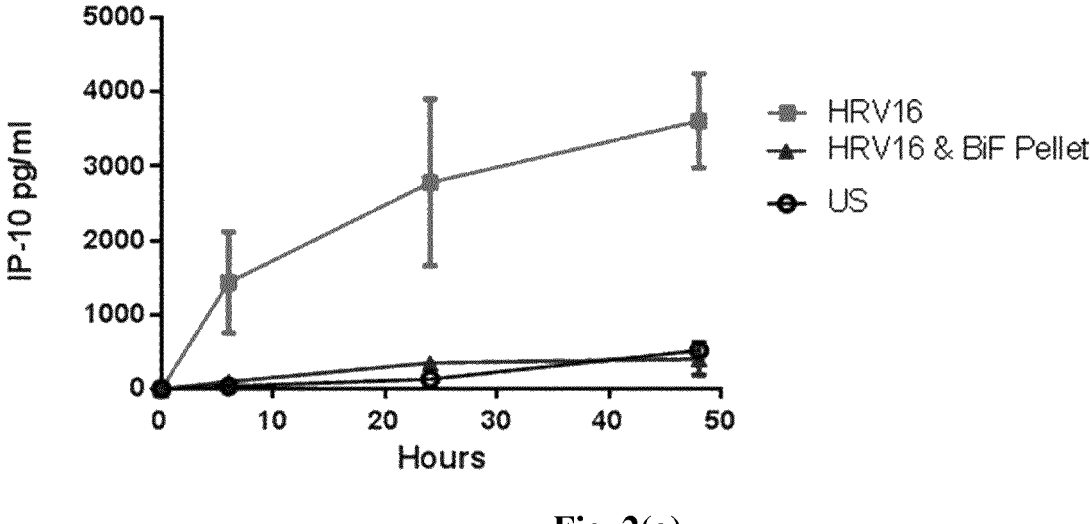
FIG. 2(*a*) is a graph of the IP-10 response to human rhinovirus (HRV16) compared to unstimulated (US) in the presence of a cell wall fraction (Bif pellet) from strain 41003 in Monocytes.
Figure 2B:
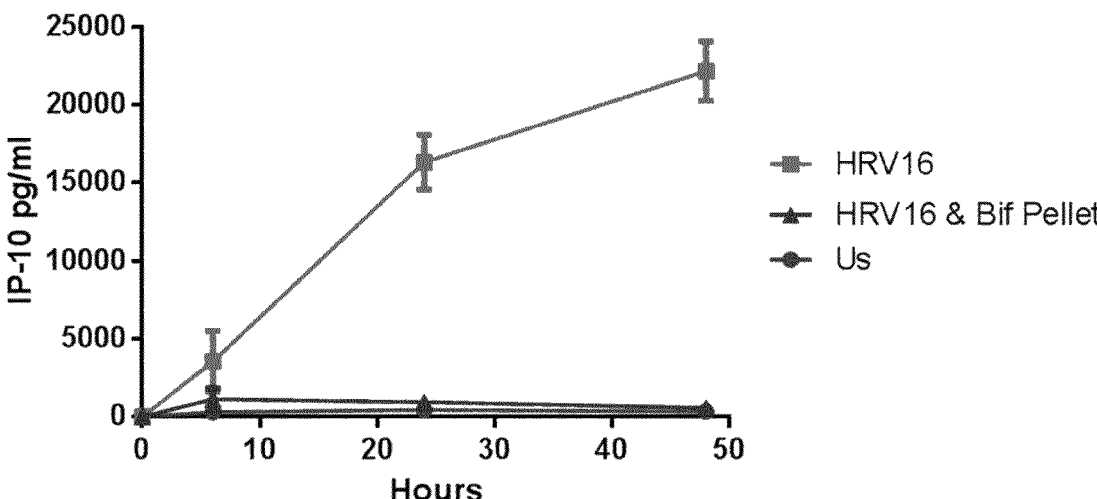
Figure 2C:
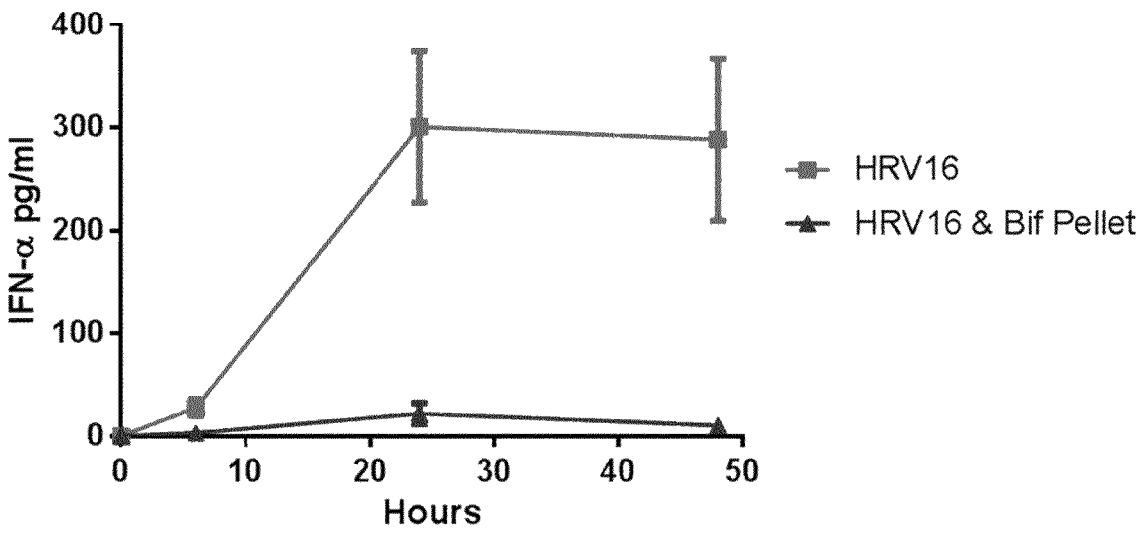
Figure 2D:
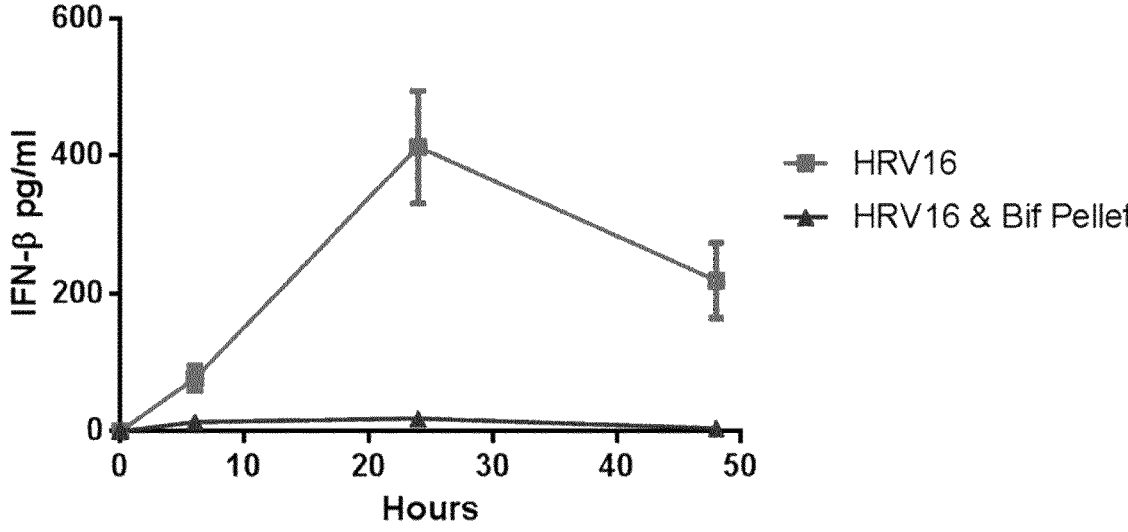
Figure 2E:
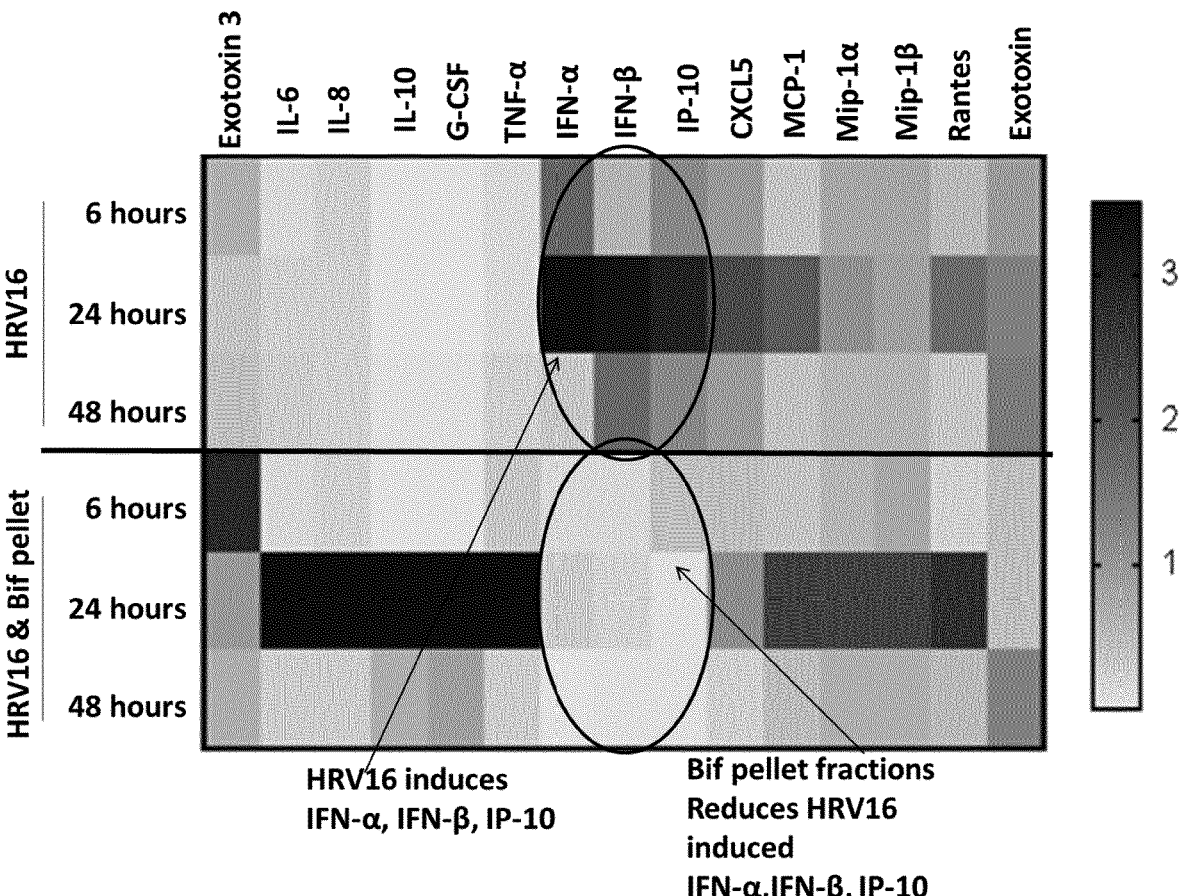
Figure 2F:
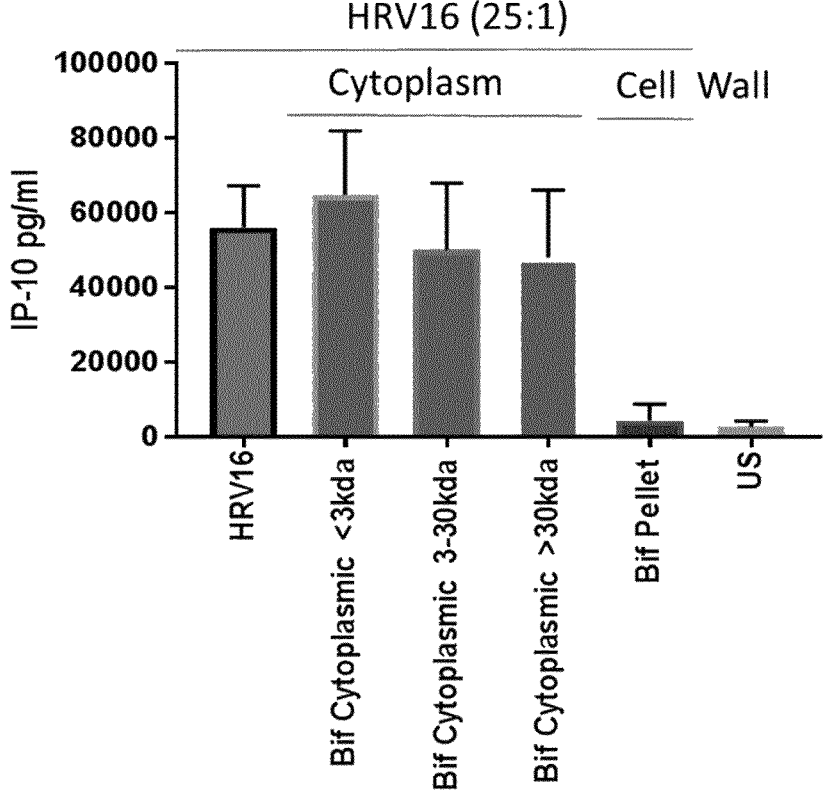

The invention provides therapeutic agents which can induce Type III IFN-λ and/or SP-D and have a role to play in early clearance of the primary viral infection while reducing the likelihood of secondary bacterial infections and would be a significant advancement in the management of ARDS caused by pathogenic Cov. and its newer variant SARS-CoV-2.

Lung surfactant protein D (SP-D) can selectively recognized SARS coronavirus spike glycoprotein and enhances phagocytosis (Leth-Larsen et al 2007). Again, therapeutic agents that can induce this innate sensor which can bind to the virus to aid phagocytosis and stop it from infecting the bronchial epithelial cells would be a significant advancement in the treatment of SARS-Cov or MERS-CoV infections. More recently a recombinant fragment of human SP-D has been shown to neutralize SARS-CoV-2 (Watson et al., 2021). A study by Kerget et al., (2020) found SP-D to be higher in COVID-19 patients compared to the control group and levels were strongly associated with ARDS development. These studies confirm the potential of SP-D as a biomarker and treatment strategy for COVID-19 patients.

A deposit of *Bifidobacterium longum* strain AH0103 was made under the terms of the Budapest Treaty at the National Collections of Industrial and Marine Bacteria Limited (NCIMB) Ferguson Building, Craibstone Estate, Bucksburn, Aberdeen, AB21 9YA, Scotland, UK on May 6, 2010 and accorded the accession number NCIMB 41713. This strain is described in WO2018/158309.

A deposit of *Bifidobacterium longum* strain AH0106 was made under the terms of the Budapest Treaty at the National Collections of Industrial and Marine Bacteria Limited (NCIMB) Ferguson Building, Craibstone Estate, Bucksburn, Aberdeen, AB21 9YA, Scotland, UK on 2 Aug. 2012 and accorded the accession number NCIMB 42020. This strain is described in WO2018/158309.

A deposit of *Bifidobacterium longum* AH1362 was made under the terms of the Budapest Treaty at the National Collections of Industrial and Marine Bacteria Limited (NCIMB) Ferguson Building, Craibstone Estate, Bucksburn, Aberdeen, AB21 9YA, Scotland, UK on May 6, 2010 and accorded the accession number NCIMB 41715. This strain is described in WO2017/097987A.

The strain *Bifidobacterium* longum 35624 was deposited under the terms of the Budapest Treaty at the National Collections of Industrial and Marine Bacteria Limited (NCIMB) Ferguson Building, Craibstone Estate, Bucksburn, Aberdeen, AB21 9YA, Scotland, UK on Jan. 13, 1999 under accession number NCIMB 41003. This strain is described in WO00/42168A.

*Bifidobacterium longum* strains and cell wall fractions isolated from *Bifidobacterium* longum strains are useful in the prophylaxis or treatment of a respiratory viral infection in a subject caused by a coronavirus. The strains and cell wall fractions are useful in the prophylaxis of a secondary bacterial infection associated with a respiratory viral infection in a subject caused by a coronavirus. The strains and cell wall fractions are particularly useful in subjects which have increased susceptibility to a respiratory infection.

In the case of viral infections, we have identified a cell wall fraction that is a non-viable component of *B. longum* strains that is surprisingly effective in reducing viral infections, associated secondary bacterial infections and associated inflammatory processes, using a targeted and immune balancing method of action not identified before. We have demonstrated that this fraction can be isolated from more than one related *B. longum* strain but is not present in other bifidobacteria. In addition we have demonstrated that, in a further surprising result, the related viable stains from which this fraction can be isolated can be used in a similar way to the isolated cell wall fraction to modulate host immune response to virus in the respiratory system in a targeted fashion, especially upon delivery to the nose. This effect of both fraction and strain is both preventative and therapeutic.

A cell wall fraction of NCIMB 41003 (35624® strain) promotes anti-viral defence and inhibits damaging pro-inflammatory responses and is particularly useful in the prevention and/or treatment of virus induced ARDS, or viral-induced exacerbations and also virus induced bacterial superinfections in asthma and COPD patients or obese individuals.

It is now well established that the commensal microbiota is required for optimal host development and for ongoing immune homeostasis, which involves inter-dependent interactions between microbes and immunity. This requires discriminative responses to commensals in comparison to pathogens to ensure tolerance and protective immunity respectively. A characteristic feature of mucosal tolerance is the induction and expansion of Foxp3+ T regulatory cells which limit excessive pro-inflammatory responses. The 35624@strain has been shown to reduce pro-inflammatory responses to infection within the gastrointestinal tract in mice and protects against inflammatory diseases in humans via the induction of regulatory immune responses (O'Mahony L. et al. 2005; O'Mahony C. et al., 2008; Konieczna P. et al. 2012; Groeger D. et al., 2013).

A cell wall fraction from *B. longum* 35624 strain has potent anti-viral properties not associated with the strains EPS and with a different effect in human disease progression linked to suppression of viral replication and secondary pro-inflammatory responses.

Example 1: Cell Wall Pellet Generation

Bacterial Harvesting/Washing
Method:
   1. The equivalent of 250 ml of original bacterial biomass (total cell count=$1.5\times10^{11}$) is harvested by centrifugation (14000 rpm, 4° C., 20 min; rotor JA-20 (Avanti J-26 x P Beckman Coulter). The bacterial pellet is washed with sterile PBS and the supernatant is discarded and washed again (repeat two more times).
   2. For viable and non-viable lyophilised bacteria (0.5 g of $3.0\times10^{11}$ powder or total cell count=$1.5\times10^{11}$) was resuspended in 50 mls and harvested by centrifugation (14000 rpm, 4° C., 20 min; rotor JA-20 (Avanti J-26 x P Beckman Coulter). The bacterial pellet is washed with sterile PBS and the supernatant is discarded and washed again (repeat two more times).
   3. Finally the pellet is resuspended in 50 ml of sterile PBS and the bacterial solution divided into two 25 ml aliquots Cell Disruption The aim of this procedure was for the generation of a cell wall fraction from the whole bacteria and the elimination of the cytoplasmic fraction and other components. This involves one or more steps selected from:

treatment with a chelating agent optionally in conjunction with freeze thaw procedure to prevent DNAse or protease activity when using enzymatic treatment to aid lysis.

Enzymatic treatment with a glycoside hydrolase and/or N-acetylmuramidase.

Application of shear force such as ultra-sonication or application of high pressure such as using a French press.

Separation of the cell wall fraction from the cytoplasmic fraction by using centrifugation Filtration of the cell wall fraction.

Materials:

EDTA (0.5M Fluka) is chelator for removal of metal ions (calcium or magnesium) to prevent DNAse or protease activity when using enzymes for cell wall lysis.

Lysozyme (Sigma 10 mg/ml)*endotoxin free is a glycoside hydrolase that catalyses the hydrolysis of 1, 4-beta-linkages between N-acetylmuramic acid and N-acetyl-D-glucosamine residues. This hydrolysis compromises the integrity of bacterial cell walls causing lysis of the bacteria.

Mutanolysin (10 KU Sigma diluted in 1 ml $H_2O$) is an N-acetylmuramidase, which is an muralytic enzyme that cleaves the β-N-acetylmuramyl-(1→4)-N-acetylglucosamine linkage of the bacterial cell wall. This cleavage compromises the integrity of bacterial cell walls causing lysis of the bacteria.

Glass beads 90-150 μM particle size (VWR) used in conjunction with sonication to aid lysis.

Method:

1. Add 250 μl EDTA (0.5M stock Fluka) to each of the 25 ml aliquots therefore having a final concentration of 5 mM EDTA.

2. Freeze the aliquots by placing the 2 aliquots in liquid nitrogen till frozen then thaw the aliquots in water; repeat this procedure twice.

3. Each 25 ml of bacterial aliquot is incubated with 250 μl Lysozyme (10 mg/ml) and 250 μl Mutanolysin (2.5 KU) for 1 hour at 37° C. with an occasional mild vortex. From this step shear force is used either by a sonicator or a French press to disrupt the bacterial cell Sonication A half teaspoon of autoclaved glass beads 90-150 μM particle size (VMR) were added to the bacterial aliquots just before sonication.

Sonicate 25 ml of resuspended bacterial material at a time, then put on ice and sonicate the other aliquot using the Sonicator (VibraCell SONICS) with the 50 ml probe. (Settings Tune=50, Frequency=60). This procedure is repeated four times for 10 minutes on ice.

Following sonication, the glass beads, unbroken cells and cell debris are removed by centrifugation at 1000 rpm for 10 minutes at 4° C.

High pressure with French press

Alternatively, the Bacterial cells are disrupted by pressure of 1500 psi on the high setting (20,000 psi equivalent) using a French press (Thermo Electron Corporation FA-078A). This procedure is repeated three times on ice.

Application of a shear force using the French press results in a clearing of the turbid bacterial cells after the third run. Following French press disruption, the unbroken cells and cell debris are removed by centrifugation at 1000 rpm for 10 minutes at 4° C. and the supernatant containing the cell wall material and cytoplasmic fractions is retained.

4. Following application of a shear force (sonication or high pressure) a supernatant containing the cell wall material and cytoplasmic fractions was retained. This supernatant is centrifuged for 20 min at 14000 rpm at 4° C. to separate the cell wall material from the cytoplasmic material. The supernatant is discarded.

5. The pellet containing the cell wall material is resuspended in 5 ml of PBS per 250 ml of original bacterial biomass. The pellet of cell wall material was centrifuged at 1000 rpm for 10 minutes to remove black residue in the pellet. The pellet containing the cell wall material was stored at −80° C.

Centrifuges and Rotors

Avanti J=E Centrifuge Beckman Coulter

Rotors: JA-20

Sonicator

VibraCel SONICS, Sonics and Materials

Probe 435-09

French Press

French Press FA-078A

Cell FA-032 (40K Standard) (Standard FRENCH Pressure 40,000 psi Cell with 35 ml capacity, pressure up to 40,000 psi)

Size Filtration Followed by Ultrafiltration

Materials:

Polyvinylidene difluoride (PVDF) membrane filters (0.45 μm pore size, Millipore, Bedford, MA)

100 kDa MWCO UF device (Millipore).

1. The resuspended bacterial Pellet containing cell wall material (5 ml) is thawed and filtered through polyvinylidene difluoride (PVDF) membrane filters (0.45 μm pore size, Millipore, Bedford, MA; rinsed thoroughly with PBS before use). The material that comes through the membrane filter is free of intact bacteria and is a cell wall material having a size of <0.45 μm. 4 ml of cell wall material is produced by this 0.45 μm filter step. From the original 250 mls of bacterial culture, 4 ml of the suspended cell wall material remains.

2. The <0.45 μm cell wall material is then ultrafiltered.

a. Rinse UF device first with 15 ml PBS, spin at 3500×g at 4° C.

b. Take the <0.45 μm bacterial Pellet extracts, load ~4 ml into the 100 kDa MWCO UF device.

c. When the >100 kDa upper solution gets lower in volume, diafilter with PBS.

d. The material that comes thru the 100 kDa filter will be retained and stored at −80° C.

e. The retentate should be resuspended in the same volume of PBS as was added to the ultrafiltration device (4 ml). This material is termed the >100 kDa bacterial Pellet. The final dry weight of the cell wall fraction thus produced is 120 mg in 4 mls of retentate which equates to a final concentration is 30 mg of cell wall fraction per 1 ml.

f. This cell wall fraction was concentrated for in vitro and in vivo tests for more enhanced solubility. To make more concentrated material than 30 mg/ml such as 300 mg/ml (10×) or 150 mg/ml (5×) >100 kDa bacterial Pellet solutions the cell wall fraction is just resuspended in 10 times or 5 times less volume than the starting material.

Example 2: The Cell Wall Fraction from the 35624@Strain Beneficially Blocks Type 1 Interferons and Resultant IP-10 Induction (a Pro-Inflammatory Chemokine) in Specific Cell Types (Monocytes and Dendritic Cells)

The excessive immune response by monocytes and dendritic cells to viral infection causes pro-inflammatory responses in the lung. To determine if the cell wall fraction 30 mg/ml from 35624 as produced in Example 1, has a beneficial anti-viral effect, human CD14+ monocytes from peripheral blood, isolated cells were exposed to rhinovirus (RV) and the IP-10 response to RV was monitored. Peripheral blood mononuclear cells (PBMCs) were isolated from healthy donors using density gradient centrifugation. Peripheral blood mononuclear cells (PBMCs) were isolated from healthy donors using density gradient centrifugation. Human peripheral blood monocytes were isolated using CD14 positive isolation with the MACS system (Miltenyi Biotec, 130-050-201). Cells were cultured in cRPMI media (RPMI (Life Technologies, 21875-091)+10% fetal bovine serum (Sigma catalog F4135) and 1% penicillin/streptomycin (Sigma catalog P0781). Monocytes were stimulated with Human rhinovirus 16 (HRV16) (virapure) (multiplicity of infection (MOI) 25:1) for 6 h, 24 h and 48 h time points in cRPMI at 37° C., 5% CO2 following pre-treatment with (1 h) with bacterial fractions or just HRV16 alone. Surprising, of the cytokines screened the IP-10 response to RV was attenuated by $B.$ $longum$ 35624 cell wall pellet fraction (FIG. 2($a$)).

For monocyte-derived dendritic cells generation: Peripheral blood mononuclear cells (PBMCs) were isolated from healthy donors using density gradient centrifugation. Human peripheral blood monocytes were isolated using CD14 positive isolation with the MACS system (Miltenyi Biotec, 130-050-201). Cells were cultured in cRPMI media (Life Technologies, 21875-091) with interleukin 4 1000 U/ml (Novartis) and granulocyte macrophage colony stimulating factor (PeproTech, 300-03) 1000 U/ml for 6 days in order to differentiate them into monocyte-derived dendritic cells (MDDCs). MDDCs were pre-treated with cell wall fractions from $B.$ $longum$ 35624 before being exposed to (HRV16) and the IP-10 response to HRV16 was monitored. MDDCs were stimulated with HRV16 (MOI) 25:1) for 6 h, 24 h and 48 h time points in cRPMI at 37° C., 5% CO2 following pre-treatment (1 h) with cell fractions from $B.$ $longum$ 35624 (30 mg/ml) or just HRV16 alone.

In agreement with the HRV16 stimulated monocytes results above of the 15 cytokines screened, the IP-10 (FIG. 2($b$)), IFN-α (FIG. 2($c$)), and IFN-β (FIG. 2($d$)) response to RV was attenuated by cell wall pellet fraction from $B.$ $longum$ 35624 strain (FIG. 2($e$)). Cytokine secretion was examined by Bio-Plex multiplex suspension array (Bio-Rad Laboratories) (IL-6, IL-8, IL-10, G-CSF, TNF-α, IFN-α, IFN-β, IP-10, MCP-1, MIP-1α, MIP-1β, Rantes, Eotoxin, Eotoxin-3, CXCL5). This experiment was performed again with a cell wall fraction isolated from $B.$ $longum$ 35624 in both a viable and non-viable lyophilised material versus live culture and similar IP-10 suppression was observed after 24 hours. Furthermore, the cytoplasmic fractions did not have any of this activity during the 24 hours of the assay (FIG. 2($f$)).

Figure 3A:
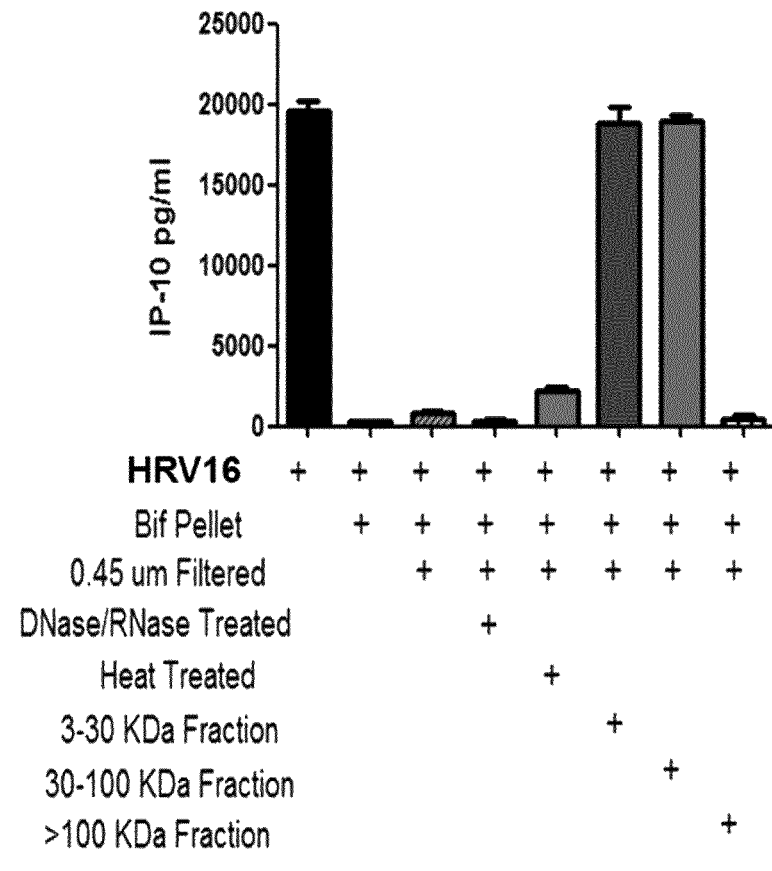
FIG. 3(*a*) is a bar chart of the IP-10 response to human rhinovirus (HRV16), in the presence of a range of cell wall fractions (Bif P, Bif P HT, Bif 0.45 μM, Bif 0.45 μM HT, Bif 0.45 μM <3 kDa, Bif 0.45 μM 3-30 kDa, Bif 0.45 μM >100 kDa) from strain 41003.
Figure 3B:
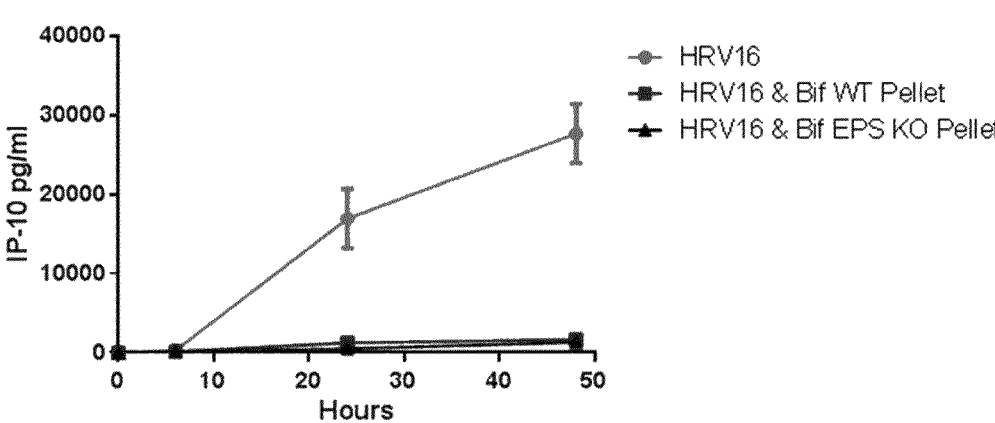

MDDCs were stimulated with HRV16 (MOI) 25:1) for 24 h in cRPMI at 37° C., 5% CO2 following pre-treatment (1 h) with different cell wall fractions (30 mg/ml) (Bif P) or just HRV16 alone. (Bif P, These cell wall fractions were heated to 80° C. (Bif P HT), or nuclease treated Bif P nuclease) or filtered through a 0.45 μm cut off Bif 0.45 μM or size exclusion filtered (Bif 0.45 μM HT, Bif 0.45 μM <3 kDa, Bif 0.45 μM 3-30 kDa, Bif 0.45 μM >100 kDa). The IP-10 suppression activity remained following heat treatment at 80° C., demonstrating that the activity was not DNA or RNA mediated (nuclease digestion did not alter the effect) and was associated with a >100 kDa fraction following filtration at 0.45 μm to remove all intact cells (FIG. 3$a$) MDDCs were stimulated with HRV16 (MOI) 25:1) for 24 h in cRPMI at 37° C., 5% CO2 following pre-treatment (1 h) with different cell wall fractions or just HRV16 alone. These cell wall fractions were isolated from $B.$ $longum$ 35624 or a genetically modified version of $B.$ $longum$ 35624 missing Exopolysaccharide (EPS). The IP-10 suppression activity was not related to EPS present in the cell wall material (FIG. 3($b$)).

Figure 4:
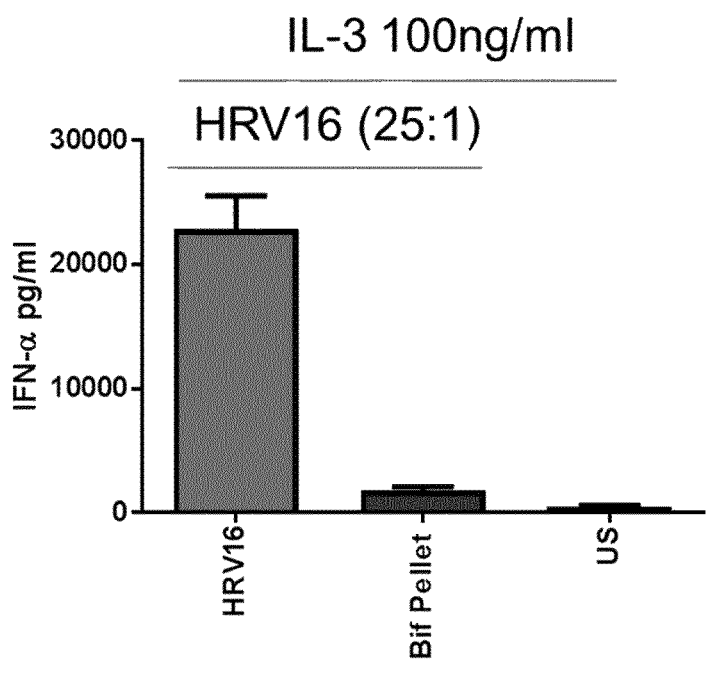
FIG. 4 is a graph of the IFN-α, response to human rhinovirus (HRV16) in the presence of a cell wall fraction (Bif pellet) from strain 41003 in Plasmacytoid Dendritic cells.

A particular class of DC's, plasmacytoid dendritic cells (pDCs), are prominent cells of antiviral immunity in that they are the biggest producers of IFN-α and they exhibit pro-inflammatory or tolerogenic functions depending on the environment to which they are exposed. pDCs have recently been shown to be detrimental in asthma, particularly after viral infection (Chairakaki et al 2017). Human pDCs were isolated from peripheral blood and the IFN-α response to RV was monitored. Human Plasmacytoid Dendritic Cells (pDCs) were isolated using the Diamond Plasmacytoid Dendritic Cell Isolation Kit II (Miltenyi Biotec) and cultured with IL-3 100 ng/ml (PeproTech). pDCs were stimulated with HRV16 (MOI) 25:1) for 24 h in cRPMI at 37° C., 5% CO2 following pre-treatment (1 h) with cell wall fractions from $B.$ $longum$ 35624 (75 mg/ml) or just HRV16 alone. IFN-α secretion was examined by Quantitine ELISA (R&D systems). Interestingly, the IFN-α response to RV was attenuated by the cell wall pellet fraction (FIG. 4). This effect of a bacterial component on IFN-α has not been shown before in the literature.

Figure 5:
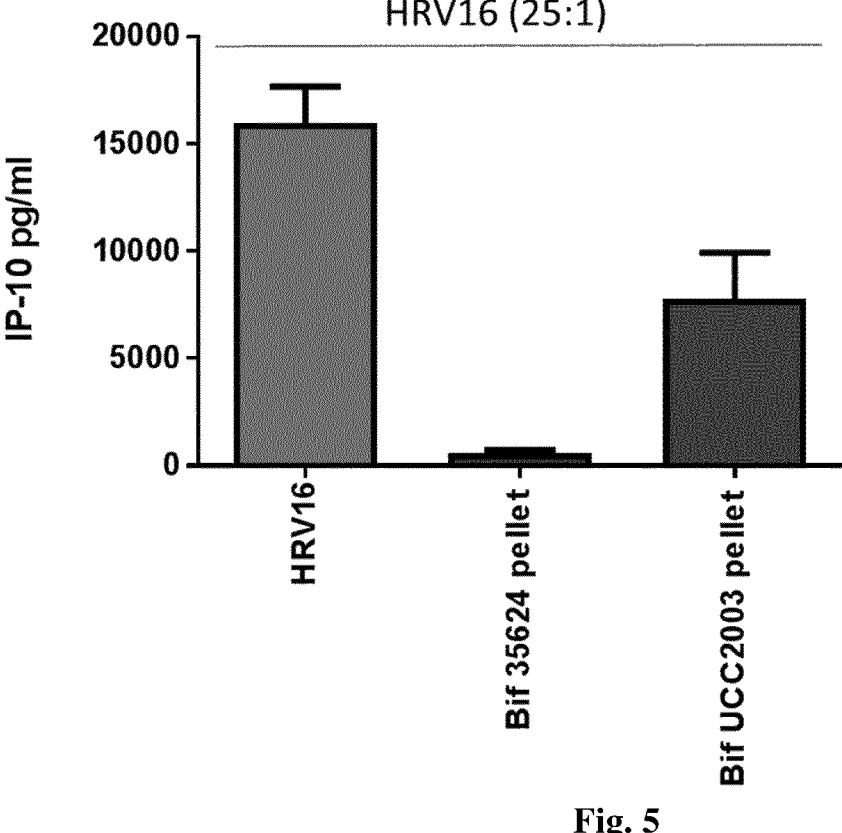
FIG. 5 is a bar chart of the IP-10 response to human rhinovirus (HRV16) compared to unstimulated (US) in the presence of a cell wall fraction from strain UCC2003 compared to a cell wall fraction from strain 41003 (Bif 35624® pellet) in Monocyte Derived Dendritic cells.

Example 3: Not all Cell Wall Fractions from Bifidobacteria Species have the Same Effect Cell wall fraction from another Bifidobacteria, Bifidobacteria $breve$ (Bif UCC2003) was also tested using the methodology described in example 2 and did not show similar significant effects. The Bif UCC2003 fraction reduced IP-10 production following viral stimulation but not to the same extent as the $B.$ $longum$ 35624 cell wall fraction during a 24 hours assay (FIG. 5).

Additionally, within the inflamed mucosa, it is not just the virus itself that induces IP-10 secretion; other cytokines can also induce IP-10 production. Cytokines such as IFN-γ, IFN-β, and IFN-λ are all produced as part of the primary anti-viral host response. IFN-γ and IFN-β in particular are potent inducers of IP-10. We examined the effect of the cell wall fraction on secretion of IP-10 in response to IFN-γ, IFN-β, and IFN-λ (FIG. 6). MDDCs were stimulated with either IFN-γ (100 ng/ml), or IFN-λ (200 ng/ml) or IFN-β (200 ng/ml) for 24 h in cRPMI at 37° C., 5% CO2 following pre-treatment (1 h) with cell wall fractions (30 mg/ml) or just IFN-γ, IFN-β, IFN-λ alone. The $B.$ $longum$ 35624 cell wall pellet fraction suppressed IP-10 secretion to all three stimuli, while the Bif UCC2003 cell wall pellet fraction did not reduce IP-10 secretion to any of the three cytokine stimuli.

Example 4: The Cell Wall Fraction from *B. longum* 35624 Strain has an Additional Beneficial Effect in Bronchial Epithelial Cells with Contributes to the Early Reduction of the Virus Bronchial epithelial cells are one of the main cell types in which viral replication occurs. In these cells it is important to support anti-viral defence mechanisms as an early host defence against disease. It is important to limit immune cell over-activation to prevent tissue damage. We cultured human bronchial epithelial in air-liquid interface (ALI) cultures and examined the influence of the cell wall fraction from 35624 on viral replication and cytokine secretion.

Primary human bronchial epithelial cells (Lonza) were cultured as monolayers in Bronchial Epithelial Cell Growth Medium (BEGM (Lonza) containing Bronchial Epithelial Basal Medium plus all the bullet-kit singlequots at 37° C. in a humidified atmosphere at 5% CO2. Medium was changed every second day. Cells were seeded at a density of 75,000 cells in a 6.5-mm-diameter polyester membrane with a pore size of 0.4 mm (Corning Costar) in BEGM medium. Once confluent, the medium in the apical compartment was removed and the medium in the basal compartment was substituted with ALI medium (Dulbecco modified Eagle medium [Gibco-BRL, Invitrogen] mixed 1:1 with BEGM supplemented with all-trans retinoic acid (ATRA) 50 nM to allow the cells to differentiate as air liquid interface (ALI) cultures.

ALI culture cells were exposed to cell wall fractions from *B. longum* 35624 30 mg/ml apically for 4 hours. The apical surface was washed twice with PBS all remaining liquid removed. The ALI culture cells were allowed to settle for 2 hours and then were stimulated with HRV16 (Virapur) (MOI 30:1) apically for 2 hours. The apical surface was washed twice with PBS all remaining liquid removed and left for 24 hours. Epithelial cell viral titer was quantified using a PCRmax qPCR kit for HRV16, according to manufacturer's instructions. Supernatant IFN-$\lambda$1 and IP-10 levels were quantified using a Bio-Plex kit (Bio-Rad) as per the manufacturer's instructions.

Figure 7:
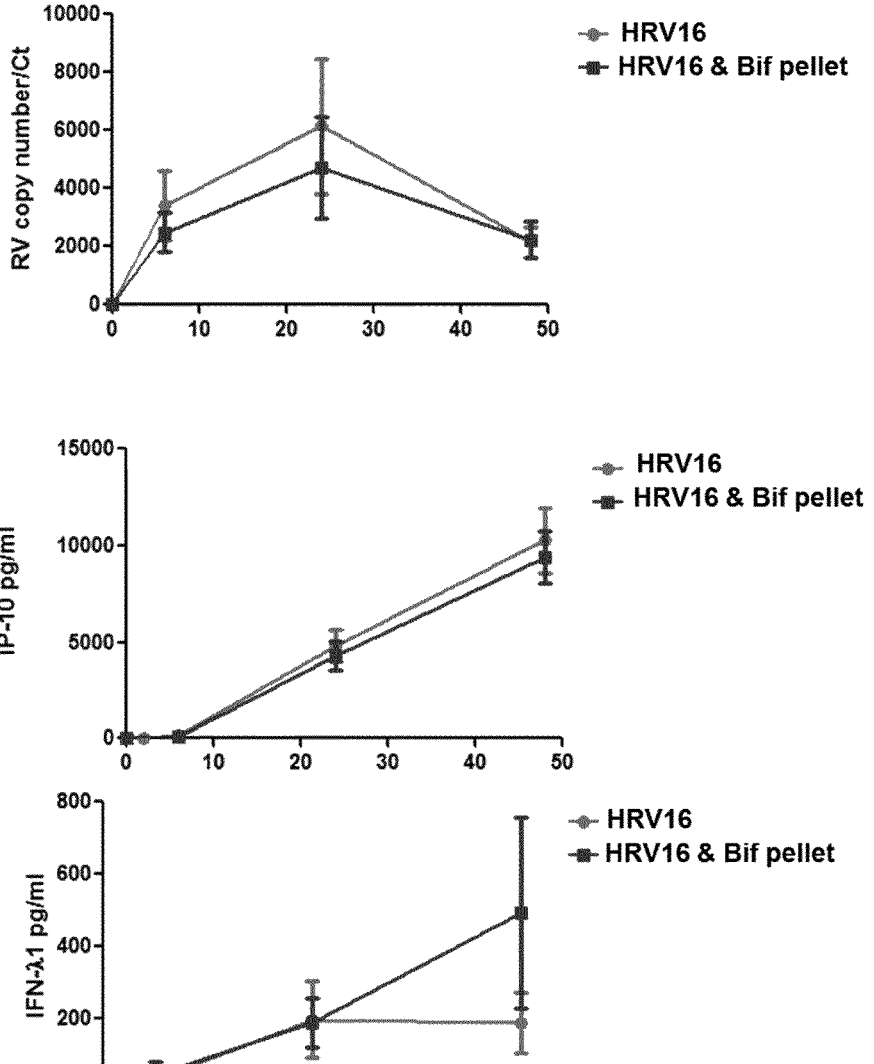
FIG. 7 are a series of graphs of viral replication and cytokine secretion in bronchial epithelial in an air liquid interface (ALI) cells response to human rhinovirus and human rhinovirus in the presence of a cell wall fraction (Bif 35624 pellet) from strain 41003.

The cell wall fraction reduced viral replication in bronchial epithelial cells over a 48 hour period, while having a minimal impact on IP-10 chemokine secretion (FIG. 7). This is the desired balanced response. Surprisingly, the secretion of the protective Type III IFN-$\lambda$ by bronchial epithelial cells increased over time, while not affecting of the Type 1 interferons. Significantly this was the case in cells cultured from healthy, asthma and COPD patients. Without the addition of cell wall fraction we would expect that Asthma and COPD patient cells to have a reduced interferon response which is part of the pathology for viral induced exacerbations. Therefore, addition of the cell wall pellet was protective for Asthma and COPD patient cells.

Example 5: The 35624 Cell Fraction Induces a Further Beneficial Cellular Cascade within the Host which Further Reduces the Detrimental Effect of Viral Infections in Asthma Once dendritic cells become activated, they induce T-cell activation and polarization. This activation can be beneficial or detrimental to the host depending on the type of signal that has been received from the dendritic cell. We co-incubated dendritic cells and autologous T cells following dendritic cell exposure to RV or exposure to RV with the cell wall pellet fraction from *B. longum* 35624. MDDCs were stimulated for 9 hours with HRV16 (MOI 25:1) and/or bacterial fractions and then washed and co-cultured with CD4+ or CD8 T cells from autologous donor at a ratio of 1:10 in AIM-V media (Life Technologies, 12055091). After 5 days cells were removed from culture from some of the wells and stained for CD4, CD25, Foxp3, T-bet and Ror-$\gamma$t expression using flow cytometry (eBioscience, San Diego). Cytokine concentrations in the supernatant were measured using the BioPlex assay (Biororad). The cell wall pellet fraction did not alter the induction of CD25+Foxp3+ regulatory T cells as these cells are independently induced by the presence of the rhinovirus. The *B. longum* 35624 cell wall fraction (FIG. 8) augmented IL-10 and IL-22 secretion which is a protective response which works to help clear infection and repair the lung in the host.

Figure 8:
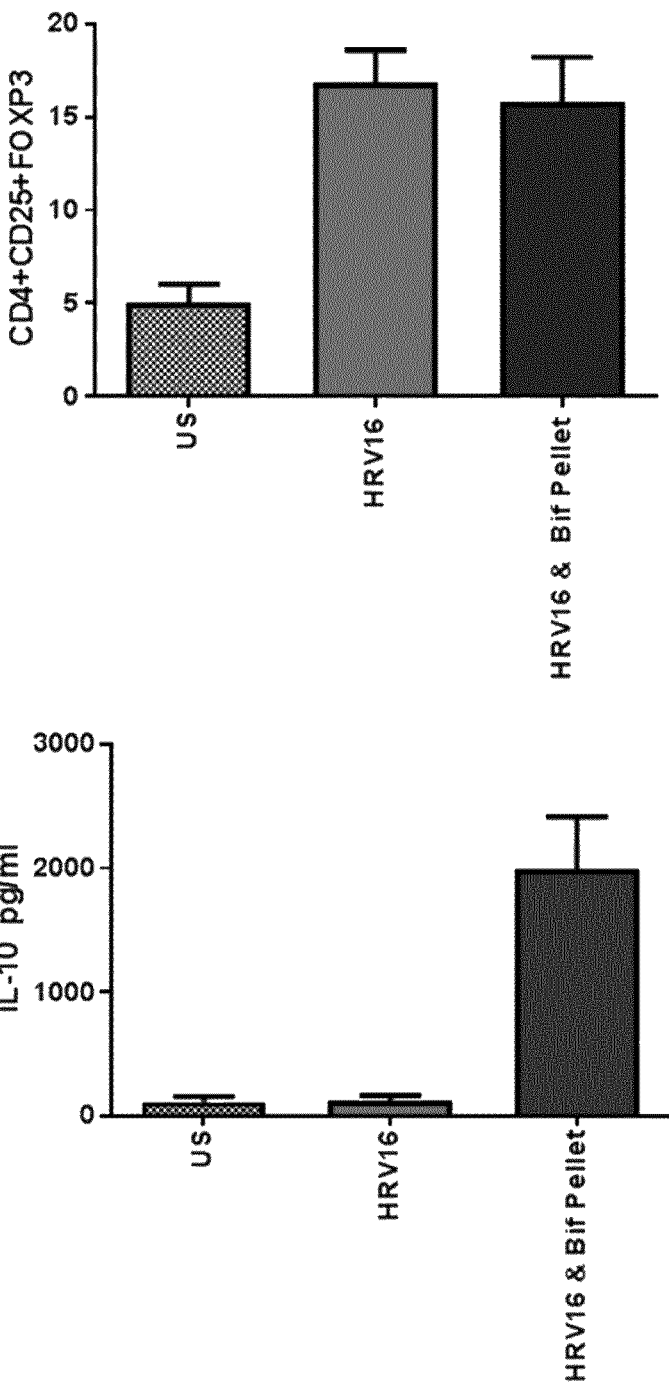
FIG. 8 are a series of bar charts of the induction of regulatory T-cells, TH1, TH2, TH17 cells in response to exposure to human rhinovirus (HRV) and rhinovirus with fractions (Bif 35,624 pellet) from strain 41003.
Figure 8:
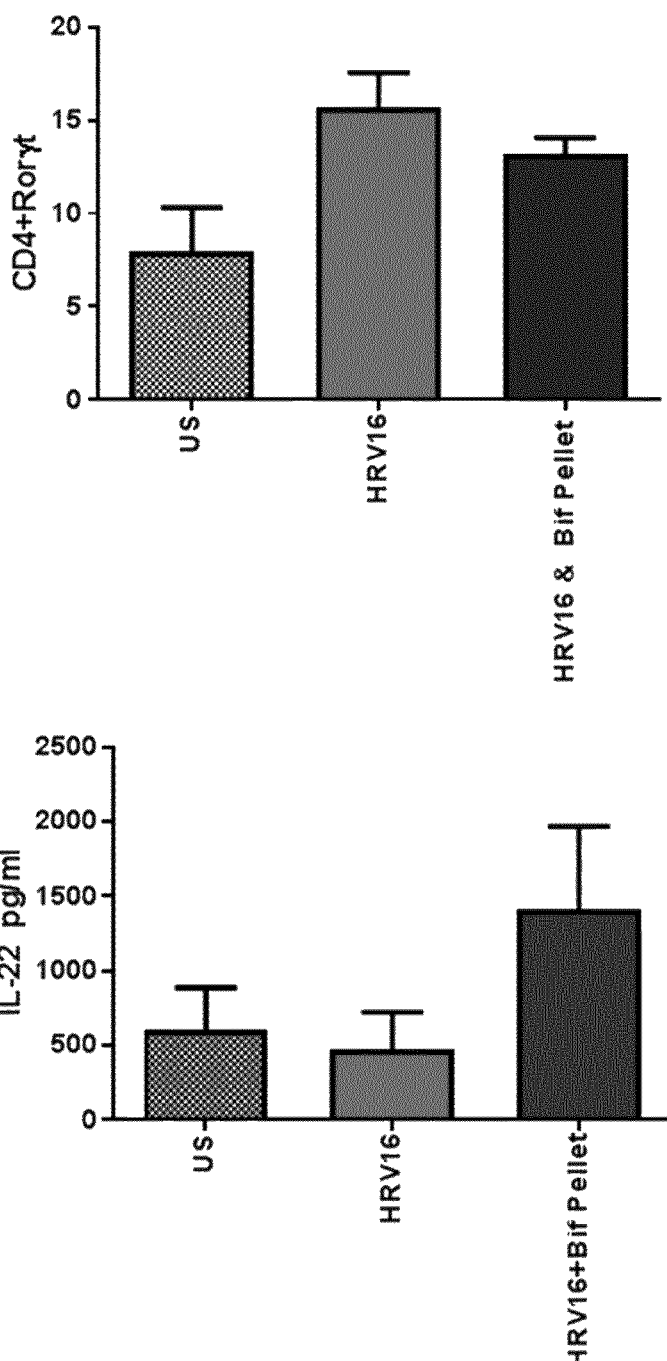
Figure 8:
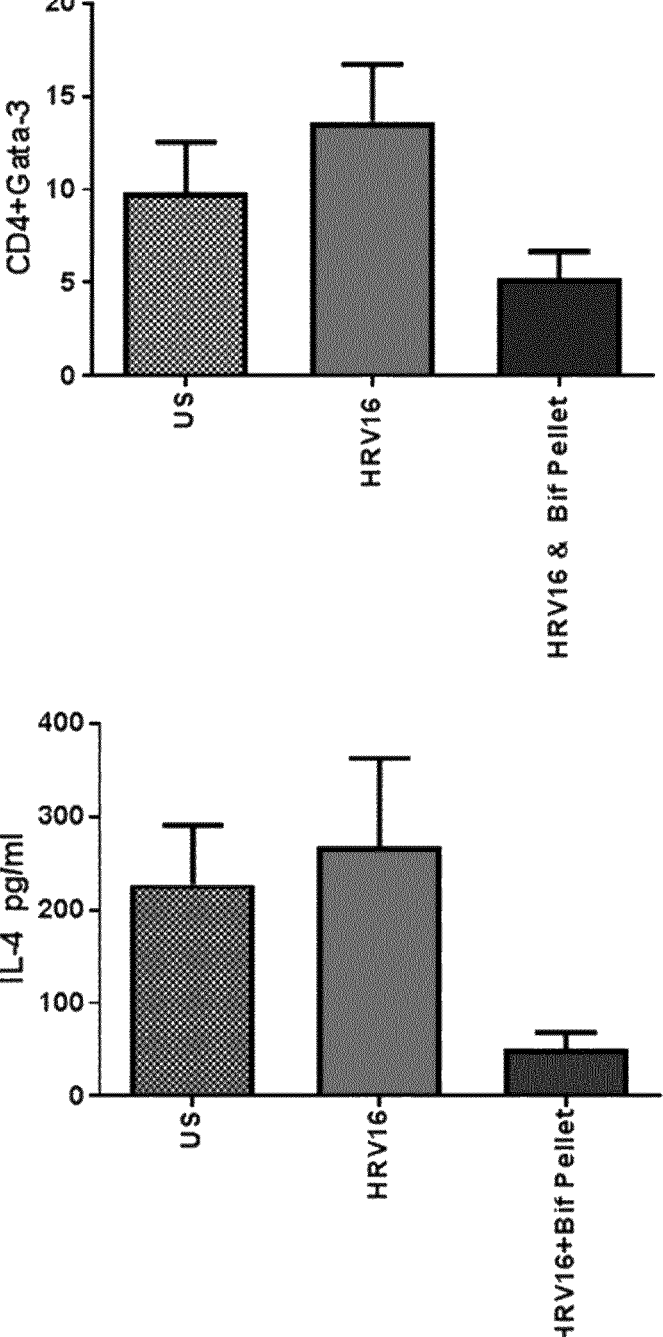
Figure 8:
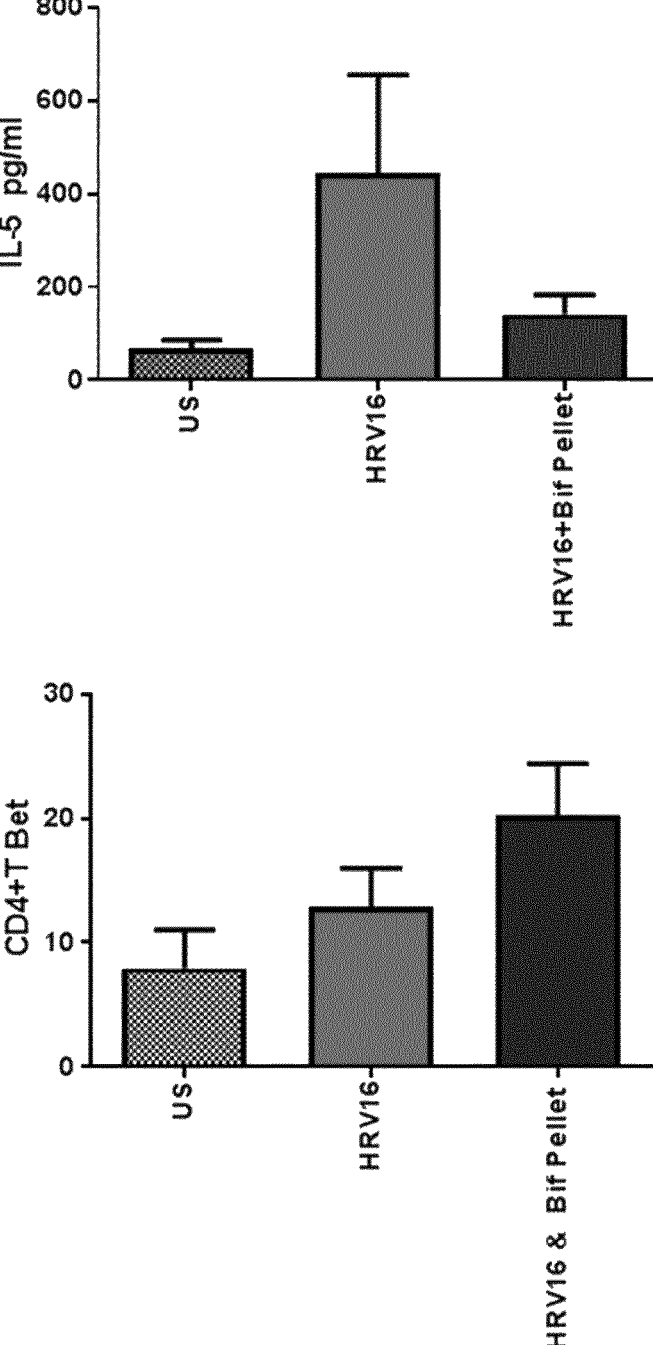
Figure 8:
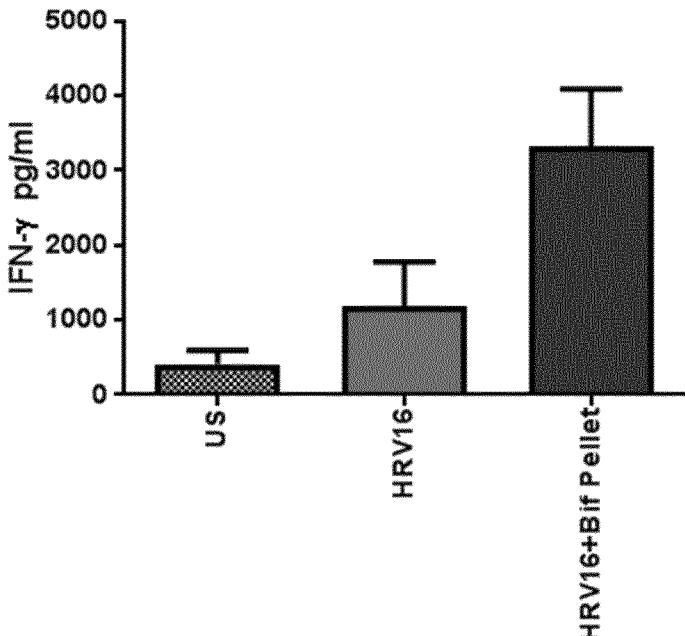

In addition, the cell wall fraction supported T-bet+ TH1 lymphocyte development and IFN-$\gamma$ secretion, and reduced GATA-3+ TH2 lymphocyte polarization. Th2 polarizing cytokines IL-4 and IL-5 were also decreased (FIG. 8). This dampening of the TH2 response is supportive of a protective response in asthma.

Example 6: Cell Wall Fraction Efficacy in In Vivo Models of Influenza (Spanish Flu)

We tested the efficacy of the cell wall fraction in preclinical models. RV murine models are not considered to be good surrogates of human infection as mice do not have ICAM which is the receptor for major group rhinoviruses to enter the cell therefore we utilized a lethal influenza model in mice, which is considered a better model (Bartlett et al 2015). The H1N1 influenza strain A/PR8/34 (100 PFU/50 ul) was used to infect mice. The *B. longum* 35624 cell wall fraction (150 mg/ml) was administered intranasally at −2 hours, +1 day, +3 days and +5 days following viral infection.

Figure 43:
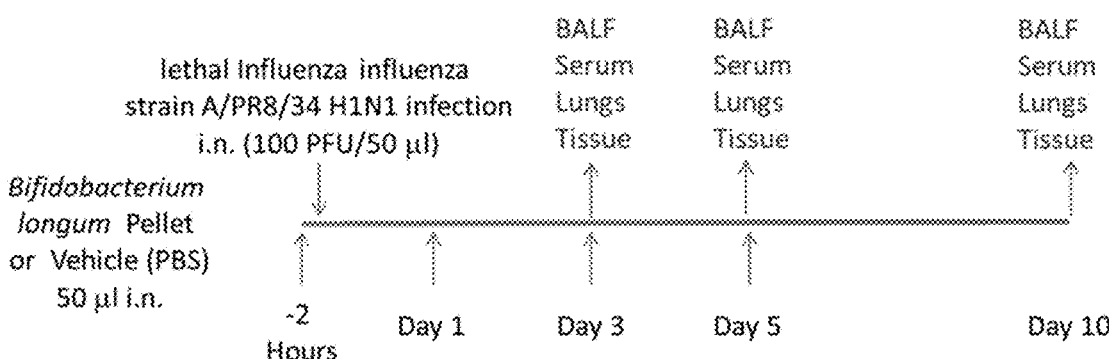
FIG. 43 is a graph of cell wall fraction efficacy in in vivo models of influenza.

FIG. 43 shows results for −2 h, day 1, 3 and 5 Administration of vehicle control (Group 1) and *B. longum* 35624 cell wall fraction (Group 2) per nasal (in 50 µl volume).

Day 0 Administration of a dose of lethal influenza (PR8) per nasal (Group 1-3).

Day 0-10: Monitoring of animals for morbidity (weight, temperature and clinical score, Group 1-2).

Day 3, 5 and 10: 5 animals per group are sacrificed for terminal bleed, organ removal and analysis on each day. Day 3 (Group 1 and 2), day 5 (Group 1-3) and day 10 (Group 1 and 2).

Day 3, 5 and 10: Isolation of BAL fluid for the measurement of cytokines and markers of lung damage. Collection of the lung tissue for the quantification of viral titre in the lung by quantitative PCR (half of all lung lobes).

Measurement of Viral Titre in Lung Tissue.

Lung lobes isolated were prepared for the quantification of viral load in lung tissue by quantitative PCR. RNA was prepared with TRI Reagent (Molecular Research Center) and then treated with DNase (Invitrogen) to avoid genomic DNA contamination before RNA was converted to cDNA by reverse transcription using SuperScript III (Invitrogen). cDNA was quantified by real-time PCR (iCycler; Bio-Rad) using SYBR Green (Stratagene) and samples were normalized with GAPDH expression levels. Primers sequences (forward and reverse, respectively) used were influenza PR8

M protein, 5'-GGACTGCAGCGTAGACGCTT-3' (SEQ ID No. 1) and 5'CATCCTGTATATGAGGCCCAT-3' (SEQ ID No. 2).

Groups (1-3):

1. Treatment with vehicle control.
2. Treatment with *B. longum* 35624 cell wall fraction.
3. Untreated control Group (Influenza infection only).

Number of mice per group (Group 1 and 2)=15

Number of mice per group (Group 3)=5

This exact experiment was repeated with multiple doses of *B. longum* 35624 cell wall fraction Groups (1-7) for the Dose Response Experiment:

1. Treatment with vehicle control.
2. Treatment with *B. longum* 35624 cell wall fraction (150 mg/ml).
3. Treatment with *B. longum* 35624 cell wall fraction (1/10 diluted).
4. Treatment with *B. longum* 35624 cell wall fraction (1/30 diluted
5. Treatment with *B. longum* 35624 cell wall fraction (1/1'00 diluted).
6. Treatment with *B. longum* 35624 cell wall fraction (1/10'00 diluted).
7. Untreated control Group (Influenza infection only).

Figure 9A:
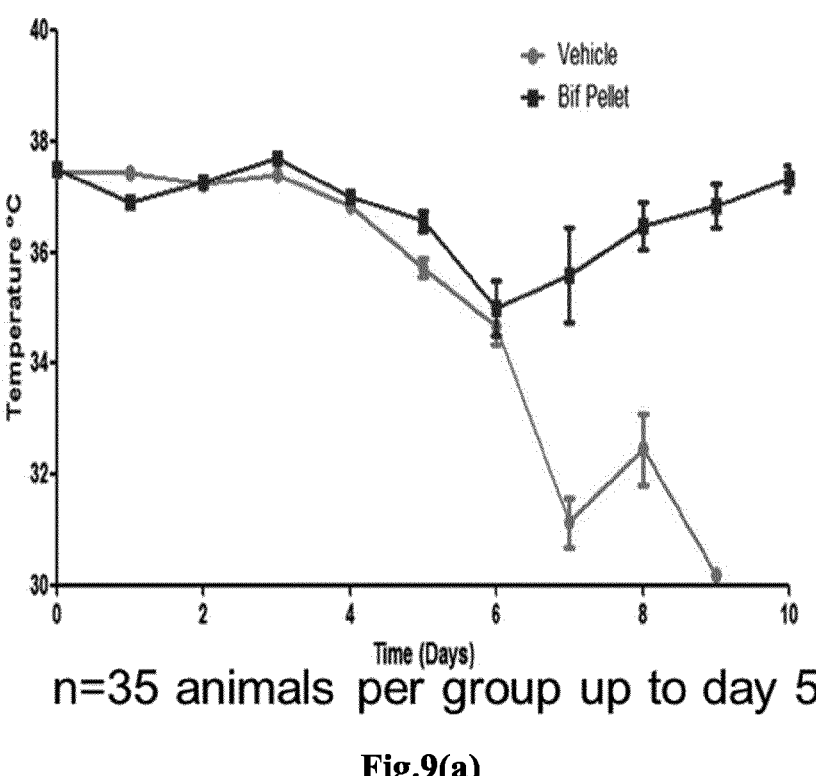
FIG. 9(*a*) is a graph of morbidity over a time period post infection with the cell wall fraction (Bif pellet) of strain 41003.
Figure 9B:
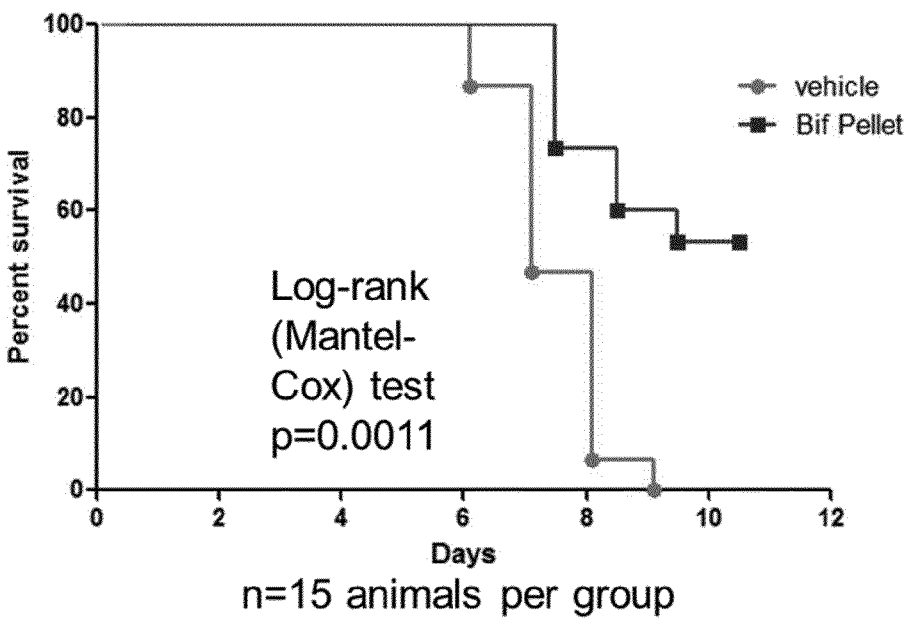

Administration of the *B. longum* 35624 cell wall fraction protected the mice. Morbidity and Mortality due to influenza infection was reduced (FIG. 9). In addition, viral titre was reduced at all time points measured and in dose dependent manner in the lung in the *B. longum* 35624 cell wall fraction group compared to the vehicle control (FIG. 10), which was associated with a reduced IP-10 and interferon-alpha and interferon-beta response and an enhanced early protective interferon-lambda and surfactant protein D response (FIG. 11). In addition, there was a potent induction of cytokines and chemokines at day 3 in cell wall treated animals. Measurements of Cytokines and Chemokine.

The concentrations of mouse IL-1p, IL-2, IL-4, IL-5, IL-6, IL-9, IL-10, IL-12p70, IL-12/IL-23p40, IL-13, IL 15, IL-16, IL-17A, IL-17A/F, IL-17C, IL-17E, IL-17F, IL-21, IL-22, IL-23, IL-30, IL-31, IL-33, IP-10, MIP3α, MIP-2, MIP-1β, MIP-1α, MCP-1, KC/GRO, TNF-α, VEGF, EPO, GM-CSF, IFN-γ in both serum and BAL fluid were measured using a commercial U-PLEX Biomarker Group 1 Mouse 35-Plex (MesoScale Discovery) platform following the manufacturers' instructions; mouse IL-28 (IFN-λ 2/3), mouse G-CSF, mouse TRAIL, mouse AREG were detected using ELISA kits (RayBiotech, Inc.); Oncostatin M and mouse surfactant protein D (SPD) were measured using Quantikine kits from R&D Systems following the manufacturer's instructions. Mouse IFN-α was measured in serum and BAL fluid by mouse IFN alpha platinum ELISA (ThermoFisher Scientific) Serum and BAL fluid levels of mouse interferon-β (IFN-β) were measured using VeriKine Mouse Interferon Beta HS ELISA Kits (PBL Assay Science).

Figure 12:
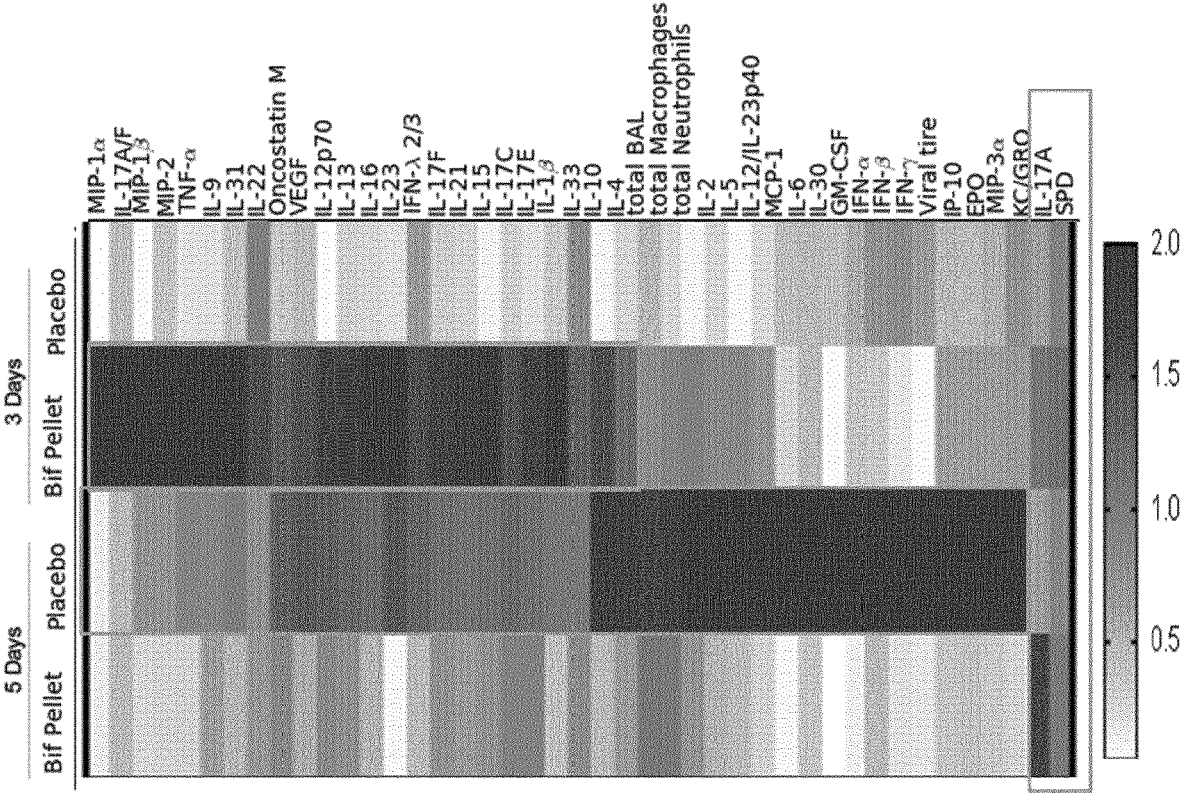
FIG. 12 shows a heat map of different protein biomarkers measured in the BALF in responses to a cell wall fraction (Bif pellet) from strain 41003 (35624®) following viral.

The early immune response contributed to the enhanced viral clearance seen in the cell wall treated animals. By day 5 post-infection, this potent immune response was gone in the cell wall treated animals (FIG. 12).

While current antiviral therapy is effective in preventing infection, no current therapy can prevent or treat influenza-induced pulmonary immune pathology (cell damage). We tested the efficacy of the cell wall fraction to influence two markers of lung epithelial cell damage (lactate dehydrogenase (LDH), albumin).

Lung Damage Assessment.

Vascular leakage in BAL fluid was assessed using a mouse albumin ELISA Quantitation Set (Bethyl Laboratories, Inc., Montgomery, TX). To measure lung injury, lactose dehydrogenase (LDH) activity was measured using the LDH assay (Sigma-Aldrich). This assay was performed in a 96-well plate for 30 min according to the manufacturer's instructions and analysed using the MicroTek plate reader (Bio-Rad, Hercules, CA).

Mice which had been administered the cell wall fraction displayed significant reductions in markers for lung epithelial cell damage, but this was not shown in the vehicle control animals. (FIG. 13) These results indicate an elimination of the virus and immunopathology in the lung by day 5 after treatment, without excessive inflammation, a frequent characteristic of the host response to viral infection in compromised individuals. In contrast, placebo treated animals displayed a later response, greater range and longer duration of pro-inflammatory cytokine, chemokine and interferon activation resulting in more severe disease and mortality.

Example 7: Effect of the Cell Wall Fraction on Secondary Bacterial Infection Post Influenza Infection We tested the efficacy of the cell wall fraction in preclinical superinfection models.

Figure 44:
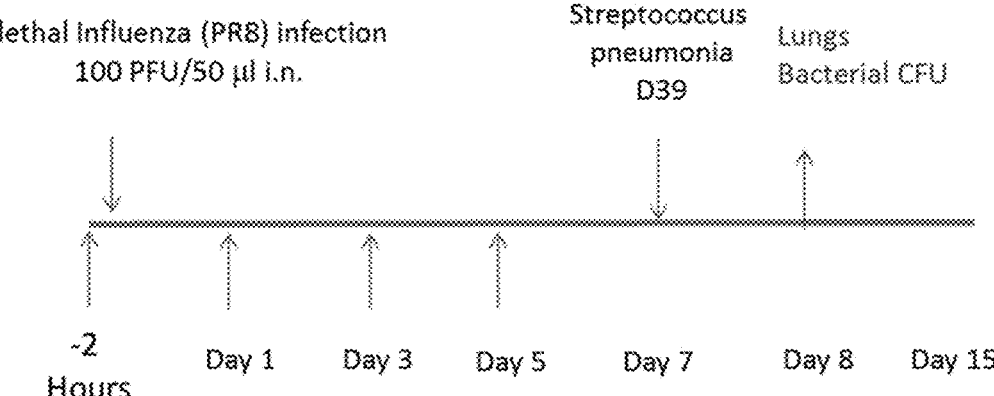
FIG. 44 is a graph of the effect of the cell wall fraction on secondary bacterial infection post influenza infection.

FIG. 44 shows results for 2 h, day 1, 3 and 5 Administration of vehicle control (Group 1) and *B. longum* 35624 cell wall fraction (150 mg/ml) (Group 2) per nasal (in 50 µl volume).

Day 0 Administration of a dose of lethal influenza (PR8) (100 PFU/50 l) per nasal (Group 1-3).

Day 7 Administration of a dose of *Streptococcus pneumonia* D39 (10' CFU/50 µl) per nasal (Group 1-3).

Day 0-15 Monitoring of animals for morbidity (weight, temperature and clinical score, Group 1-4).

Day 8: 5 animals per group are sacrificed for lung removal. Collection of the lung tissue for the quantification of *Streptococcus pneumonia* counts Groups 1—Vehicle+Influenza+*Streptococcus pneumonia*

Groups 2—*B. longum* 35624 cell wall fraction+Influenza+*Streptococcus pneumonia*

Group 3—Influenza+*Streptococcus pneumonia* (no treatment)

Group 4—Vehicle+*Streptococcus pneumonia* (No Influenza

The H1N1 influenza PR8 strain was used to infect mice followed by a secondary bacterial infection with *Streptococcus pneumonia* D39 at day 8. The *B. longum* 35624 cell wall fraction was administered intranasally at −2 hours, +1 day, +3 days and +5 days following viral infection. Again, administration of the cell wall fraction from the 35624 strain protected the mice.

Measurement of Bacteria Colonization in Lung Tissue.

Lung tissues were harvested, homogenized in 2 ml saline (gentle medimachine homogenization) and 25 ul of serial dilutions (10e-2, 10e-3, 10e-4 and 10e-5 dilutions) were plated on TSA plate (Tryptic soy agar, aseptic plates, BD-Brunschwig Tryptic soy agar, aseptic plates. Chemie Brunschwig AG, Basel, Switzerland. Catalogue number 254051). Following overnight incubation colonies were counted on plates with separate colonies detectable and CFU per ml solution were calculated.

Figure 14:
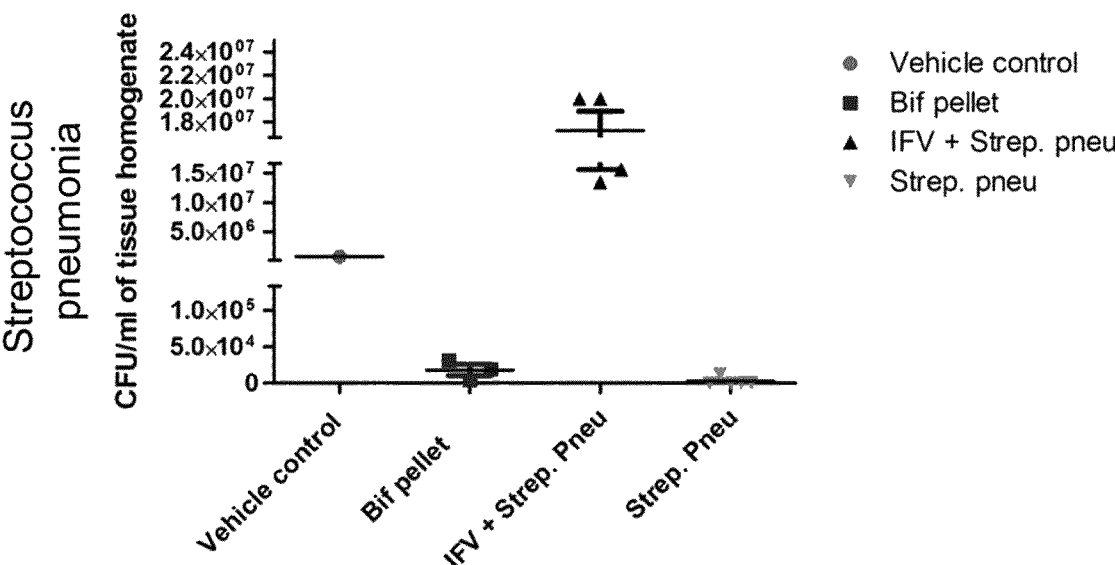
FIG. 14 is a graph of the measurement of bacterial load (CFU/ml) in lung tissue in responses to a cell wall fraction (Bif pellet) from strain 41003 following viral and subsequent bacterial infection.

Lung counts of *Streptococcus pneumonia* were reduced to the same levels as mice which who were not infected with influenza (FIG. 14).

Example 8: Therapeutic Effect of the Cell Wall Fraction on Influenza Infection Whereby Administration of the Cell Wall Fraction Occurs 1 Day after Infection with Influenza Virus)

Figure 45:
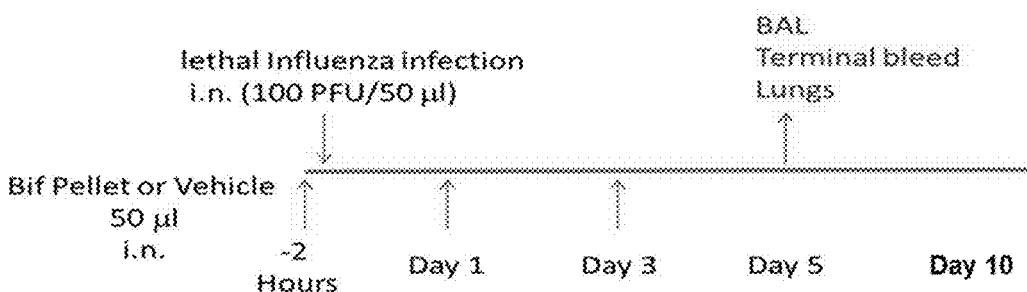
FIG. 45 is a graph of therapeutic effect of the cell wall fraction on influenza infection.

FIG. 45 shows results for Groups (1-4):

1. Treatment with vehicle control. Administration at −2 hr, day 1, day 3).
2. Treatment with *B. longum* 35624 cell wall fraction (150 mg/ml) Administration at −2 hr, day 1, day 3).
3. Treatment with *B. longum* 35624 cell wall fraction (150 mg/ml) Administration on day 1, day 3.
4. Untreated control Group (Influenza infection only).

Figure 15:
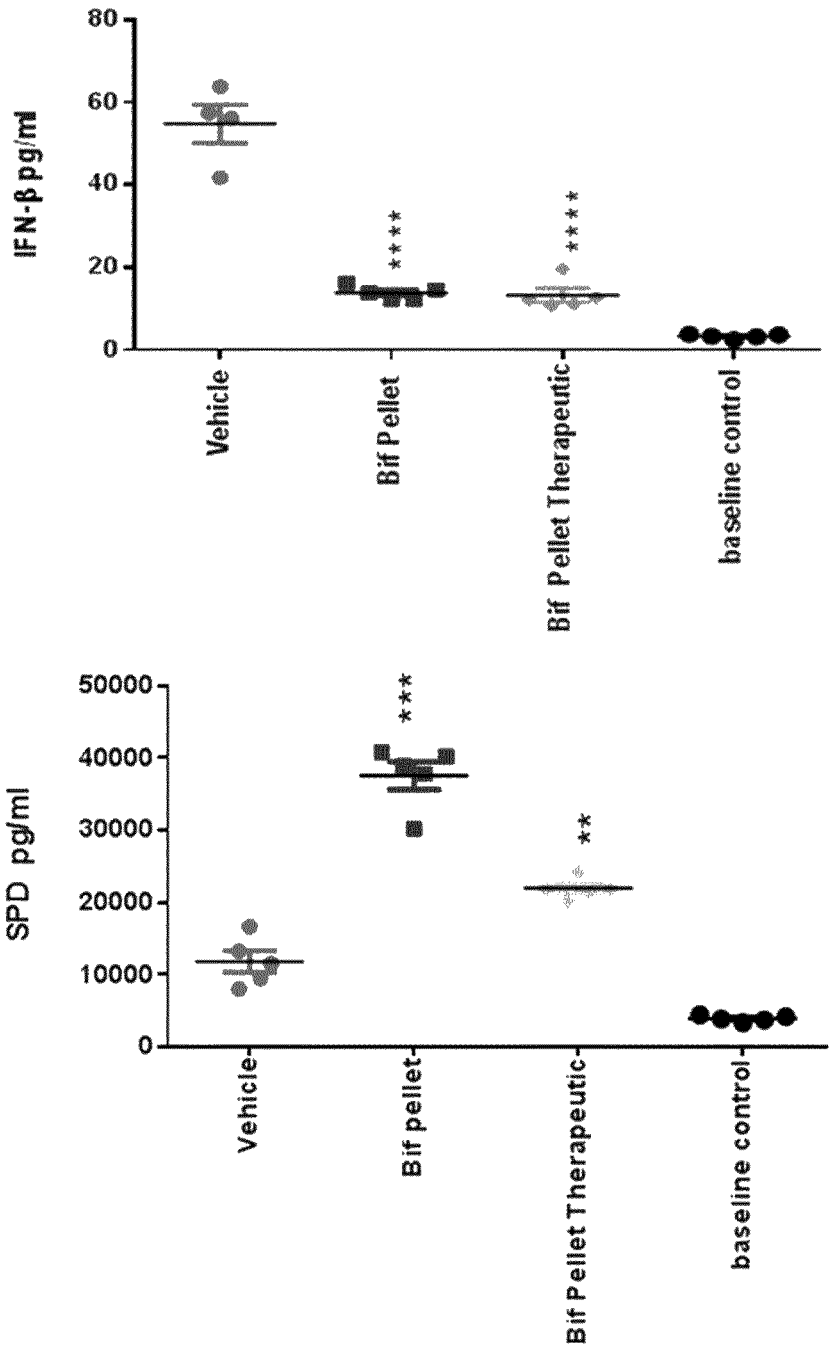
FIG. 15 is a graph of viral replication in the lung and a series of graphs of cytokine responses in the BALF in response to a cell wall fraction (Bif pellet) from strain 41003 administered therapeutically following viral infection.

We tested the efficacy of the cell wall fraction therapeutically in the H1N1 influenza PR8 strain infection model. The *B. longum* 35624 cell wall fraction was administered intranasal, +1 day, +3 days following viral infection. Surprisingly, the therapeutic administration of the *B. longum* 35624 cell wall fraction protected the mice by reducing the viral titre in the lung (FIG. 15). This reduction was associated with a reduced interferon-alpha and interferon-beta response in the BALF (FIG. 15). There was also an increase in the levels of surfactant protein D in the serum. Probiotic bacteria are generally fed prophylactically for weeks in advance leading to a priming of the innate immune system. By screening and identifying a novel cell wall fraction of an immunoregulatory microbe and delivering this fraction directly to the site of infection i.e. intranasally to the respiratory system we have been able to show not only a prophylactic response to viral infection but also a real therapeutic response. This is the first time this has ever been shown with a *Bifidobacterium*.

In summary, as illustrated in examples 2-8, we have shown that in cells that first experience viral infection (bronchial epithelia), where an enhanced Type III interferon response to stop viral replication is beneficial, addition of the cell wall fraction from 35624 causes this desired response. In other cells that are part of the later host immune system response (monocytes, DC's) the cell wall fraction blocks the excessive Type 1 interferon response that can lead to cell damage and secondary infection. This targeted effect has benefit in infections caused by influenza, the common cold (rhino virus) and RSV, viral exacerbation of chronic respiratory diseases such as asthma, COPD and ARDs in both children and adults and in obese individuals.

Cascade Response

Figure 16A:
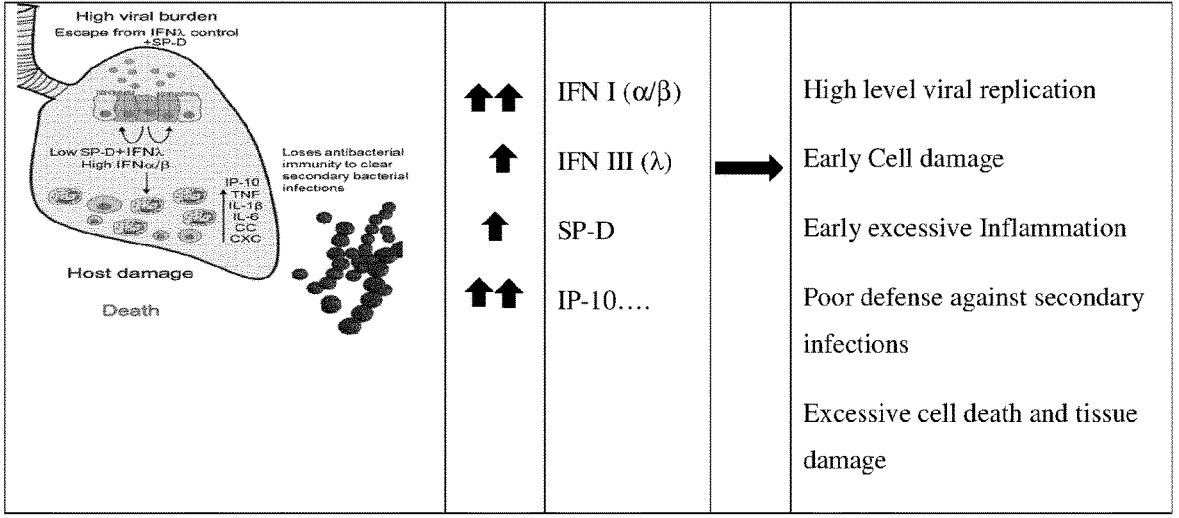
FIG. 16(*a*) is an illustration of cascade of abnormal response to a viral infection.
Figure 16B:
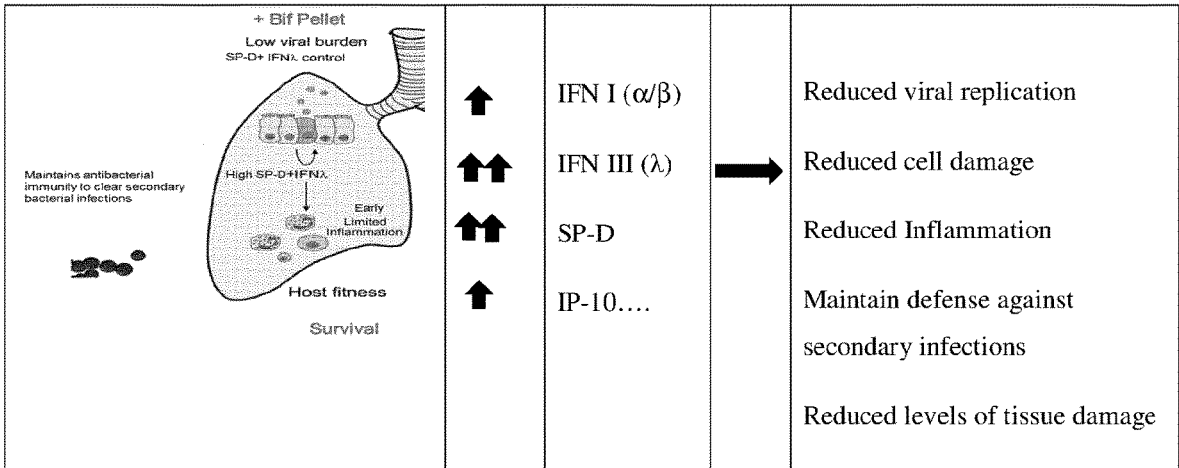

The cascade of abnormal response to viral infection is illustrated in FIG. 16(*a*).

The cascade of cell wall fraction mediated response to viral infection is illustrated in FIG. 16(*b*).

The main antiviral response is controlled by IFNs. The most well-defined type I IFNs are IFN-α and IFN-β. Most cell types produce IFN-β, whereas haematopoietic cells, particularly plasmacytoid dendritic cells, are the predominant producers of IFN-α (Ivashkiv and Donlin 2014). As mentioned previously, the Interferon type I responses, such as IFN-α and IFN-β has been shown to directly correlate with increased morbidity and mortality in models of influenza infection (Davidson et al, 2014). Type 1 IFNs can stimulate the production of IP-10 (also called CXCL-10) a chemokine which binds to CXCR3 where its primary function is a chemoattractant for Th1 cells. Lambda IFNs (IFNls, type III IFNs or IL-28 and IL-29) constitute a newer class of interferons that share homology, expression patterns, and antiviral functions with type I IFNs (Lazear et al., 2015b; Wack et al., 2015). They induce downstream signalling that appears remarkably similar to that of type I IFNs, driving the expression of ISGs and the induction of antiviral responses (Durbin et al, 2013; Mendoza et al, 2017). However, type III interferons play an important role in limiting pro-inflammatory responses or immunopathology.

IP-10 is elevated in the lungs on infection with influenzas virus (Ichikawa et al, 2013). Indeed, blocking IP-10 using monoclonal antibodies ameliorates virus induced lung injury (Wang et al, 2013). IP-10 is elevated in the lungs of ARDS patients and it has been shown to be an important factor in the ARDS pathology (Ichikawa et al, 2013).

SP-D has an important role in innate host defence against influenza by binding to mannose-rich glycans on the HA/NA glycoproteins of the virus (Hartshorn et al, 1997; Reading et al, 1997; Hartshorn et al, 2000). SP-D mediates a range of antiviral activities in vitro, including neutralization of virus infectivity and inhibition of the enzymatic activity of the viral NA, and SP-D-deficient mice were more susceptible to infection with highly glycosylated influenza viruses. (Hartshorn et al, 1997; Reading et al, 1997; Tecle et al, 2007; LeVine et al, 2001; Vigerust et al, 2007; Hawgood et al, 2004). SP-D enhances phagocytosis and pulmonary clearance of RSV (LeVine et al, 2004).

Secondary bacterial infections are a major issue following viral infection. Virus-bacterial co-infection is well recognized with influenza, rhinovirus and RSV. The major bacterial infections in the respiratory tract include *Streptococcus pneumoniae, Moraxella catarrhalis,* and *Haemophilus influenzae* but *Staphylococcus aureus* has been also shown to cause serious infections post viral infection. (Hewitt et al, 2016). Secondary bacterial infections occur most frequently at 5-10 days after primary viral infections, thus suggesting that a transient immunosuppression (the primary response) maybe responsible for the bacterial outgrowth. A mechanism proposed for a synergism between influenza and *S. pneumoniae* suggests that the antiviral type 1 IFN (IFN-α/p) response elicited by the primary influenza virus infection enhances the susceptibility of the host to secondary bacterial challenge via suppression of antibacterial immunity (Nakamura et al, 2011; Shahangian et al, 2009; Li et al, 2012). In contrast type III interferons such as IFN-λ can limit viral replication without inhibiting the clearance of the secondary bacterial infections which happens after IFN-α/β induction. It has been shown that the impact of attenuating IFN-λ signalling directly before bacterial challenge with an IFNLR1 Fc protein significantly increased bacterial burden in the lung compared with controls in animals (Rich et al, 2017). Furthermore, deficiency of SP-D was associated with enhanced colonisation and infection with *S. pneumoniae* of the upper and lower respiratory tract and earlier onset and longer persistence of bacteraemia. SP-D was shown to binds and agglutinates *Streptococcus pneumoniae* in vitro (a secondary bacterial infection agent that is a key problem in secondary exacerbations in asthma and COPD patients) (Jounblat et al, 2005).

The different conditions that are acutely affected by the dysregulated or aberrant immune response to viral infection are summarized as follows; Acute respiratory distress syndrome (ARDS), Asthma including childhood asthma, COPD, Obesity.

Acute respiratory distress syndrome (ARDS) affects a large number of people worldwide and is associated with a very high mortality rate (30-50%). Respiratory viral infections (e.g. influenza) are associated with ARDS.

Asthma is a chronic inflammatory disorder of the airways, usually associated with airway hyper-responsiveness and variable airflow.

Asthma is a chronic inflammatory disorder of the airways, usually associated with airway hyper-responsiveness and variable airflow obstruction that is often reversible spontaneously or during treatment (WHO, 2007). Approximately 80 to 85% of asthma exacerbations in children, adolescents, and less frequently adults are associated with viral upper respiratory tract viral infections, and rhinovirus (RV) accounts for ~60-70% of these virus-associated exacerbations. Viral infections are closely linked to wheezing illnesses in children of all ages. RSV is the main causative agent of bronchiolitis or croup, whereas rhinovirus (RV) is most commonly detected in wheezing children thereafter. Severe respiratory illness induced by either of these viruses is associated with subsequent development of asthma, and the risk is greatest for young children who wheeze with RV infections (Jartti and Gem, 2017).

Obesity is associated with dysregulated immune and inflammatory responses. The effect of obesity on the occurrence of asthma seems to be more prominent in women and non-allergic individuals, while there is a dose response effect of increasing body mass index (BMI) on asthma incidence. It is becoming increasingly evident that obesity is associated with a unique asthma phenotype that is characterized by more severe disease with variable response to conventional asthma therapies. In addition, obesity was identified as a risk factor for severe influenza during the 2009 influenza A (H1N1) pandemic and obese individuals have an impaired antiviral defence against respiratory viruses (Almond et al, 2013). Evidence suggests that it is not the virus itself but the nature of the immune response to RV that drives this damaging response (Steinke et al, 2016).

COPD is the third leading cause of death in the USA. In fact, COPD is the only major cause of death whose incidence is on the increase and is expected to be the third leading cause of death in the developed world by 2030 (exceeded only by heart disease and stroke). It results from inflammation induced damage of the airways causing chronic bronchitis and/or emphysema. A wider spectrum of viruses can induce exacerbations in COPD patients, but again it seems that it is not the virus, but the immune response to the virus that results in worsening of symptoms (Zhou et al, 2015).

*Bifidobacterium longum* 35624 (*B. longum* 35624) has been shown to reduce pro-inflammatory responses to infection within the gastrointestinal tract (O'Mahony C, et al., PLoS Pathogens 2008). It does not automatically follow that the whole strain would have beneficial effects in other human systems. Therefore, in addition to the cell wall fraction, the ability of the whole bacterial strain to modify the immune response to virus infection in vitro in human dendritic cells and bronchial epithelial; cells has now been investigated, with surprising results.

Example 9

Figure 17:
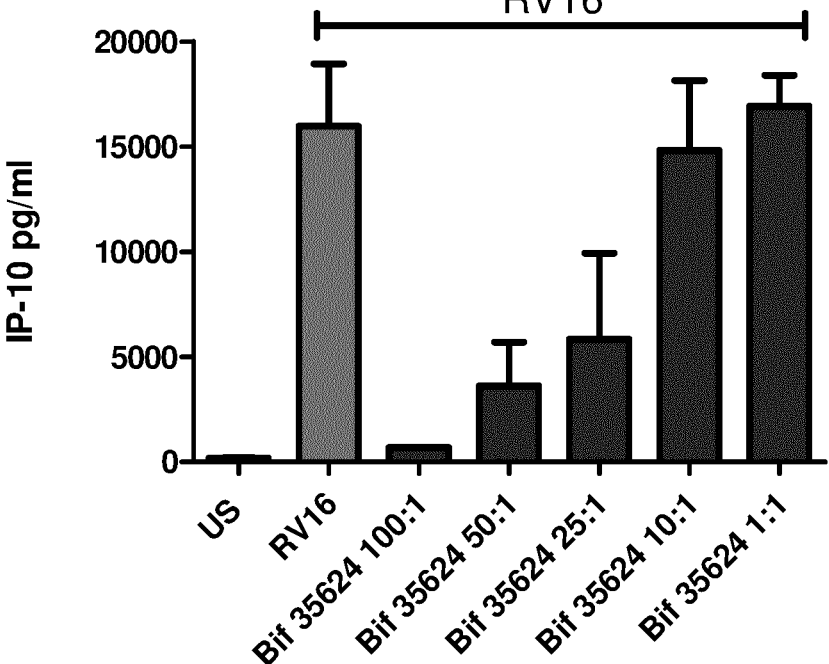
FIG. 17 is a bar chart of the IP-10 response to rhinovirus in the presence of strain 41003.

Dendritic cells (DCs) were generated following isolation of human CD14+ monocytes from peripheral blood and culture in GM-CSF and IL-4 for 5 days. DCs were exposed to rhinovirus (RV) and the IP-10 response to RV was monitored. Surprisingly, the IP-10 response to RV was attenuated by *B. longum* 35624 in a dose-dependent manner (FIG. 17). Equally surprising, was that co-incubation with *B. longum* 35624, particularly at lower doses, resulted in the enhancement of type III interferon responses (Interferon lambda) while Interferon alpha and beta responses were suppressed, similar to the IP-10 response (FIG. 18). This data shows that *B. longum* 35624 alters the immune response to RV in supporting a protective immune response while dampening the damaging responses.

Figure 19:
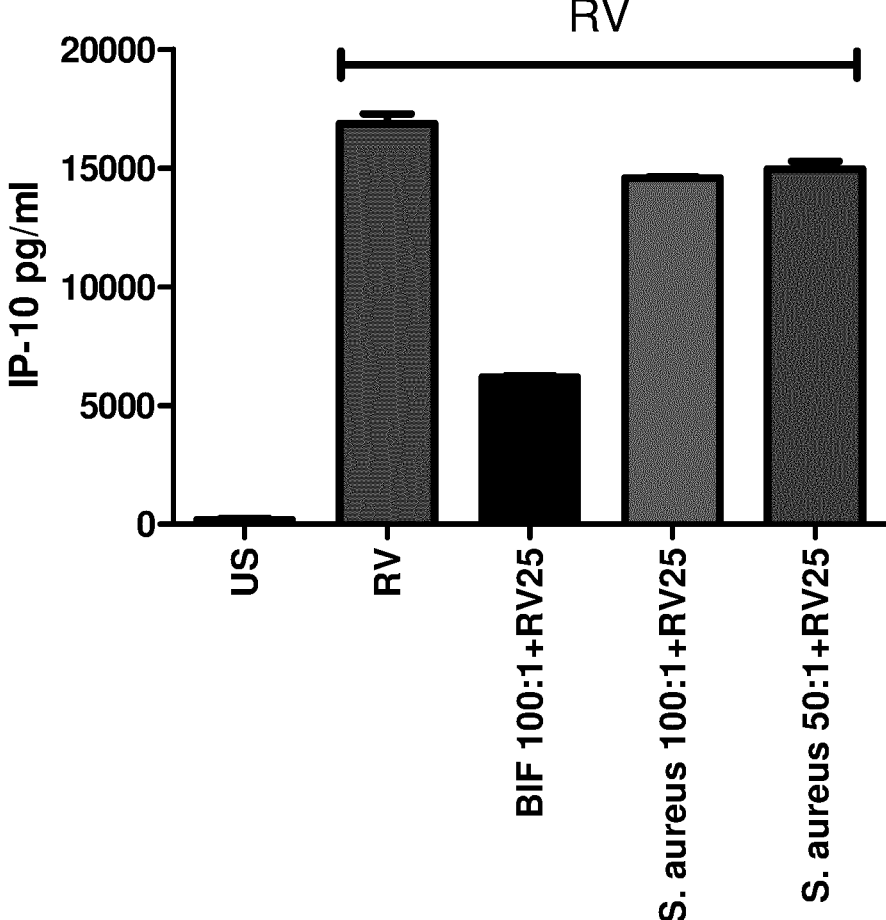
FIG. 19 is a bar chart comparing the IP-10 response to rhinovirus in the presence of strain 41003 (35624®) and an *S. aureus* strain.
Figure 20:
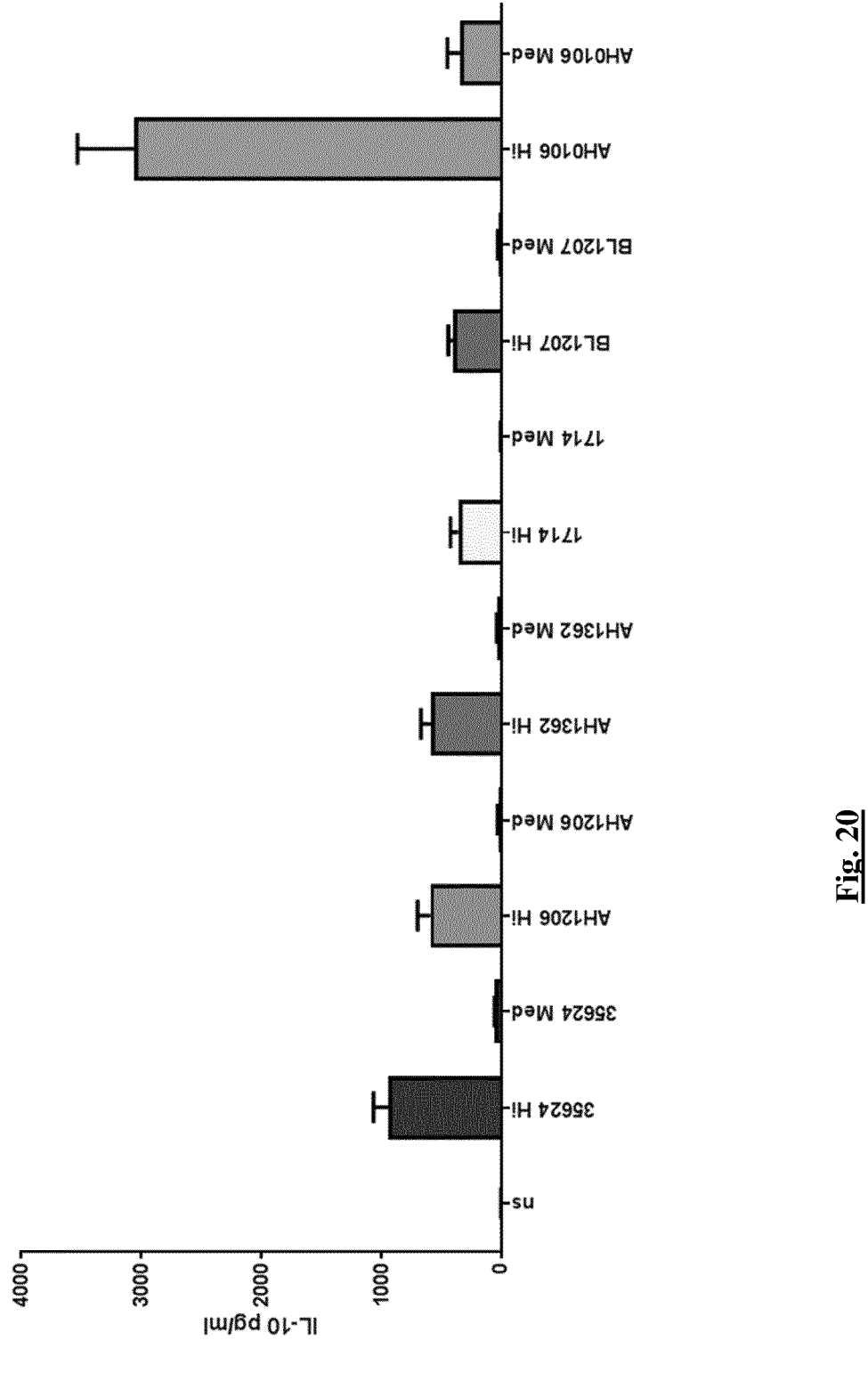
FIG. 20 are bar graphs showing the induction profile of IL-10 in PBMC and in MDDCs after in vitro stimulation with increasing concentrations (medium and high) of *B. longum* strains 35624, AH1206, AH1362, 1714, BL1207 and AH0106.
Figure 20:
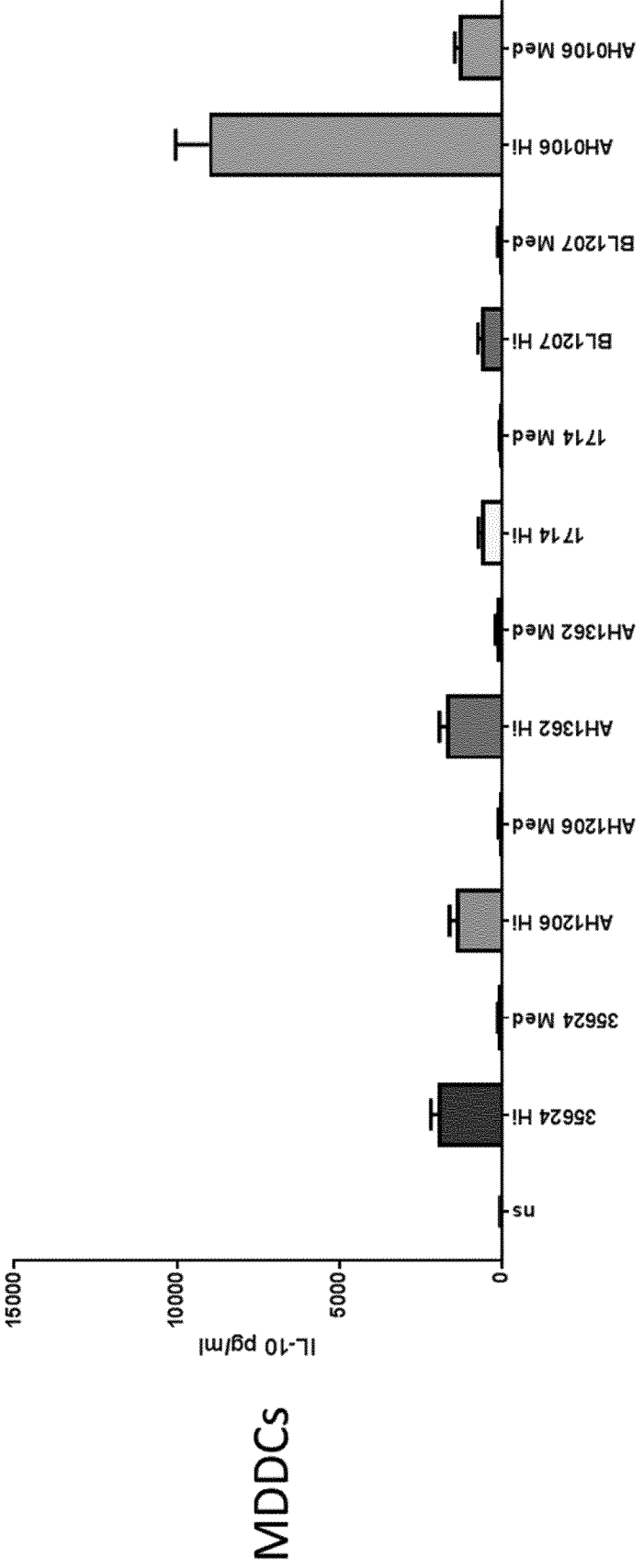
Figure 21:
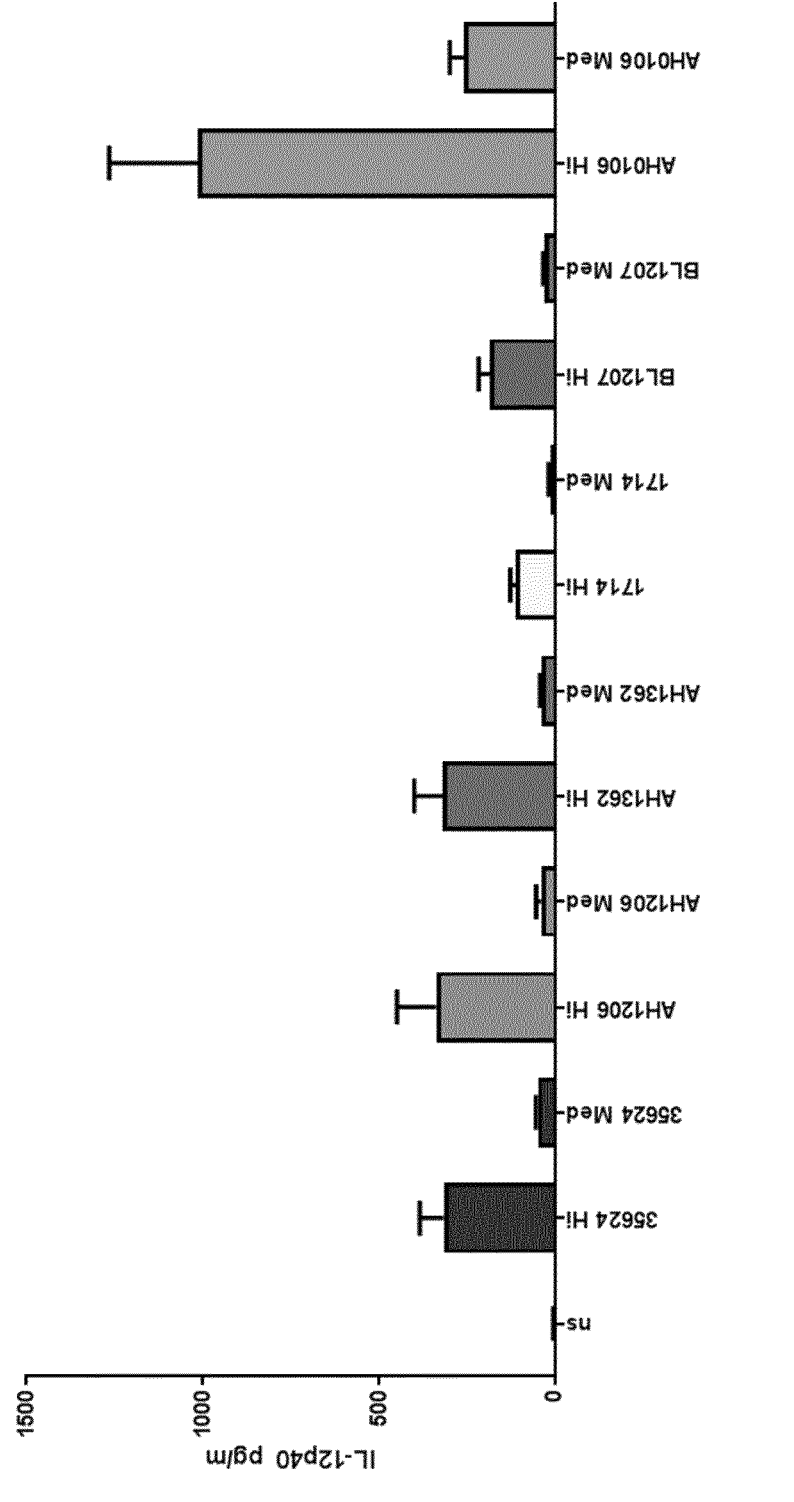
FIG. 21 are bar graphs showing the induction profile of IL-12p40 in PBMC and in MDDCs after in vitro stimulation with increasing concentrations (medium and high) of *B. longum* strains 35624, AH1206, AH1362, 1714, BL1207 and AH0106.
Figure 21:
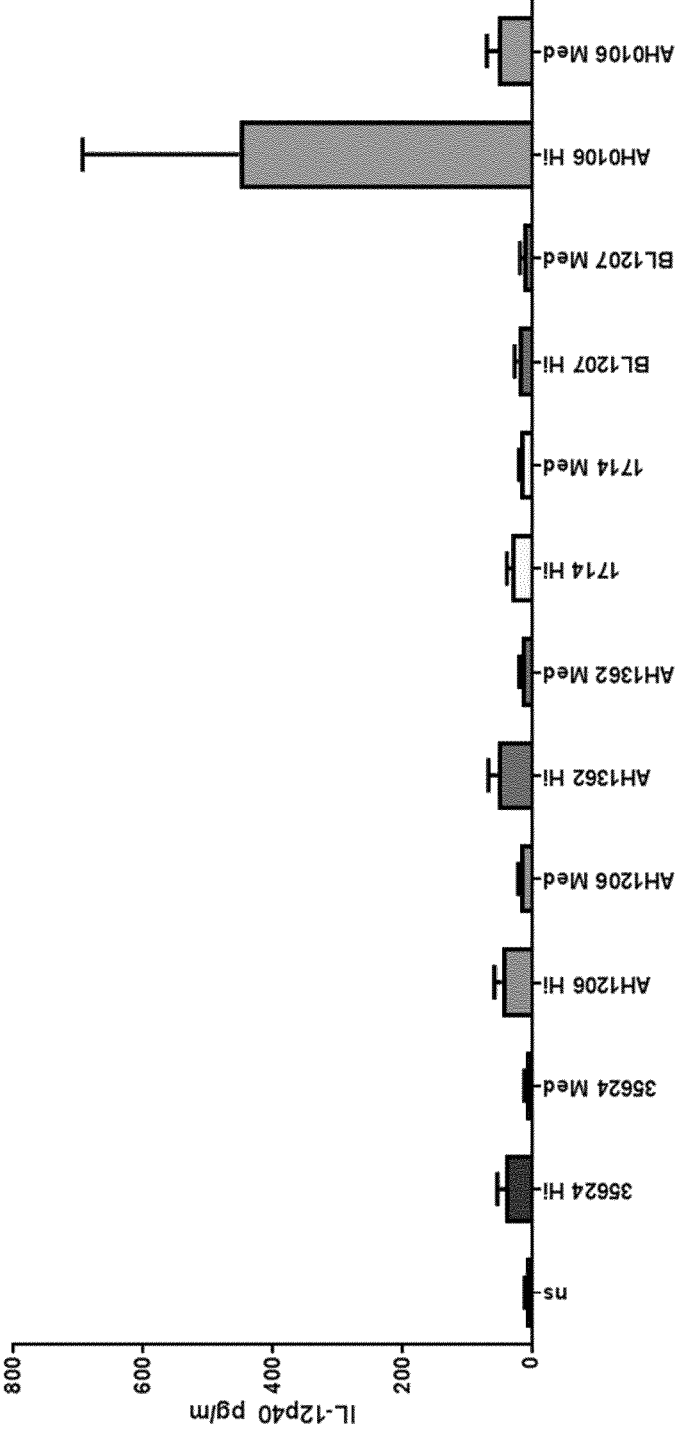
Figure 22:
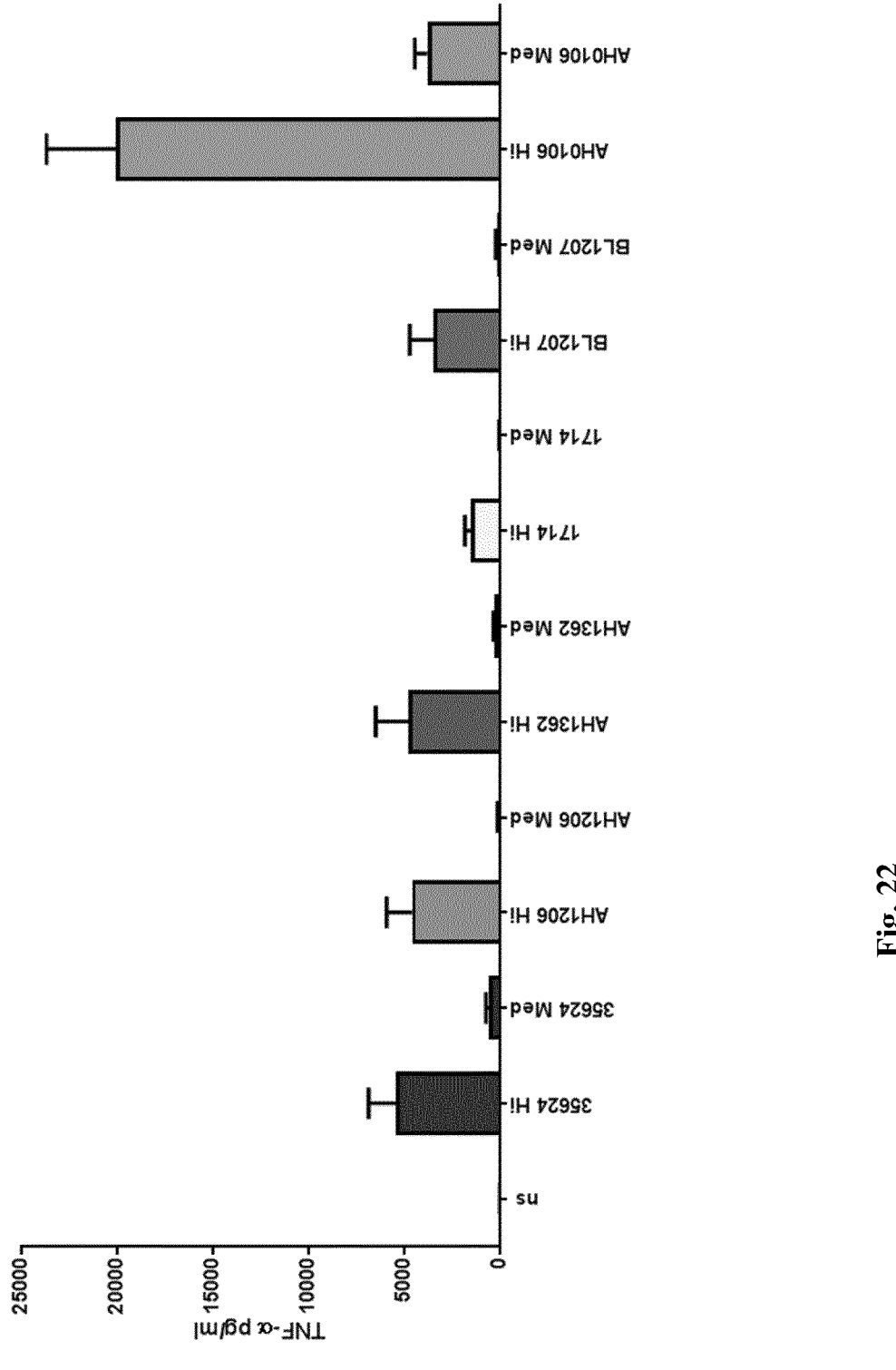
FIG. 22 are bar graphs showing the induction profile of TNF-α in PBMC and in MDDCs after in vitro stimulation with increasing concentrations (medium and high) of *B. longum* strains 35624, AH1206, AH1362, 1714, BL1207 and AH0106.
Figure 22:
Figure 23:
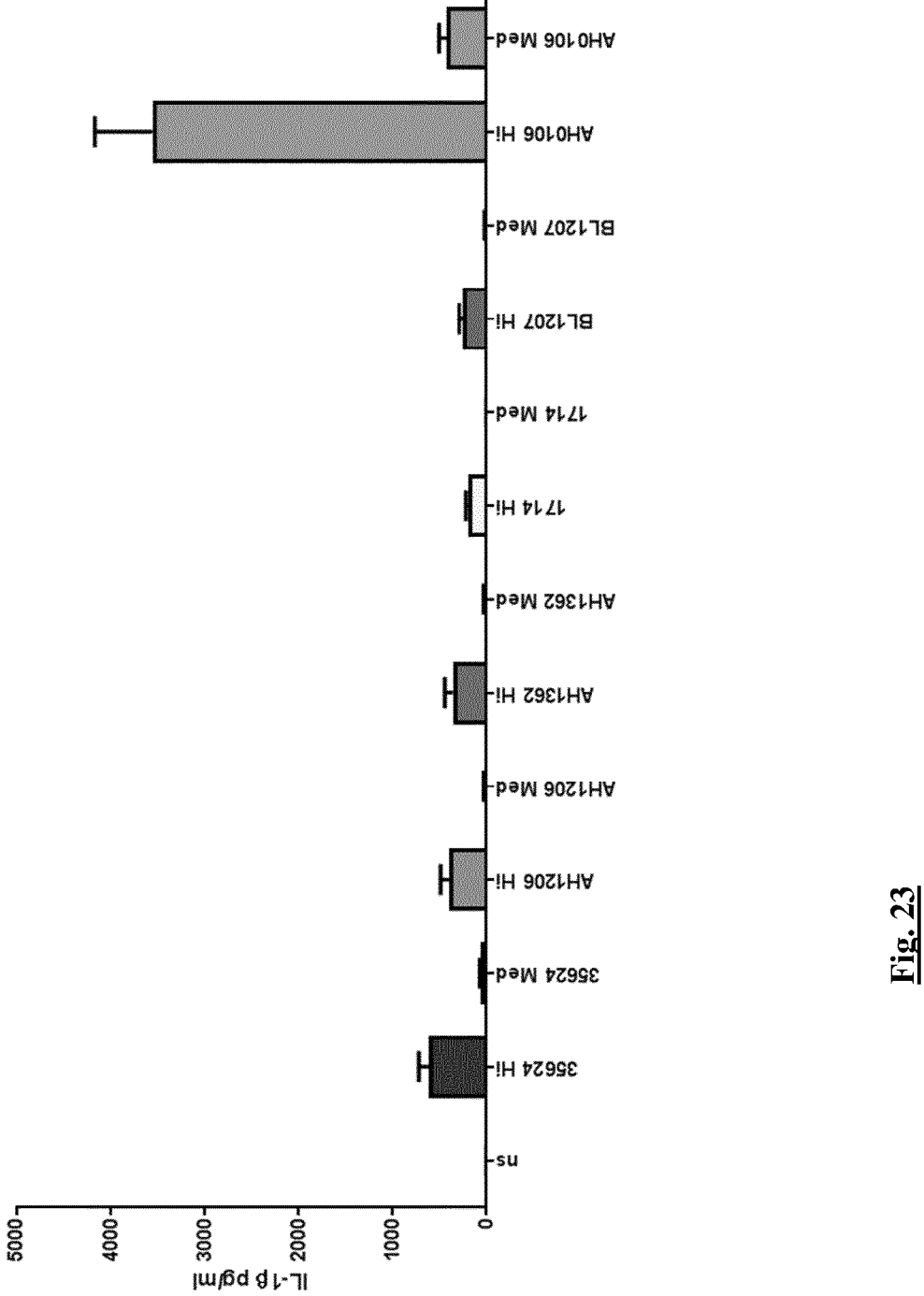
FIG. 23 are bar graphs showing the induction profile of IL-1β in PBMC and in MDDCs after in vitro stimulation with increasing concentrations (medium and high) of *B. longum* strains 35624, AH1206, AH1362, 1714, BL1207 and AH0106.
Figure 23:
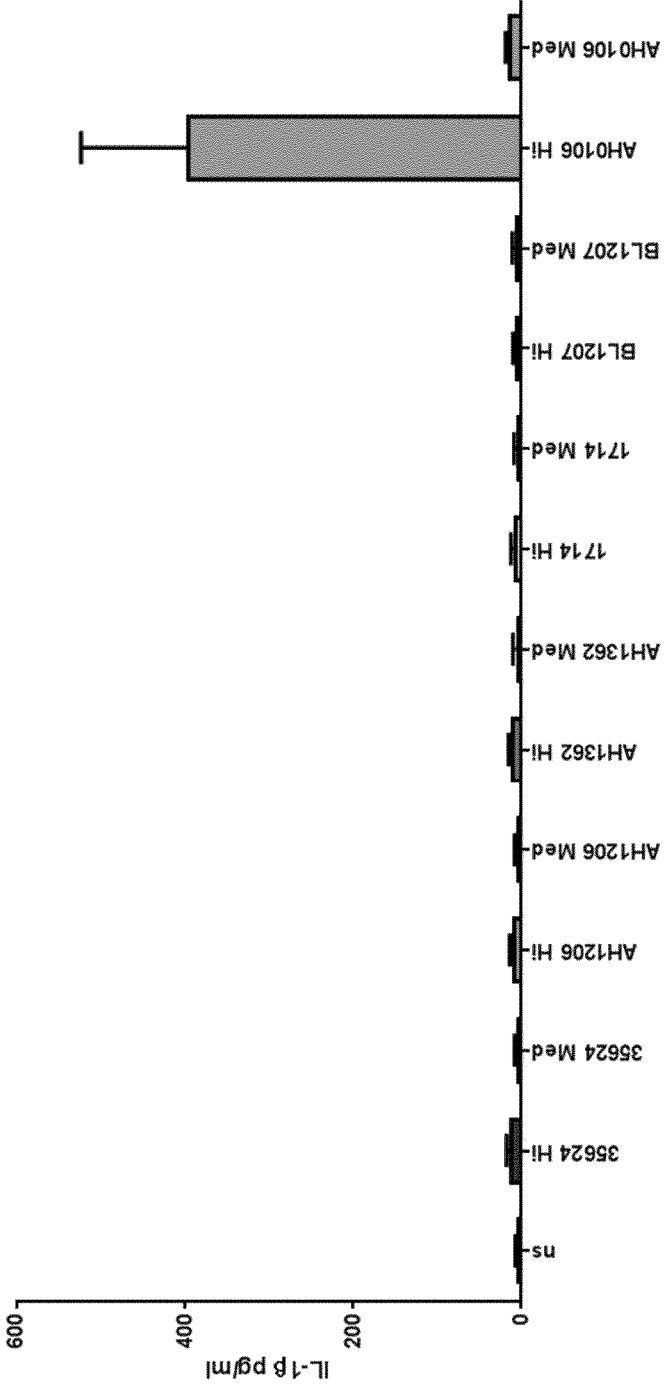

Not every bacterial strain has this effect. Co-incubation with a *Staphylococcus aureus* strain did not reduce DC IP-10 secretion in response to HRV (FIG. 19). Further *B. longums* were investigated to determine to assess the effects of the related *B. longum* strains on mechanisms underlying viral exacerbations in susceptible individuals.

Example 9: Isolation of *Bifidobacterium longum* NCIMB 42020

*Bifidobacterium longum* strain NCIMB 42020 was isolated from faecal samples from healthy human subjects.

Faecal samples were screened for probiotic bacterial strains. Samples were transferred to a collection tube containing Phosphate Buffered Saline (PBS), supplemented with 0.05% cysteine-HCl). The solutions were then incubated for 10 min. The samples were vortexed and plated on selective agar (De Man, Rogosa and Sharpe (MRS) agar+10% sucrose+Mupirocin and Congo red+cysteine+Mupirocin). A Congo red agar screen was used to phenotypically screen for EPS expressing bacterial strains. Briefly, 10 ml Modified Rogosa broth media (+0.05% cysteine) was inoculated aseptically with a freshly grown colony of the bacterial strain and incubated anaerobically at 37° C. until turbid (about 16 to about 24 hours). The broth cultures were aseptically streaked onto Congo Red Agar plates and incubated anaerobically at 37° C. for 48 hours. It is believed that EPS produced as a by-product of the growth and/or metabolism of certain strains prevents the uptake of the Congo red stain resulting in a cream/white colony morphology. Stains that produce less EPS take up the Congo red stain easily, resulting in a pink/red colony morphology. Strains that do not produce an EPS stain red and look almost transparent in the red agar background.

Isolated colonies were picked from the plates and re-streaked three times to ensure purity. Microscope examination, Gram staining, Catalase testing, Fructose-6-Phosphate Phosphoketolase assessment were used to determine presumptive Bifidobacteria species and isolates were stocked in 40% glycerol and stored at −80° C. 16S intergenic spacer region sequencing (IGS) were used to confirm the identity of the newly isolated strains.

Following isolation of a pure bifidobacteria strain, assigned the designation AH0106, it was subsequently deposited at the NCIMB and given the designation 42020. Microbiological characteristics were assessed and are summarized in Table 1 below. *B. longum* NCIMB 42020 is a gram positive, catalase negative pleomorphic shaped bacterium which is Fructose-6-Phoshate Phosphoketolase positive, confirming its identity as a *bifidobacterium*.

TABLE 1

| Physiochemical characteristics of *B. lonium* NCIMB 42020 | |
| --- | --- |
| Strain Characteristics | *B. longum* NCIMB 42020 |
| Gram Stain | + |
| Catalase | − |
| Motility | − |
| F6PPK* | + |

16s-23s intergenic spacer (IGS) sequencing was performed to identify the species of Bifidobacteria isolated.

NCIMB 42020 has a unique IGS sequence with its closest sequence homology to a *Bifidobacterium* longum.

Example 11: Cytokine Profile of AH106 and Comparison to the Profile of Other Bifidobacteria *Longum* Strains with Potential Health Benefits Peripheral blood mononuclear cells (PBMCs) were isolated from healthy donors using density gradient centrifugation. PBMCs were washed and resuspended in Dulbecco's Modified Eagle Medium-Glutamax (DMEM) TM (Glutamax (Glutamine substitute)+pyruvate+4.5 g/l glucose (Gibco catalog 10569-010) 10% fetal bovine serum (Sigma catalog F4135), and 1% penicillin/streptomycin (Sigma catalog P0781). PBMCs were stimulated with different doses of Bifidobacteria *longum* (Total bacteria:PBMC) high (100:1) and mid (50:1)) for 24 h in supplemented DMEM at 37° C., 5% $CO_2$.

For monocyte-derived dendritic cells generation: Peripheral blood mononuclear cells (PBMCs) were isolated from healthy donors using density gradient centrifugation. Human peripheral blood monocytes were isolated using CD14 positive isolation with the MACS system (Miltenyi Biotec, 130-050-201). Cells were cultured in cRPMI media (Life Technologies, 21875-091) with interleukin 4 1000 U/ml (Novartis) and granulocyte macrophage colony stimulating factor (PeproTebh, 300-03) 1000 U/ml for 6 days in order to differentiate them into monocyte-derived dendritic cells (MDDCs). MDDCs were stimulated with different doses of *B. longum* ((Total bacteria:MDDC) high (100:1) and mid (50:1)) for 24 h in cRPMI at 37° C., 5% $CO_2$. Cytokine secretion, was measured using a commercial cytokine kits (MesoScale Discovery) platform following the manufacturers' instructions.

AH0106 induced more IL-10, IL-12p40, TNF-α, IL-1β in both PBMCs and MDDCs than all of the other bacterial strains (35624, AH1206, AH1362, 1714, BL1207) which gave similar profiles to each other (FIGS. 20 to 23). AH106 is a much more potent stimulator of cytokines than the other *B. longum* especially known anti-inflammatory strains such as 35624 and 1714 and demonstrates that AH0106 engages with the human immune system in a different way to the other *B. longum* strains in a manner which is more immunostimulatory.

Example 12: AH0106 Strain (Beneficially Blocks Type 1 Interferons and Resultant IP-10 Induction (a Pro-Inflammatory Chemokine) and Increase Type 3 Interferon IFN-λ in Monocyte Derived Dendritic Cells)

Figure 24:
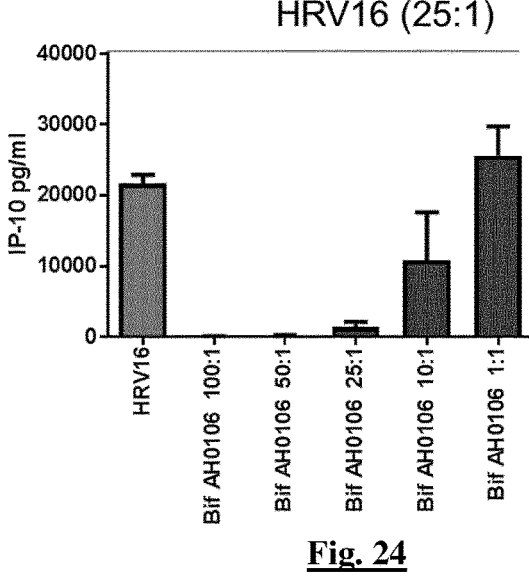
FIG. 24 is a bar chart of the IP-10 response to human rhinovirus in the presence of *B. longum* AH0106.
Figure 25A:
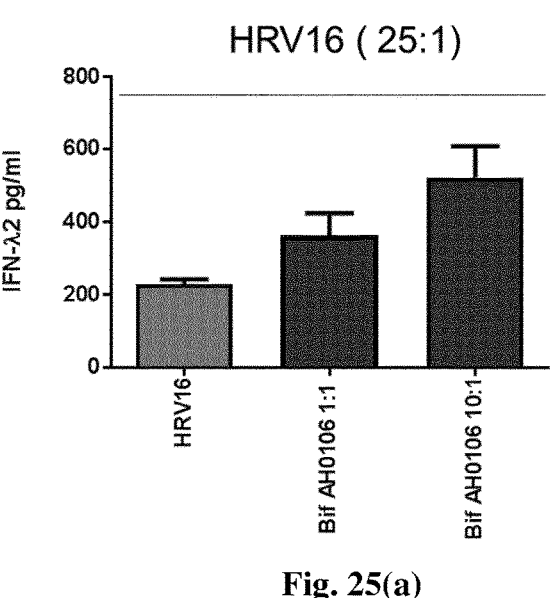
FIGS. 25(*a*) to 25(*c*) are a series of bar charts of interferon lambda (type III interferon), interferon alpha and interferon beta (type 1 interferon) responses to human rhinovirus in the presence of *B. longum* AH0106.
Figure 25B:
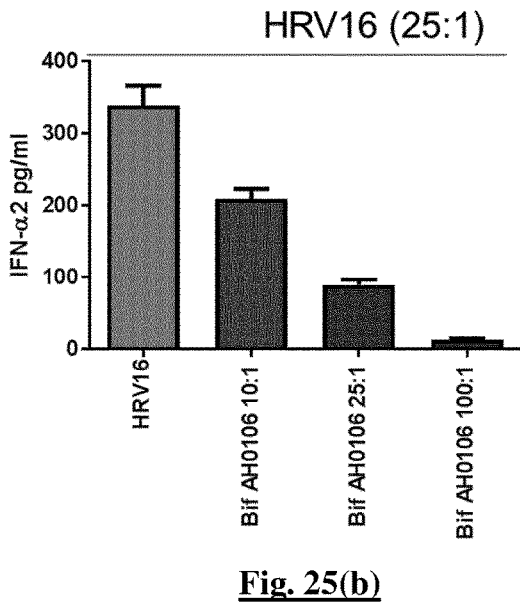
Figure 25C:
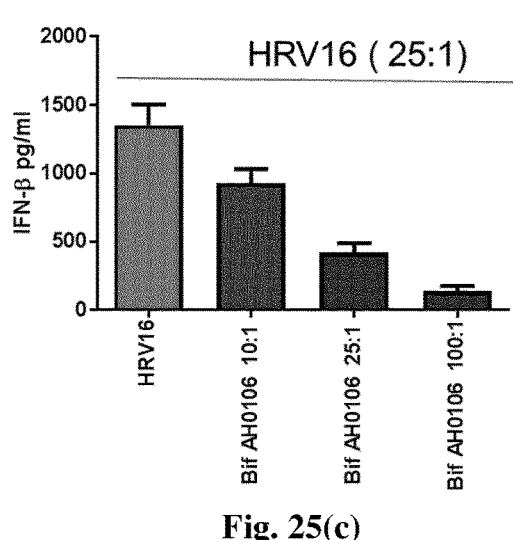

The excessive immune response by dendritic cells to viral infection causes pro-inflammatory responses in the lung. Type 1 IFNs can stimulate the production of IP-10 a chemokine which binds is a chemoattractant for Th1 cells. To determine if a *B. longum* AH0106 might have a beneficial anti-viral effect, on human monocyte-derived dendritic cells, MDDCs were stimulated with *B. longum* AH0106 before being exposed to Human rhinovirus 16 (HRV16) and the interferons and IP-10 response to HRV16 was monitored. MDDCs were stimulated with HRV16 (MOI) 25:1) for 24 h in cRPMI at 37° C., 5% $CO_2$ following pre-treatment (1 h) with multiple doses of *B. longum* AH0106 (100:1, 50:1, 25:1, 10:1, 1:1) or just HRV16 alone. Cytokine secretion was examined by Bio-Plex multiplex suspension array (Bio-Rad Laboratories) measuring IFN-α, IFN-0, IFN-λ and IP-10. Surprisingly, the IP-10 response to RV was attenuated by *B. longum* AH0106 strain in a dose-dependent manner (FIG. 24). Equally surprising, was that co-incubation with *B. longum* AH0106 strain, at lower doses, resulted in the enhancement of type III interferon responses (Interferon lambda) while Interferon alpha and beta responses were suppressed at higher doses, similar to the IP-10 response (FIG. 25). The data shows that *B. longum* AH0106 alters the immune response to RV in supporting a protective immune response while dampening the damaging responses.

Example 13: Not all Gram Positive Bacterial Strains have the Same Effect

Figure 26:
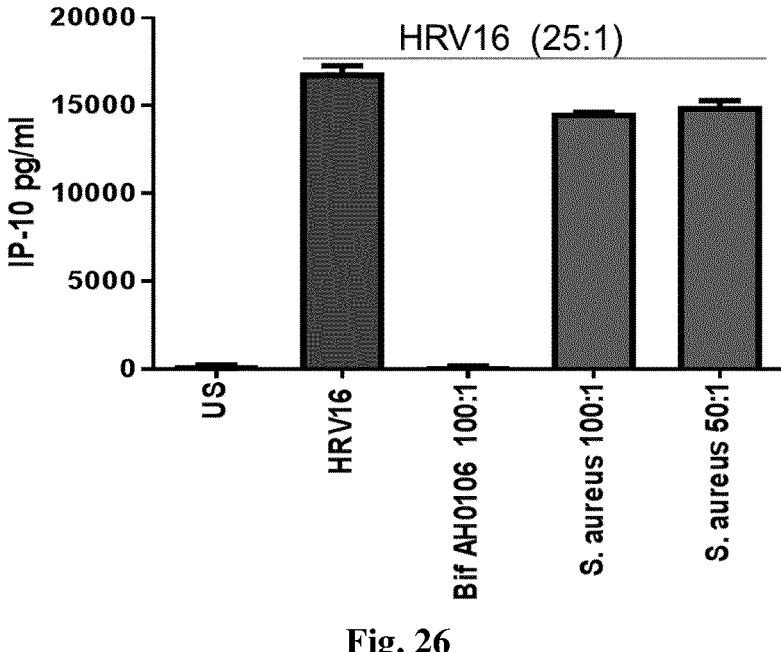
FIG. 26 is a bar chart comparing the IP-10 response to human rhinovirus in the presence of *B. longum* AH0106 or a *Staphylococcus aureus* strain.

To determine if another gram positive bacterial strain might have a beneficial anti-viral effect, on human monocyte-derived dendritic cells, MDDCs stimulated with *Staphylococcus aureus* were exposed to human rhinovirus 16 (HRV16) and the IP-10 response monitored. Briefly, MDDCs were stimulated with HRV16 (MOI) 25:1) for 24 h in cRPMI at 37° C., 5% $CO_2$ following pre-treatment (1 h) with multiple doses of *Staphylococcus aureus* (100:1, 50:1) compared to *B. longum* AH0106 (100:1) or just HRV16 alone. The *Staphylococcus aureus* strain did not reduce DC IP-secretion in response to HRV16 (FIG. 26).

Figure 27:
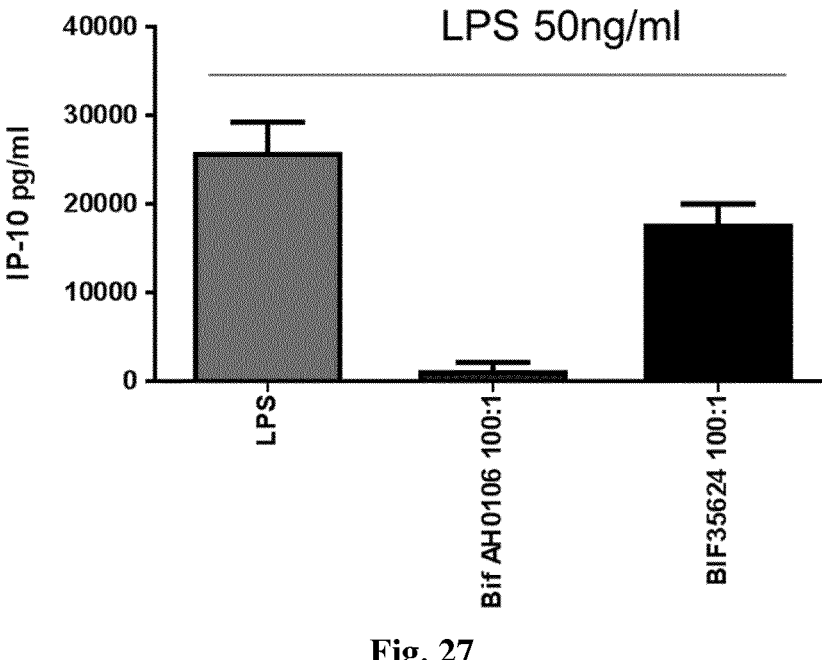
FIG. 27 is a bar chart of the IP-10 response to LPS in the presence of *B. longum* strains AH0106 and 35624.

Example 14: AH0106 Strain Beneficially Blocks TNF-α as Well as IP-10 in Monocyte Derived Dendritic Cells but not all Bifidobacteria *Longum* Strains have the Same Effect Within the inflamed mucosa, it is not just the virus itself that induces IP-10 and TNF-α secretion, but also other (toll like receptor) TLR ligands can induce its production. Therefore, MDDCs were pretreated with *B. longum* AH0106 or *B. longum* 35624 before being exposed to LPS. The IP-10 and TNF-response to LPS a TLR-4 agonist was monitored. Briefly, MDDCs were stimulated with LPS (50 ng/ml) for 24 h in cRPMI at 37° C., 5% $CO_2$ following pre-treatment (1 h) with *B. longum* AH0106 or 35624 at a dose of (100:1) or just LPS alone. Surprisingly, the IP-10 and TNF-α response to LPS was attenuated by *B. longum* AH106 whereas there was only a slight reduction in IP-10 response to LPS after exposure to *B. longum* 35624 (FIG. 27) and *B. longum* 35624 increases TNF-α at the same dose (FIG. 28). This is a very surprising result as *B. longum* 35624 is a well-known anti-inflammatory strain and was the hypothesised top candidate. Some of the cytokine data on *B. longum* AH0106 suggested that it would cause a generalised immune-stimulatory reaction but in practice *B. longum* AH0106 had a superior and specific immune response in this cell system.

Example 15: Comparison of *B. longum* AH106 and *B. longum* 35624 in a Pre-Clinical In Vivo Model of Respiratory Infection We tested the efficacy of *B. longum* AH0106 strain in pre-clinical models designed to show therapeutic benefit. Rhinovirus murine models are not considered to be good surrogates of human infection as mice do not have ICAM, the receptor for major group rhinoviruses to enter the cell.

Therefore, we utilized a lethal influenza model in mice, which is considered a better model (Bartlett et al, 2015). The H1N1 influenza strain A/PR8/34 (100 PFU/50 ul) strain was used to infect mice.

The *B. longum* AH0106 strain, *B. longum* 35624 strain or placebo was administered intranasally at −2 hours, +1 day, and +3 days following viral infection. These strains were administered at a dose of $1 \times 10^9$ total cells.

Figure 46:
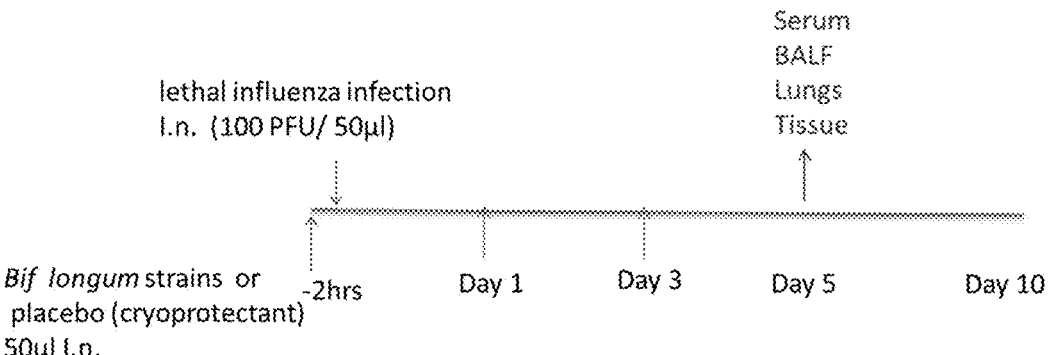
FIG. 46 is a graph showing a comparison of *B. longum* AH106 and *B. longum* 35624 in a pre-clinical in vivo model of respiratory infection.

FIG. 46 shows results for 2 h, day 1, and 3 administration of vehicle control (Group 1), *B. longum* AH0106 (Group 2 and *B. longum* 35624 cell wall fraction (Group 3) per nasal (in 50 μl volume).

Day 0 Administration of a dose of lethal influenza (PR8) per nasal (Group 1-3).

Day 0-10 Monitoring of animals for morbidity (weight, temperature and clinical score, Group 1-3).

Day 5: 5 animals per group are sacrificed for terminal bleed, organ removal and analysis on each day. Day 5 (Group 1-3).

Day 5: Isolation of BAL fluid for the measurement of cytokines and cell infiltrates. Collection of the lung tissue for the quantification of viral titre in the lung by quantitative PCR (half of all lung lobes).

Measurement of Viral Titre in Lung Tissue.

Lung lobes isolated were prepared for the quantification of viral load in lung tissue by quantitative PCR. RNA was prepared with TRI Reagent (Molecular Research Center) and then treated with DNase (Invitrogen) to avoid genomic DNA contamination before RNA was converted to cDNA by reverse transcription using SuperScript III (Invitrogen). cDNA was quantified by real-time PCR (iCycler; Bio-Rad) using SYBR Green (Stratagene) and samples were normalized with GAPDH expression levels. Primers sequences (forward and reverse, respectively) used were influenza PR8 M protein, 5'-GGACTGCAGCGTAGACGCTT-3' (SEQ ID No. 1) and 5'CATCCTGTATATGAGGCCCAT-3' (SEQ ID No. 2).

Groups (1-3):

1. Treatment with Placebo—cryoprotectant resuspended in PBS.
2. Treatment with *B. longum* AH0106 10^9 total cells.
3. Treatment with *B. longum* 35624 10^9 total cells Number of mice per group (Group 1-3)=5

Measurements of Cytokines and Chemokine.

The concentrations of mouse IL-10, IL-2, IL-4, IL-5, IL-6, IL-9, IL-10, IL-12p70, IL-12/IL-23p40, IL-13, IL-15, IL-16, IL-17A, IL-17A/F, IL-17C, IL-17E, IL-17F, IL-21, IL-22, IL-23, IL-30, IL-31, IL-33, IP-10, MIP3α, MIP-2, MIP-1β, MIP-1α, MCP-1, KC/GRO, TNF-α, VEGF, EPO, GM-CSF, IFN-γ in both serum and BAL fluid were measured using a commercial U-PLEX Biomarker Group 1 Mouse 35-Plex (MesoScale Discovery) platform following the manufacturers' instructions; mouse IL-28 (IFN-λ 2/3), mouse G-CSF, mouse TRAIL, mouse AREG were detected using ELISA kits (RayBiotech, Inc.); Oncostatin M and mouse surfactant protein D (SPD) were measured using Quantikine kits from R&D Systems following the manufacturer's instructions. Mouse IFN-α was measured in serum and BAL fluid by mouse IFN alpha platinum ELISA (ThermoFisher scientific) Serum and BAL fluid levels of mouse interferon-β (IFN-β) were measured using VeriKine Mouse Interferon Beta HS ELISA Kits (PBL Assay Science).

Measurement of Cellular Infiltrates into BAL.

Cells were isolated from the BAL fluid and total cell numbers in the bronchoalveolar lavage (BAL) fluid was determined using a Coulter Counter (IG Instrumenten-Gesellschaft AG, Basel, Switzerland). Differential cell counts were performed (200 cell counts/samples) based upon standard morphological and cytochemical criteria on cytospins stained with Diff-Quik solution (Dade Behring, Siemens Healthcare Diagnostics, Deerfield, IL).

Surprisingly, administration of the *B. longum* AH0106 protected the mice better than the *B. longum* 35624 strain.

Figure 31:
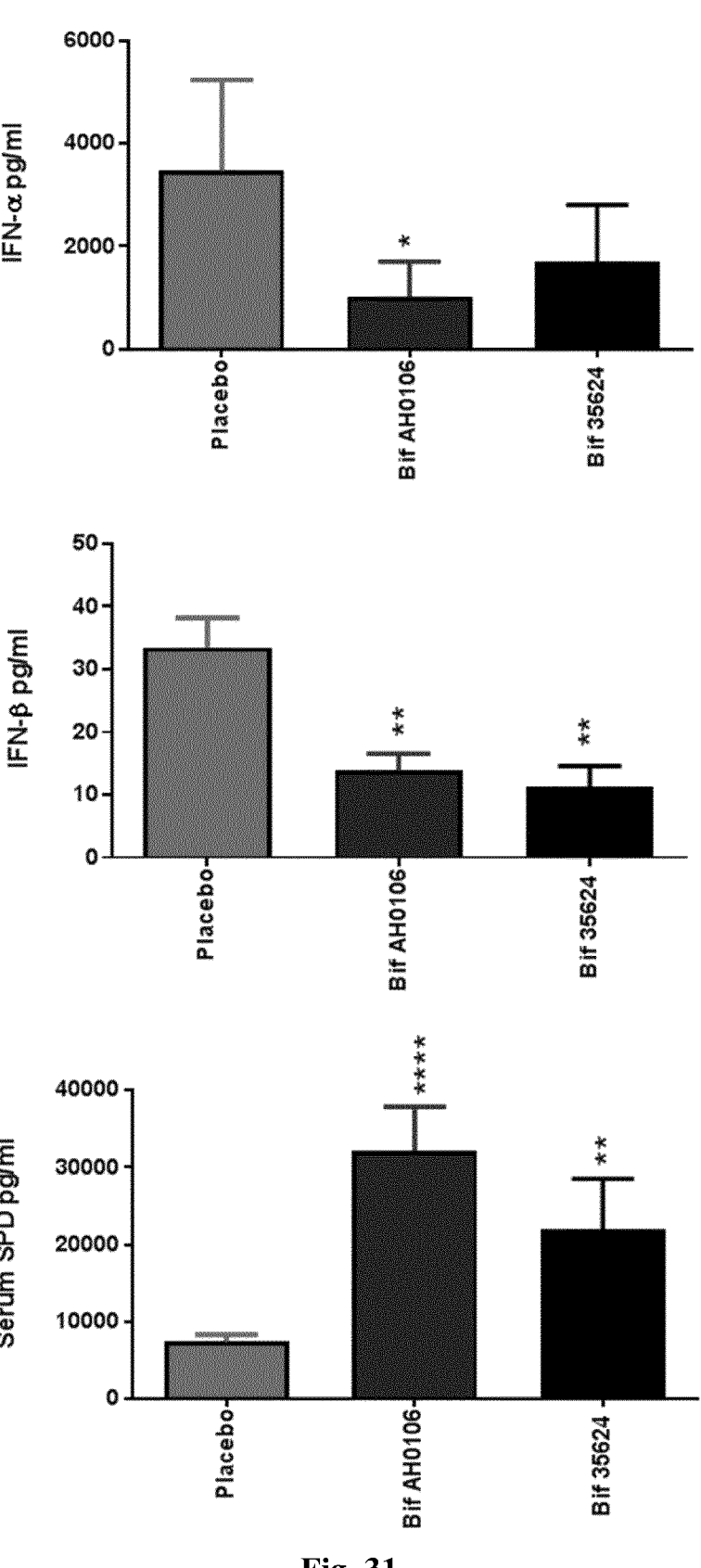
FIG. 31 is a series of graphs of cytokine responses in the Bronchoalveolar lavage (BAL) fluid and surfactant protein D responses in the serum to strains *B. longum* strains AH0106, 35624, and placebo following viral infection.
Figure 32:
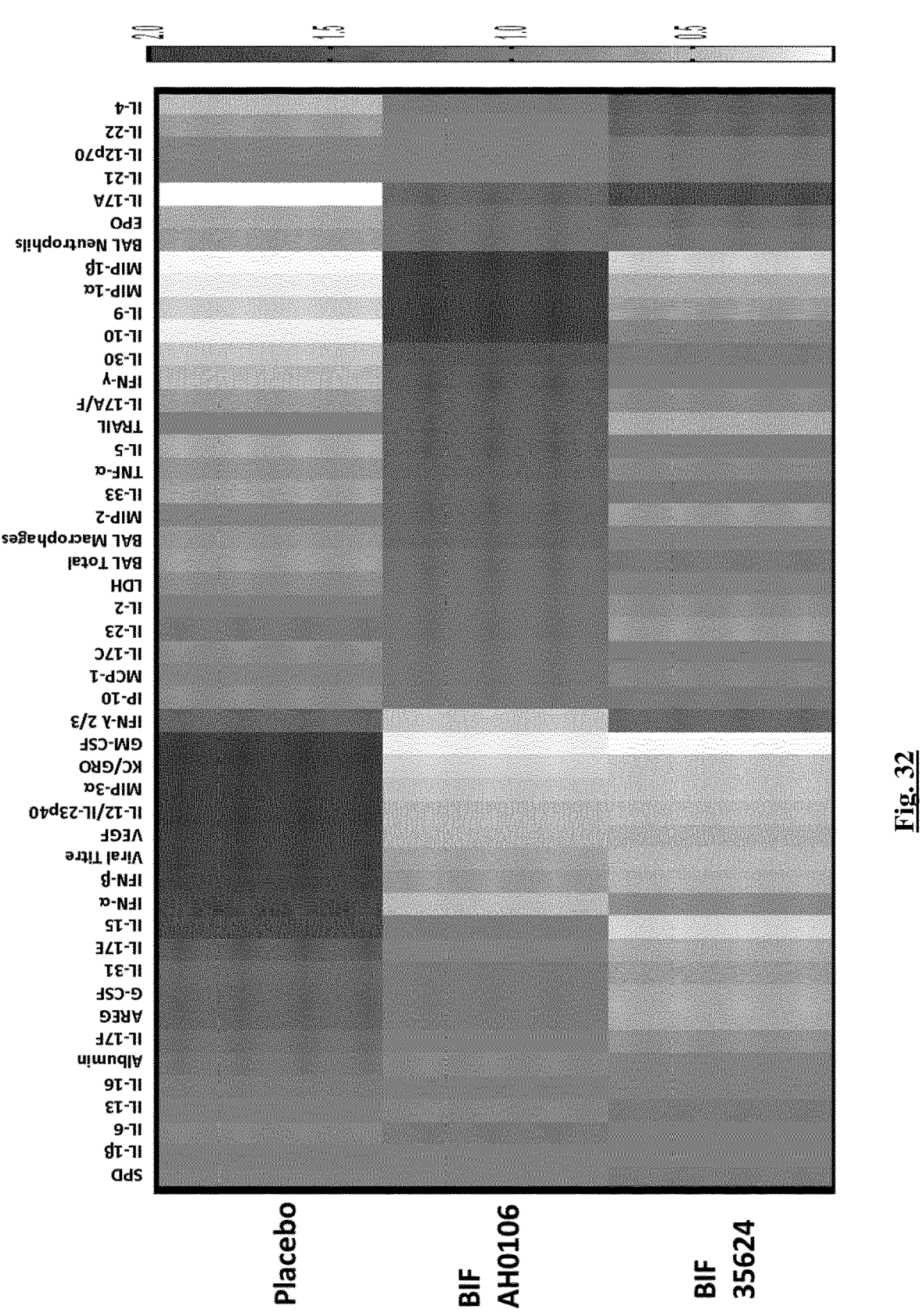
FIG. 32 shows a heat map of different biomarkers measured in the BAL in responses to strains *B. longum* strains AH0106, 35624 and placebo following viral infection; The higher the intensity of band the greater the induction.

Viral titre was reduced by similar levels in both strains (FIG. 29) but mortality was reduced more in the *B. longum* AH0106 treated mice (FIG. 30). This enhanced survival was associated with a reduced interferon-alpha and interferon-beta response and an enhanced surfactant protein D response (FIG. 31). In addition, there was a potent induction of cytokines and chemokines in AH0106 treated animals (FIG. 32) associated with the increase in macrophages in the BAL at day 5 (FIG. 33). This immune response contributed to the enhanced viral clearance seen in the *B. longum* AH0106 treated animals and the start of the healing process brought the influx of macrophages into the lung.

Example 16: Cell Wall Pellet Generation

Following the procedures outlined in Example 1, pellets of cell wall fraction from strain AH0106 was isolated.

The cell wall fraction (<0.45 μm, >100 kDa) was concentrated for in vitro and in vivo tests for more enhanced solubility. To make more concentrated material than 30 mg/ml such as 300 mg/ml (10×) or 150 mg/ml (5×) >100 kDa bacterial Pellet solutions the cell wall fraction is just resuspended in times or 5 times less volume than the starting material.

Example 17: The Cell Wall Fraction from the AH0106 (Beneficially Blocks Type 1 Interferons and Resultant IP-10 Induction (a Pro-Inflammatory Chemokine) in MDDCS To determine if a cell wall fraction from *B. longum* AH0106, as produced in example 16, might have a beneficial anti-viral effect the fraction was incubated on human MDDC's exposed to HRV16 and type 1 interferon and the cell IP-10 response was monitored. For monocyte-derived dendritic cells generation: Peripheral blood mononuclear cells (PBMCs) were isolated from healthy donors using density gradient centrifugation. Human peripheral blood monocytes were isolated using CD14 positive isolation with the MACS system (Miltenyi Biotec, 130-050-201). Cells were cultured in cRPMI media (Life Technologies, 21875-091) with interleukin 4 1000 U/ml (Novartis) and granulocyte macrophage colony stimulating factor (PeproTech, 300-03) 1000 U/ml for 6 days to differentiate them into MDDCs. Cells were cultured in cRPMI media (RPMI (Life Technologies, 21875-091)+10% fetal bovine serum (Sigma catalog F4135) and 1% penicillin/streptomycin (Sigma catalog P0781).

MDDCs were stimulated with HRV16 (MOI) 25:1) for 24 h in cRPMI at 37° C., 5% CO2 following pre-treatment (1 h) with a cell wall fraction from *B. longum* AH0106 (30 mg/ml) or just HRV16 alone. Cytokine secretion was examined by Bio-Plex multiplex suspension array (Bio-Rad Laboratories) (IFN-α, IFN-β, IP-10).

Figure 34A:
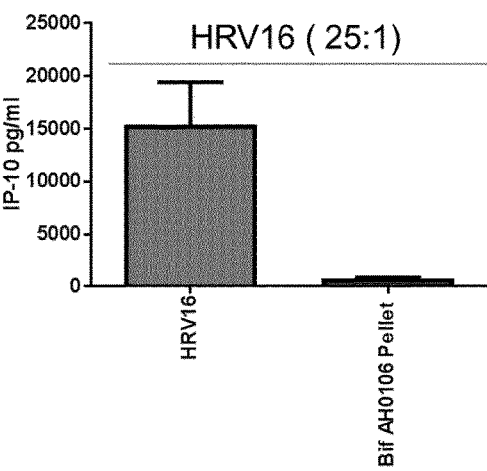
FIG. 34(*a*) is a graph of the IP-10 response to human rhinovirus (HRV16) in the presence of a cell wall fraction (Bif AH0106 pellet) from strain AH0106 in Monocyte Derived Dendritic cells.
Figure 34B:
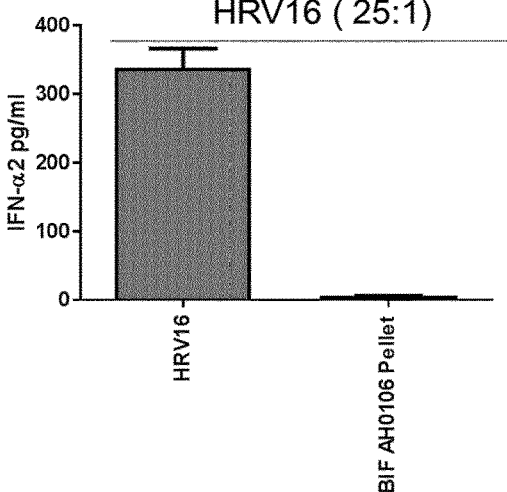
Figure 34C:
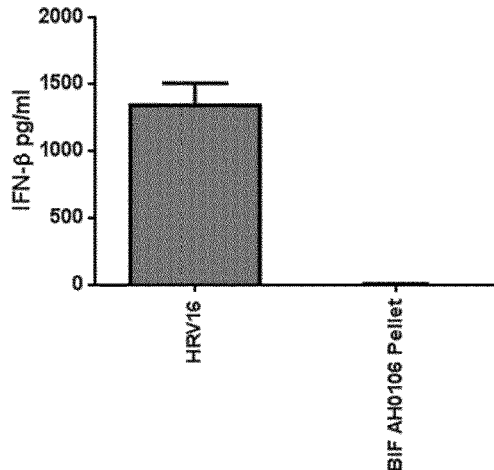

In agreement with the HRV16 stimulated MDDC pretreated with the *B. longum* AH0106 strain results above, the IP-10 (FIG. 34(*a*)), IFN-α (FIG. 34(*b*)), and IFN-β (FIG. 34(*c*)) response to HRV16 was attenuated by a cell wall fraction from the *B. longum* AH0106 strain.

Figure 35A:
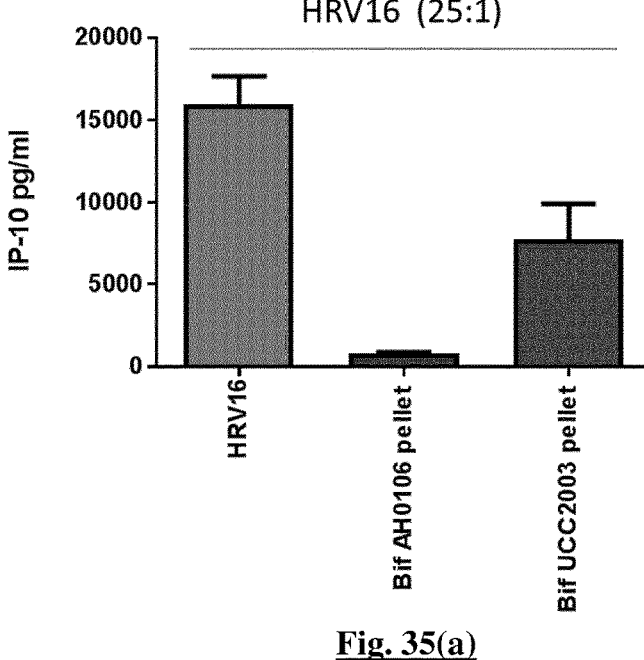
FIG. 35(*a*) is a bar chart of the IP-10 response to human rhinovirus (HRV16) in the presence of a cell wall fraction from strain UCC2003 compared to a cell wall fraction from strain AH0106 in Monocyte Derived Dendritic cells.
Figure 35B:
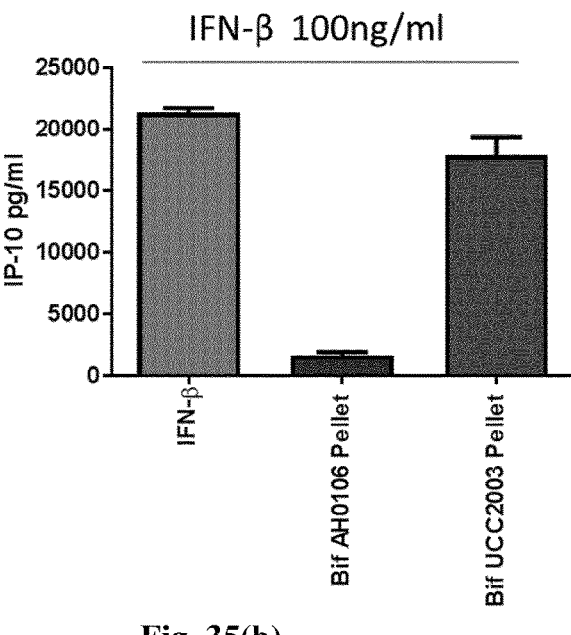

Example 18: Not all Cell Wall Fractions from Bifidobacteria Species have the Same Effect Cell wall fraction from another Bifidobacteria, Bifidobacteria *breve* (Bif UCC2003) was also tested using the methodology described in example 4 and did not show similar significant effects. The Bif UCC2003 fraction reduced IP-10 production following viral stimulation but not to the same extent as the *B. longum* AH0106 cell wall fraction during a 24 hours assay (FIG. 35(*a*)).

Additionally, within the inflamed mucosa, it is not just the virus itself that induces IP-10 secretion; other cytokines can also induce IP-10 production. Cytokines such as IFN-β are produced as part of the primary anti-viral host response. IFN-β in particular is a potent inducer of IP-10. Therefore, we examined the effect of the cell wall fraction on secretion of IP-10 in response to IFN-β (FIG. 35(*b*)). MDDCs were stimulated with IFN-β (200 ng/ml) for 24 h in cRPMI at 37° C., 5% CO2 following pre-treatment (1 h) with cell wall fractions (30 mg/ml) or IFN-β alone. The *B. longum* AH0106 cell wall pellet fraction suppressed IP-10 secretion to these stimuli, while the Bif UCC2003 cell wall pellet fraction did not reduce IP-10 secretion at all.

Figure 36A:
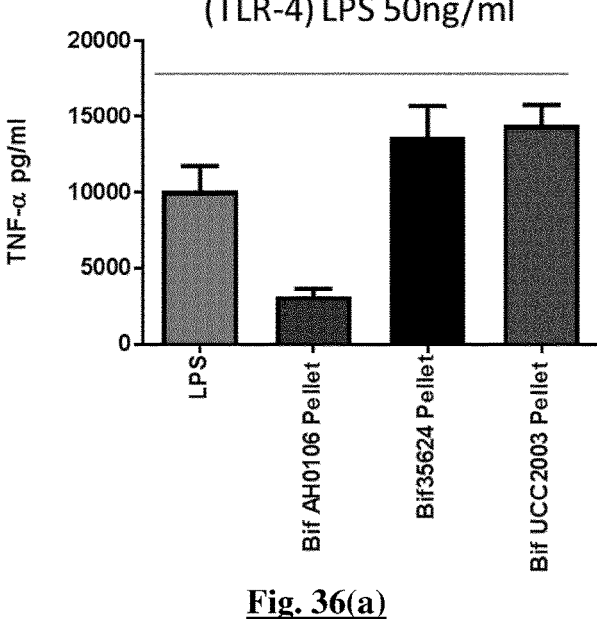
FIG. 36(*a*) is a bar chart of the TNF-α response to LPS in the presence of a cell wall fraction from strain UCC2003 compared to a cell wall fraction from *B. longum* strains AH0106 and 35624 in Monocyte Derived Dendritic cells.
Figure 36B:
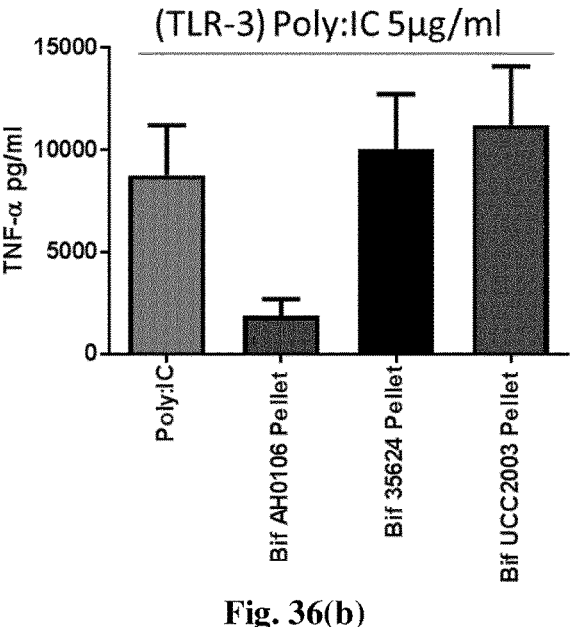

Example 19: The Cell Wall Fraction from *B. longum* AH0106 Strain has an Additional Beneficial Effect (Blocks TNF-α) in Monocyte Derived Dendritic Cells which Contribute to the Reduction of Inflammation and not all Bifidobacteria Strains have the Same Effect Within the inflamed mucosa, it is not just the virus itself that induces pro-inflammatory TNF-α secretion, but also other (toll like receptor) TLR ligands can induce its production. Therefore we examined the secretion of TNF-α in response to the TLR ligands Poly:IC (TLR-3) and LPS (TLR-4). MDDCs were pretreated with cells wall *B. longum* AH0106, *B. longum* 35624 and Bif UCC2003 before being exposed to LPS, a TLR-4 agonist, and the IP-10 and TNF-response to was monitored. MDDCs were stimulated with either the TLR-4 agonist LPS (50 ng/ml) or the TLR-3 agonist Poly:IC (5 μg/ml) for 24 h in cRPMI at 37° C., 5% CO2 following pre-treatment (1 h) with cell wall fractions from Bifidobacteria at a dose of (30 mg/ml) or just the TLR agonist alone. TNF-α secretion was examined by Quantikine ELISA (R &D systems). In agreement with the results from the whole *B. longum* AH0106 strain the TNF-α response to LPS and Poly:IC was attenuated by the cell wall fraction from *B. longum* AH106 whereas both the cell wall fractions from *B. longum* 35624 and Bif UCC2003 increases TNF-α at the same dose (FIGS. 36(*a*) and 36(*b*)). This is a very surprising result as *B. longum* 35624 is a well-known anti-inflammatory strain and *B. longum* AH0106 had a superior response in this system.

In summary, as illustrated in examples 9 to 19, we have shown there is an enhanced Type III interferon response which beneficial, and addition of the cell wall fraction from AH0106 causes this desired response. In cells that are part of the later host immune system response (DC's) the cell wall fraction blocks the excessive Type 1 interferon response that can lead to cell damage and secondary infection. This targeted effect has benefit in infections caused by influenza, the common cold (rhino virus) and RSV, viral exacerbation of chronic respiratory diseases such as asthma, COPD and ARDs in both children and adults and in obese individuals.

Example 20: Isolation and Characterisation of Bacteria Isolated from Adult Faeces Isolation of Probiotic Bacteria Fresh faeces was obtained from healthy adults and serial dilutions were plated on TPY (trypticase, peptone and yeast extract) and MRS (deMann, Rogosa and Sharpe) media supplemented with 0.05% cysteine and mupirocin. Plates were incubated in anaerobic jars (BBL, Oxoid) using CO2 generating kits (Anaerocult A, Merck) for 2-5 days at 37° C. Gram positive, catalase negative rod-shaped or bifurcated/pleomorphic bacteria isolates were streaked for purity on to complex non-selective media (MRS and TPY). Isolates were routinely cultivated in MRS or TPY medium unless otherwise stated at 37° C. under anaerobic conditions. Presumptive *Bifidobacterium* were stocked in 40% glycerol and stored at –20° C. and –80° C.

Following isolation of the pure bifidobacteria strain, assigned the designation AH0103, it was subsequently deposited at the NCIMB and given the designation 41713. Microbiological characteristics were assessed and are summarized in Table 1 below. *B. longum* NCIMB 41713 is a gram positive, catalase negative pleomorphic shaped bacterium which is Fructose-6-Phoshate Phosphoketolase positive confirming its identity as a *bifidobacterium*.

TABLE 1

| Physiochemical characteristics of *B. longum* NCIMB 41713 | |
| --- | --- |
| Strain Characteristics | *B. longum* NCIMB 41713 |
| Gram Stain | + |
| Catalase | – |
| Motility | – |
| F6PPK* | + |
| Milk coagulation | + |
| 45° C. anaerobic culture | – |
| 45° C. aerobic culture | – |

*signifies Fructose-6-Phoshate Phosphoketolase Assay

Species Identification 16s intergenic spacer (IGS) sequencing was performed to identify the species of bifidobacteria isolated. NCIMB 41713 has a unique IGS (SEQ ID No. 6) with its closest sequence homology to a *Bifidobacterium* longum.

Example 21: Cell Wall Pellet Generation

The cell wall fraction (<0.45 μm, >100 kDa) was concentrated for in vitro and in vivo tests for more enhanced solubility. To make more concentrated material than 30 mg/ml such as 300 mg/ml (10×) or 150 mg/ml (5×) >100 kDa bacterial Pellet solutions the cell wall fraction is just resuspended in times or 5 times less volume than the starting material.

Example 22 the Cell Wall Fraction from the NCIMB Strain 41713 (AH0103) (Beneficially Blocks Type 1 Interferons and Resultant IP-10 Induction (a Pro-Inflammatory Chemokine) in Dendritic Cells To determine if a cell wall fraction from *B. longum* AH0103, as produced in example 20, might have a beneficial anti-viral effect the fraction was incubated on human DC's exposed to HRV16 Cytokine secretion was examined by Bio-Plex multiplex suspension array (Bio-Rad Laboratories). First IP-10 was assessed and then subsequently a range of cytokines were assessed (IFN-α, IFN-β, IP-10).

Figure 37:
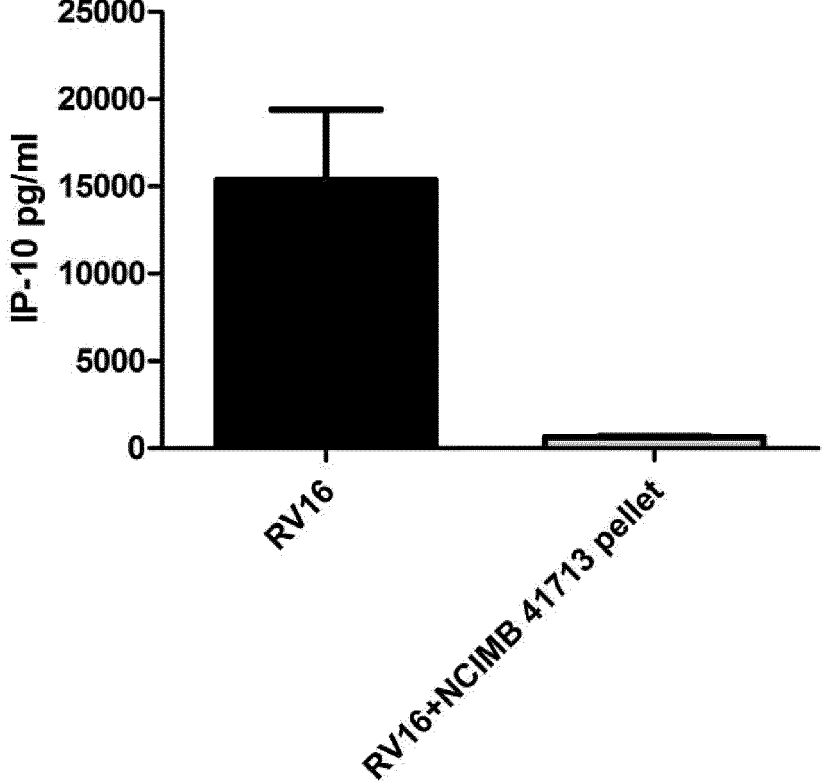
FIG. 37 is a graph of the IP-10 response to rhinovirus (RV16) in the presence of a cell wall fraction (Bif AH0103 pellet) from strain AH0103 in Monocyte Derived Dendritic cells.

In agreement with the HRV16 stimulated MDDC pre-treated with the *B. longum* AH0106 strain results above, the IP-10 response to HRV16 was attenuated by a cell wall fraction from the *B. longum* AH0103 strain (FIG. 37).

Figure 38A:
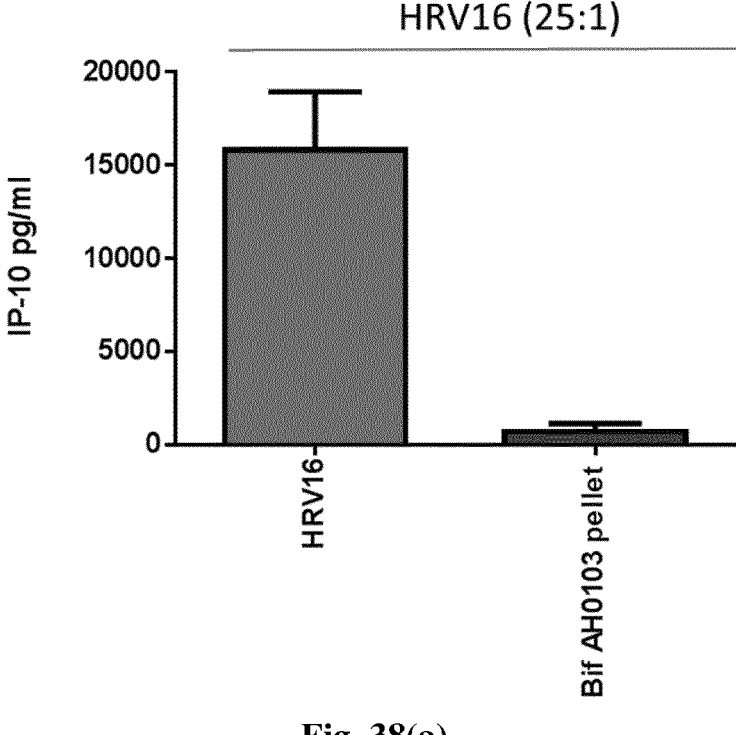
FIG. 38(*a*) is a graph of the IP-10 response to rhinovirus (RV16) in the presence of a cell wall fraction (Bif AH0103 pellet) from strain AH0103 in Monocyte Derived Dendritic cells.
Figure 38B:
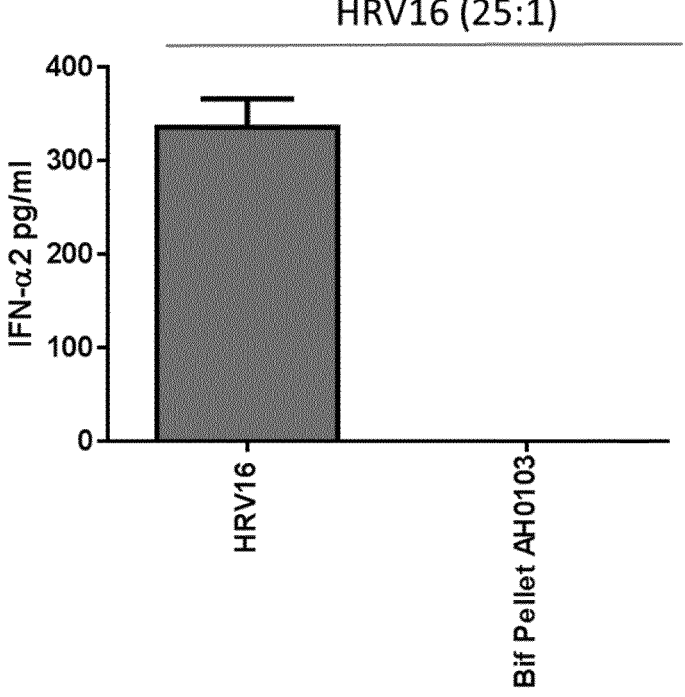
Figure 38C:
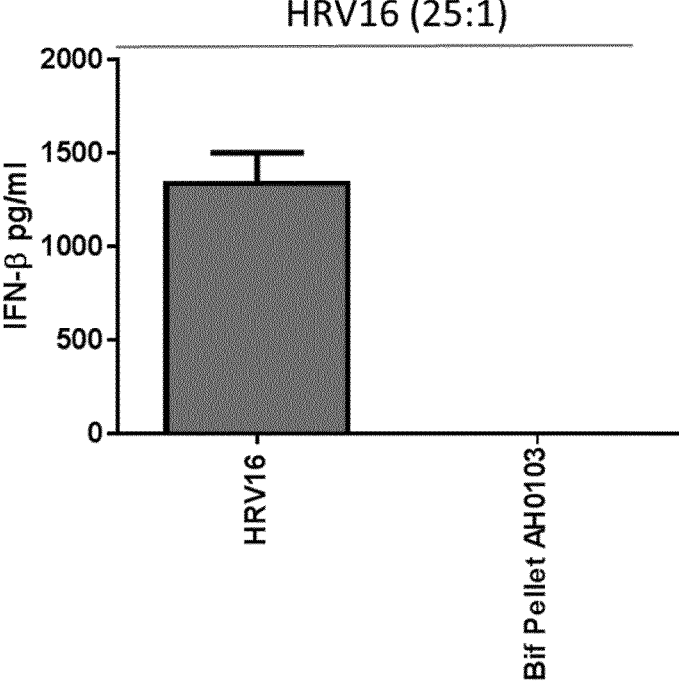

In agreement with the HRV16 stimulated MDDC pre-treated with the *B. longum* AH0106 strain results above, the IFN-α, IFN-β, and IP-10 response to HRV16 was attenuated by a cell wall fraction from the *B. longum* AH0103 strain. (FIGS. 38 (*a*)(*b*)(*c*)).

*B. longum* NCIMB 41713 promotes anti-viral defence and inhibits damaging pro-inflammatory responses and is useful in the prevention and/or treatment of virus induced ARDS, or viral-induced exacerbations in asthma and COPD patients.

Figure 39:
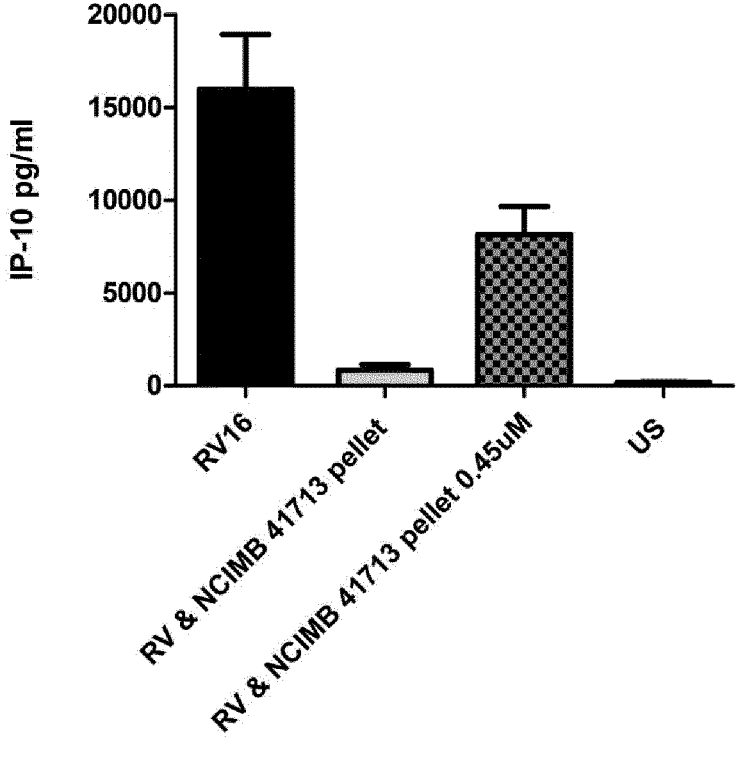
FIG. 39 is a bar chart of the IP-10 response to human rhinovirus (HRV16) in the presence of cell wall fraction with and without 0.45 μM filtration from strain NCIMB 41713 (AH0103)

Dendritic cells (DCs) are generated following isolation of human CD14+ monocytes from peripheral blood and culture in GM-CSF and IL-4 for 6 days. DCs are exposed to rhinovirus (HRV 16) and the IP-10 response to RV is monitored. However, the activity was reduced following filtration at 0.45 μM to remove all intact cells (FIG. 39).

Example 23

Figure 40:
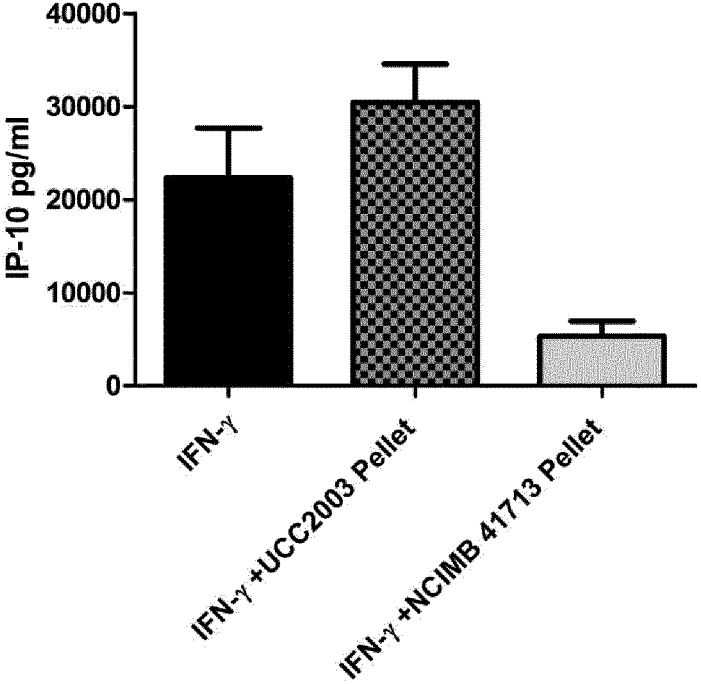
FIG. 40 are bar charts of the secretion of IP-10 in response to interferon beta, interferon gamma and interferon lambda in the presence of a cell wall fraction from strain UCC2003 compared to a cell wall fraction from strain NCIMB 41713 (AH0103)

Within the inflamed mucosa, it is not just the virus itself that induces IP-10 secretion, but also other cytokines can induce its production. Therefore, we examined the secretion of IP-10 in response to interferon-beta, interferon-gamma, and interferon-lambda (FIG. 40). The *B. longum* NCIMB 41713 cell wall pellet fraction suppressed IP-10 secretion to these stimuli while the Bif UCC2003 fraction did not reduce IP-10 secretion.

A final *B. longum* strain NCMIB 41715 (AH1362) was also tested to determine if this type of response was also present

Example 24: Cell Wall Pellet Generation

The cell wall fraction (<0.45 μm, >100 kDa) was concentrated for in vitro and in vivo tests for more enhanced solubility. To make more concentrated material than 30 mg/ml such as 300 mg/ml (10×) or 150 mg/ml (5×) >100 kDa bacterial Pellet solutions the cell wall fraction is just resuspended in times or 5 times less volume than the starting material.

In this case the Bacterial cells were disrupted by pressure of 1500 psi on the high setting (20,000 psi equivalent) using a French press (Thermo Electron Corporation FA-078A). This procedure is repeated three times on ice.

Example 25

*B. longum* NCIMB 41715 promotes anti-viral defence and inhibits damaging pro-inflammatory responses and is useful in the prevention and/or treatment of virus induced ARDS, or viral-induced exacerbations in asthma and COPD patients.

Figure 41:
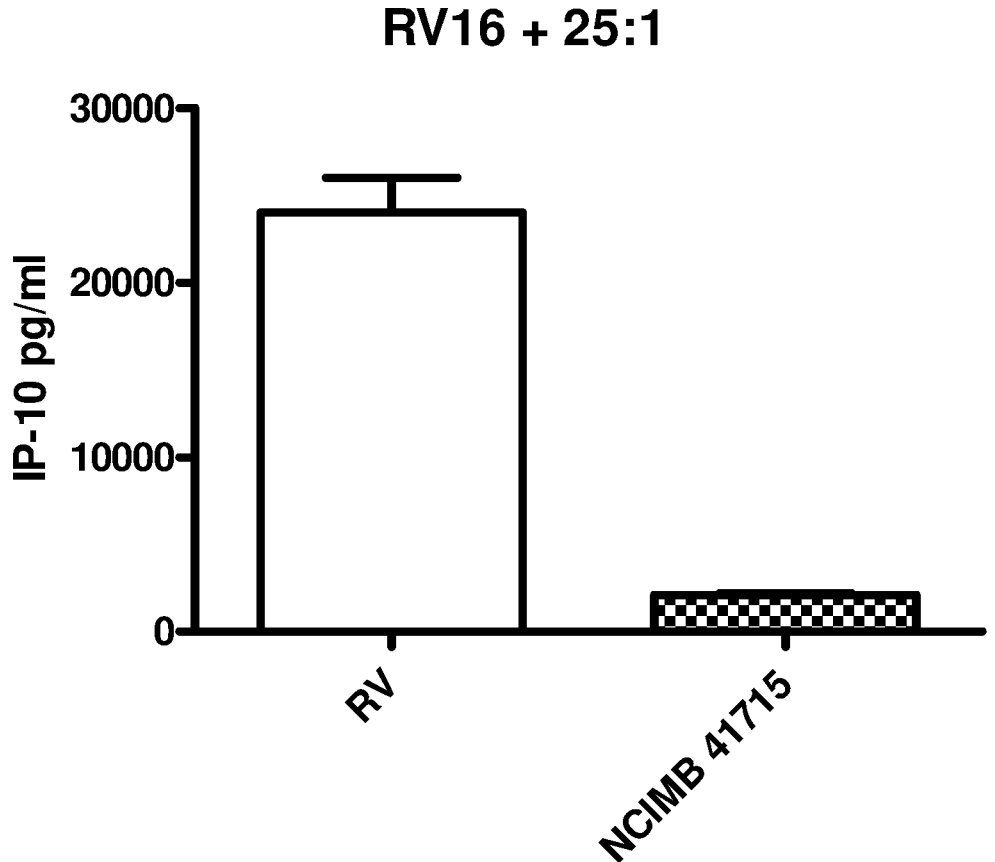
FIG. 41 is a bar chart of the IP-10 response to human rhinovirus (HRV16) in the presence of a *B. longum* strain NCIMB 41715 (AH1362)

Dendritic cells (DCs) are generated following isolation of human CD14+ monocytes from peripheral blood and culture in GM-CSF and IL-4 for 6 days. DCs are exposed to rhinovirus (RV) and the IP-10 response to RV is monitored. The IP-10 response to RV is attenuated by *B. longum* NCIMB 41715 cell wall pellet fraction (FIG. 41).

Example 26: The Cell Wall Fraction from the NCIMB Strain 41715 (AH1362) (Beneficially Blocks Type 1 Interferons and Resultant IP-10 Induction (a Pro-Inflammatory Chemokine) in Dendritic Cells To determine if a cell wall fraction from *B. longum* AH1362, as produced in example 20, might have a beneficial anti-viral effect the fraction was incubated on human DC's exposed to HRV16 Cytokine secretion was examined by Bio-Plex multiplex suspension array (Bio-Rad Laboratories). First IP-10 was assessed and then subsequently a range of cytokines were assessed (IFN-α, IFN-β, IP-10).

Figure 42A:
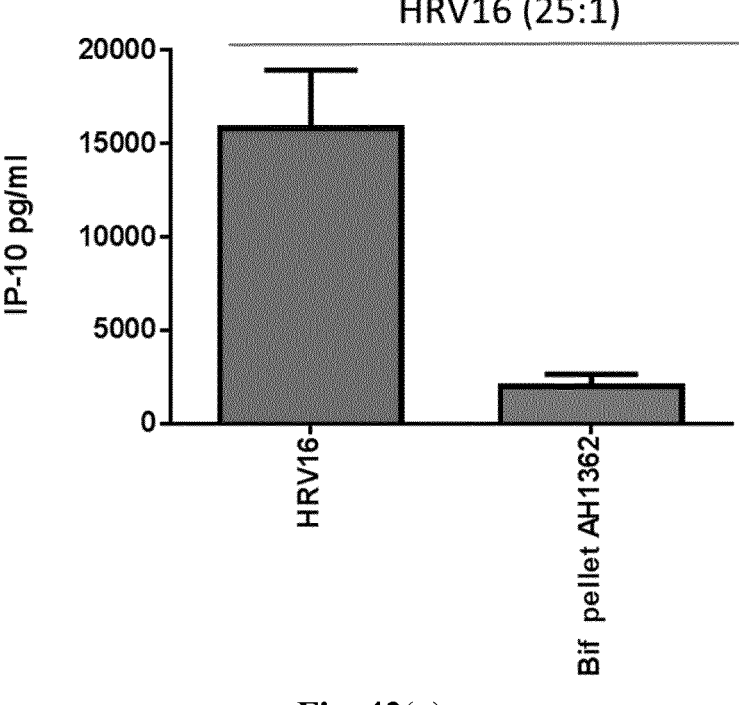
FIG. 42 (*a*) is a graph of the IP-10 response to rhinovirus (RV16) in the presence of a cell wall fraction (Bif AH1362 pellet) from strain AH1362 in Monocyte Derived Dendritic cells.
Figure 42:
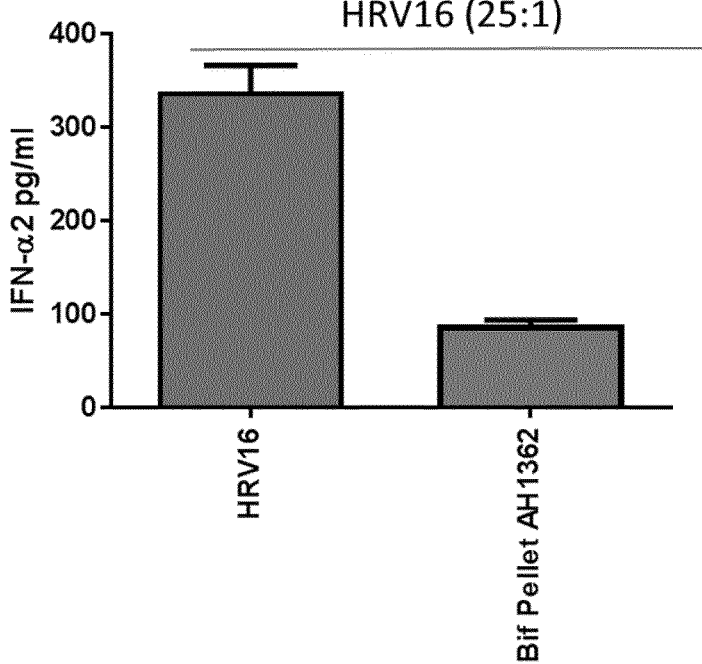
Figure 42C:
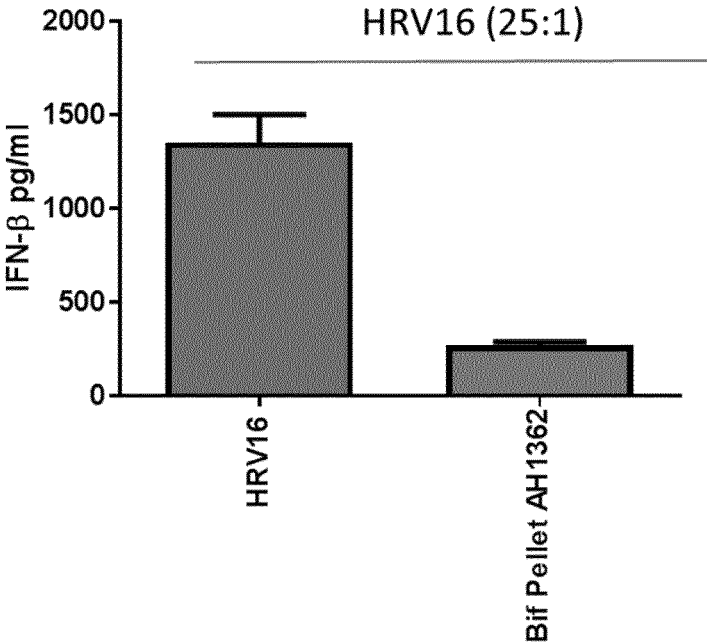

In agreement with the HRV16 stimulated MDDC's pre-treated with the *B. longum* AH0106 or the AH103 strain results above the IFN-α, IFN-β, and IP-10 response to HRV16 was attenuated by a cell wall fraction from the *B. longum* AH1362 strain. (FIG. 42 *a,b,c*).

In agreement with the HRV16 stimulated MDDC pre-treated with the other *B. longum* strain results above, the IFN-α, IFN-β, and IP-10 response to HRV16 was attenuated by a cell wall fraction from the *B. longum* AH1362 strain. (FIGS. 42 (*a*)(*b*)(*c*)).

Example 27: The Hamster model of SARS-COV2

The efficacy of the *Bifidobacterium longum* strains and cell wall fractions are tested in pre-clinical models of SARS-Cov2. Syrian golden hamster model is an important tool for studying transmission, pathogenesis, treatment and vaccination against SARS-CoV-2 virus. (Chan et al 2020). These hamsters are one of the most similar models to humans, making them a useful model for researchers looking into COVID-19 therapies, particularly ones targeting the respiratory tract. The SARS-CoV-2 strain (105 PFU/100 ul) is used to infect the hamsters intranasally under intraperitoneal ketamine (200 mg/kg) and xylazine (10 mg/kg). Chemokine/cytokine profiling is performed on the lung tissues of the virus-challenged and mock-infected animals by qRT-PCR. For example, the *B. longum* 35624 cell wall fraction (150 mg/ml) is administered intranasally at –1 day, +1 day, +3 days and +5 days following viral infection. Both Male and female Syrian hamsters, aged 6-10 weeks old are used. All virus challenge takes place in a Biosafety Level-3 animal facility. –2 h, day 1, 3 and 5 Administration of vehicle control (Group 1) and *B. longum* 35624 cell wall fraction (Group 2) per nasal (in 100 μl volume).

Day 0 Administration of a dose of SARS-CoV-2 virus per nasal (Group 1-2).

Day 0-14 Monitoring of animals for morbidity (weight, temperature and clinical score, Group 1-2).

Day 2, 7 and 14: 5 animals per group are sacrificed for terminal bleed, organ removal and analysis on each day. Day 3 (Group 1 and 2), day 5 (Group 1-3) and day 10 (Group 1 and 2).

Day 2, 7 and 10: Isolation of BAL fluid for the measurement of cytokines and markers of lung damage. Collection of the lung tissue for the quantification of Viral load in the lung by quantitative PCR (half of all lung lobes) and median tissue culture infectious dose (TCID50) assays. Quantitation of live infectious virus by TCID50 assay is performed on the nasal turbinate and lung tissues.

Coronavirus

The normal cold-causing coronaviruses, as well as many other viruses that cause common colds, are typically restricted to the upper respiratory tract, that is, the nose and sinuses. However, both SARS-CoV and SARS-CoV-2 and MERS-CoV are capable of invading deep into the lungs, something that is associated with more severe disease. These SARS-CoV viruses bind to the ACE-2 receptor and MERS-CoV binds to host receptor dipeptidyl peptidase 4 (DPP4) on human cells in order to gain entry. These receptors are present in ciliated epithelial cells in the upper and lower airway, as well as in type II pneumocytes, which reside in the alveoli in the lower airway and produce lung-lubricating proteins which hare very important for lung function (Song et al 2019) In the early stages of infection, replication occurs in lung epithelial or type II pneumocytes cells, leading to activation of viral sensors and the release of antiviral Type I and Type III interferons (IFN's) as well as chemokines and cytokines. These pro-inflammatory mediators help to clear the primary infection but Type I IFN's can also cause subsequent damage (immunopathology) and severe disease when an excessive amount is produced. IFN Type I responses, such as increases in IFN-α and IFN-β molecules, have been shown to directly correlate with increased mor- bidity and mortality in models of SARS-Cov and MERS- Cov (Scheuplein et al 2015, Channappanavar et al, 2016, Channappanavar et al, 2019). In agreement with this the administration of inhaled IFN-α-2b to a 50-year-old male patient who tested positive to SARS-CoV-2 failed to prevent mortality (Xu et al 2020).

More recently, a retrospective study of 446 patients with COVID-19 reported that early use of IFNα decreased mor- tality, whereas late use of IFNα increased mortality and delayed recovery (Wang et al., 2020). There is increasing evidence that patients with severe COVID-19 have a robust type I interferon response, which contrasts with the delayed, possibly suppressed, interferon response seen early in infec- tion. A robust type I interferon response could exacerbate hyperinflammation in the progression to severe COVID-19 through diverse mechanisms. A robust IFN-I response have also been reported in patients with severe COVID-19. A transcriptome study of bronchoalveolar lavage fluid from patients with COVID-19 reported increased expression of numerous ISGs, in addition to markedly increased expres- sion of pro-inflammatory genes and chemokirie genes (Zhou et al, 2020). In a single-cell RNA sequencing study of peripheral blood mononuclear cells (PBMCs) from hospi- talized patients with COVID-19, various ISGs were upregu- lated in classical monocytes, although the ISG signature was heterogeneous among cell types and patients (Wilk et al., 2020). In agreement another study reported that severe COVID 19 patients highly inflammatory FCN1+ macro- phages express higher levels of type 1 interferon stimulated genes and multiple chemokines, including IP-10 leading to this being identified as the culprit for the deranged hyper- inflammation in those patients infected with SARS-CoV-2. (Liao et al 2020) IFN-I responses co-occurred with TNF- and IL-1-driven inflammatory responses in classical mono- cytes from patients with severe COVID-19, but not with mild COVID-19 (Lee et al., 2020), which suggests that IFN-I might have an important role in exacerbating TNF- and IL-1-driven inflammation in the progression to severe COVID-19 (Park et al., 2017). Interestingly, severe COVID- 19-specific gene signatures, including various ISGs identi- fied in this study, were significantly enriched in the tran- scriptome of post-mortem lung tissue from patients with COVID-19 published in the earlier study by Blanco-Melo et al. 2020, which supports the idea that IFN-I responses are upregulated in severe COVID-19. Furthermore, a recent longitudinal analysis of patients with moderate or severe COVID-19 corroborated these results by showing that IFNα in peripheral blood was sustained at high levels in patients with severe COVID-19 (Lucas et al., 2020). The severe pathological features of COVID-19 (Xu et al 2020) greatly resemble those seen in SARS-CoV and MERS-Cov infec- tion (Ding et al 2003, Ng et al 2016, Liu et al 2020) and an alternative therapy to IFN-α is required.

Over-production of antiviral Type I IFN's and the related IP-10 chemokine inhibit the appropriate immune response to clear secondary infections ((Nakamura et al, 2011; Shah- angian et al, 2009; Li et al, 2012) such as caused by bacterial agents such as *Streptococcus pneumonia, Moraxella catarrhalis*, and *Haemophilus influenzae* and even *Staphy- lococcus aureus* (Hewitt et al, 2016). These secondary infections cause excessive cell death within the lungs. In susceptible individuals, this leads to lung tissue injury and reduced lung function which causes serious complications and mortality in some cases.

Importantly, the pro-inflammatory activation occurs only to Type I IFN responses which cause the recruitment of neutrophils and inflammatory monocytes and macrophages and not to Type III IFN responses (Galani et al, 2017). However, Type III IFN's such as IFN lambda (IFN-1) can limit viral replication in epithelial cells without inducing pro-inflammatory responses or immunopathology (David- son et al, 2016; Galani et al, 2017, Dijkman et al 2018). Therefore, therapeutic agents that limit the Type I IFN responses and accompanying proinflammatory and tissue damaging response to viral infection, while maintaining Type III IFN's responses are desirable. More recently it has been reported that IFN lambda inhibits SARS-CoV-2 repli- cation in cell culture (primary human bronchial epithelial cells, primary human airway epithelial cultures, and primary human intestinal epithelial cells and mouse models (Busna- diego et al, 2020; Dinnon et al, 2020; Vanderheiden et al, 2020; Stanifer et al, 2020). Type III interferons have been proposed as a therapeutic modality for SARS-CoV-2 infec- tion, (Galani et al 2021; Felgenhauer et al., 2020) Pegylated interferon lambda accelerated viral decline in outpatients with COVID-19, increasing the proportion of patients with viral clearance by day 7, particularly in those with high baseline viral load. Pegylated interferon lambda has poten- tial to prevent clinical deterioration and shorten duration of viral shedding (Feld et al 2020).

Type III responses and anti-viral defence would be a significant advancement in the management of respiratory viral infections. This reduction of immunopathology is criti- cal for host survival and resolution of SARS and MERS related diseases. Another risk factor for severe respiratory viral pneumonia are interferon-induced transmembrane pro- tein-3 (IFITM3) single nucleotide polymorphism (SNP) such as IFITM3-rs12252-C/C was linked to severe influenza such as 2009-pHIN16 and severe/fatal avian H7N9 disease. These snp have been detected in some of the patients who tested positive for SAR-Cov-2. (Thevarajan et al, 2020). Three distinct mutations in IFITM1 or IFITM3 converted the host restriction factors to enhance entry driven by the spike proteins of (SARS-CoV) and/or Middle East (MERS- CoV) (Zhao et al, 2018). IFITM3 is not induced by type III lambda but is produced by type 1 and type II interferons instead.

Other innate sensors or immune mediators can also play an important role in early anti-viral defence Lung surfactant protein D (SP-D) can selectively recognized SARS corona- virus spike glycoprotein and enhances phagocytosis (Leth- Larsen et al 2007). Again, therapeutic agents that can induce this innate sensor which can bind to the virus to aid phagocytosis and stop it from infecting: the bronchial epi- thelial cells would be a significant advancement in the treatment of SARS-Cov or MERS-CoV infections.

More recently a recombinant fragment of human SP-D has recently been shown to neutralize SARS-CoV-2 (Watson et al., 2021). A study by Kerget et al., (2020) found SP-D to be higher in COVID-19 patients compared to the control group and levels were strongly associated with ARDS development. These studies confirm the potential of SP-D as a biomarker and treatment strategy for COVID-19 patients.

The invention provides therapeutic agents which can induce Type III IFN-α and/or SP-D and have a role to play in early clearance of the primary viral infection while reducing the likelihood of secondary bacterial infections and would be a significant advancement in the management of ARDS caused by pathogenic Cov. and its newer variant SARS-CoV-2.

Example 27—Chewable Tablet

A chewable tablet was prepared.

| Ingredient | Mg/tablet |
|---|---|
| *Bif Longum* Strain 106 | 7 |
| Cellulose Microcrystalline | 57.8 |
| Isomalt | 525.99 |
| Sucralose | 0.4 |
| Banana flavour | 0.9 |
| Strawberry flavour | 0.9 |
| Vitamin D | 0.01 |
| Magnesium stearate | 7 |
| TOTAL | 600 |

The amount of *Bif longum* Strain 106 per single tablet dose is 1.87E+09

The amount of Vitamin D per single tablet dose is 200% NRV

Chewable tablets are manufactured by mixing/blending the raw ingredients together, followed by a compression process (including process controls) to form the tablet. The tablets are then packaged into bottles (such as High-Density Polyethylene (HDPE) bottles). The chewable tablet formulation ensures that the strain 106 and Vitamin D is released in the mouth/throat. The tablet is preferably held in the mouth until it dissolves giving an increased residence time for the strain in the mouth.

*Bifidobacterium longum* strain NCIMB 42020 induced more IL-10, IL-12p40, TNF-α, IL-1β in both PBMCs and MDDCs than other strains of *Bifidobacterium longum* strains which gave similar profiles to each other. *Bifidobacterium longum* strain NCIMB 42020 is a much more potent stimulator of cytokines than the other *B. longum* especially known anti-inflammatory strains and engages with the human immune system in a different way to the other *B. longum* strains in a manner which is more immunostimulatory. *Bifidobacterium longum* strain NCIMB 42020 beneficially blocks Type 1 interferons and resultant IP-10 induction (a pro-inflammatory chemokine) and increase Type 3 interferon IFN-λ in monocyte derived dendritic cells. *Bifidobacterium longum* strain NCIMB 42020 beneficially blocks TNF-α as well as IP-10 in monocyte derived dendritic cells but not all Bifidobacteria *longum* strains have the same effect.

The efficacy of Bifidobacterium *longum* strain NCIMB 42020 was tested in pre-clinical models designed to show therapeutic benefit. Surprisingly, administration of the *B. longum* AH0106 protected the mice better than the *B. longum* 35624 strain. Viral titre was reduced by similar levels in both strains, but mortality was reduced more in the *B. longum* AH0106 treated mice. This enhanced survival was associated with a reduced interferon-alpha and interferon-beta response and an enhanced surfactant protein D response. In addition, there was a potent induction of cytokines and chemokines in animals treated with *Bifidobacterium longum* strain NCIMB 42020 associated with the increase in macrophages in the BAL at day 5. This immune response contributed to the enhanced viral clearance seen in the animals treated with *Bifidobacterium longum* strain NCIMB 42020 and the start of the healing process brought the influx of macrophages into the lung.

Vitamin D has been recognised by the European food safety authority (EFSA) for its role in the normal function of the immune system (EFSA Panel on Dietetic Products, Nutrition and Allergies (NDA), 2010. Scientific Opinion on the substantiation of health claims related to vitamin D and normal function of the immune system and inflammatory response (ID 154, 159), maintenance of normal muscle function (ID 155) and maintenance of normal cardiovascular function (ID 159) pursuant to Article 13 (1) of Regulation (EC) No 1924/2006. EFSA Journal, 8(2), p. 1468).

Vitamin D has been found to be a modulator of both the adaptive and innate immune system. Immune cells can express certain vitamin D-activating enzymes, which convert inactive vitamin-D to its active form within the immune system. Vitamin D also plays a role in the innate immune system, enhancing the immune and antimicrobial functions of monocytes and macrophages. (Baeke, F., Takiishi, T., Korf, H., Gysemans, C. and Mathieu, C., 2010. Vitamin D: modulator of the immune system. Current opinion in pharmacology, 10(4), pp. 482-496).

This activated vitamin D can then be recognised by vitamin D-receptors which have been identified in a range of immune cells (Takahashi, K., Nakayama, Y., Horiuchi, H., Ohta, T., Komoriya, K., Ohmori, H. and Kamimura, T., 2002. Human neutrophils express messenger RNA of vitamin D receptor and respond to 1 α, 25-dihydroxyvitamin D3. Immunopharmacology and immunotoxicology, 24(3), pp. 335-347.) Vitamin D has been shown to modulate T-cell adaptive immunity, influencing the levels of both pro- and anti-inflammatory cytokines (Zdrenghea, M. T., Makrinioti, H., Bagacean, C., Bush, A., Johnston, S. L. and Stanciu, L. A., 2017. Vitamin D modulation of innate immune responses to respiratory viral infections. Reviews in medical virology, 27(1), p. e1909).

Nutrient Reference Values (NRVs) were set in the EU Food Information for Consumers Regulation 1169/2011. The NRV for vitamin D is 5 μg (0.005 mg), which is equivalent to 100%. The chewable tablet in example 1 contains 10 μg (0.01 mg), which is equivalent to 200% NRV. NRV's are set as EU guidance levels on the daily amount of vitamin or mineral that the average healthy person needs to prevent deficiency. In 2016, the EFSA NDA Panel set an adequate intake for vitamin D at 15 g/day for adults. This was based on an adjusted model of meta-regression analysis on data collected under conditions of assumed minimal cutaneous vitamin D synthesis. In 2019, the European Calcified Tissue Society (ECTS) recommended a vitamin D supplement of 10 g/day for all children of 0-1 year, a vitamin D supplement of 10-15 μg/day for all pregnant women and a vitamin D supplement of 10-20 g/day for all older institutionalized subjects, also to be considered for all older persons above 70 years. This recommendation was based on the levels of serum 25-hydroxyvitamin D (25(OH)D) in different populations and in risk groups for vitamin D deficiency. Therefore, the quantity of vitamin D in the formulation provides an adequate amount of the vitamin, as outlined above.

Microcrystalline cellulose is a tableting excipient used for the binding of raw ingredients in the manufacture tablets using a compression process. Magnesium stearate is an anti-caking agent.

Sucralose is an artificial zero calorie sweetener, which is used as a substitute for sugar and contributes to the sweetness. Isomalt is a sugar substitute which has desired compressibility and mouthfeel for a chewable tablet. Isomalt is a sugar alcohol (polyol) used for its physical properties, with the ability to withstand heat (non-reducing) and blends easily with other sweeteners to achieve the desired sweetness profile.

In a recent study, sixty-five consecutive COVID-19 patients (mean age 76±13 years) and sixty-five sex- and age-matched control subjects were analyzed. 250H-vitamin D serum deficiency was found to be associated with more severe lung involvement, longer disease duration and risk of death; in elderly COVID-19 patients. The detection of low vitamin D levels also in younger COVID-19 patients with less comorbidities also suggests that vitamin D deficiency is a crucial risk factor at any age (Sulli et al., 2021).

Older adults with vitamin D deficiency and COVID-19 may demonstrate worse morbidity outcomes (Baktash et al., 2020).

COVID19 patients with poor prognosis have been found to have significantly lower serum levels of vitamin D compared with those with good prognosis (Munshi et al., 2020).

It will be appreciated that the strains of the invention may be administered to animals (including humans) in an orally ingestible form in a conventional preparation such as capsules, microcapsules, tablets, granules, powder, troches, pills, suppositories, suspensions and syrups. Suitable formulations may be prepared by methods commonly employed using conventional organic and inorganic additives. The amount of active ingredient in the medical composition may be at a level that will exercise the desired therapeutic effect.

The formulation may also include a bacterial component, a drug entity or a biological compound.

In addition, a vaccine comprising the strains of the invention may be prepared using any suitable known method and may include a pharmaceutically acceptable carrier or adjuvant.

The human immune system plays a significant role in the aetiology and pathology of a vast range of human diseases. Hyper and hypo-immune responsiveness results in, or is a component of, the majority of disease states. One family of biological entities, termed cytokines, are particularly important to the control of immune processes. Perturbances of these delicate cytokine networks are being increasingly associated with many diseases. These diseases include but are not limited to inflammatory disorders, immunodeficiency, inflammatory bowel disease, irritable bowel syndrome, cancer (particularly those of the gastrointestinal and immune systems), diarrhoeal disease, antibiotic associated diarrhoea, paediatric diarrhoea, appendicitis, autoimmune disorders, multiple sclerosis, Alzheimer's disease, rheumatoid arthritis, coeliac disease, diabetes mellitus, organ transplantation, bacterial infections, viral infections, fungal infections, periodontal disease, urogenital disease, sexually transmitted disease, HIV infection, HIV replication, HIV associated diarrhoea, surgical associated trauma, surgical-induced metastatic disease, sepsis, weight loss, anorexia, fever control, cachexia, wound healing, ulcers, gut barrier function, allergy, asthma, respiratory disorders, circulatory disorders, coronary heart disease, anaemia, disorders of the blood coagulation system, renal disease, disorders of the central nervous system, hepatic disease, ischaemia, nutritional disorders, osteoporosis, endocrine disorders, epidermal disorders, psoriasis and acne vulgaris. The effects on cytokine production are specific for the probiotic strain examined. Thus, specific probiotic strains may be selected for normalising an exclusive cytokine imbalance particular for a specific disease type.

The enteric flora is important to the development and proper function of the intestinal immune system. In the absence of an enteric flora, the intestinal immune system is underdeveloped, as demonstrated in germ free animal models, and certain functional parameters are diminished, such as macrophage phagocytic ability and immunoglobulin production. The importance of the gut flora in stimulating non-damaging immune responses is becoming more evident. The increase in incidence and severity of allergies in the western world has been linked with an increase in hygiene and sanitation, concomitant with a decrease in the number and range of infectious challenges encountered by the host. This lack of immune stimulation may allow the host to react to non-pathogenic, but antigenic, agents resulting in allergy or autoimmunity. Deliberate consumption of a series of non-pathogenic immunomodulatory bacteria would provide the host with the necessary and appropriate educational stimuli for proper development and control of immune function.

Inflammation is the term used to describe the local accumulation of fluid, plasma proteins and white blood cells at a site that has sustained physical damage, infection or where there is an ongoing immune response. Control of the inflammatory response is exerted on a number of levels. The controlling factors include cytokines, hormones (e.g. hydrocortisone), prostaglandins, reactive intermediates and leukotrienes. Cytokines are low molecular weight biologically active proteins that are involved in the generation and control of immunological and inflammatory responses, while also regulating development, tissue repair and haematopoiesis. They provide a means of communication between leukocytes themselves and also with other cell types. Most cytokines are pleiotropic and express multiple biologically overlapping activities. Cytokine cascades and networks control the inflammatory response rather than the action of a particular cytokine on a particular cell type. Waning of the inflammatory response results in lower concentrations of the appropriate activating signals and other inflammatory mediators leading to the cessation of the inflammatory response. TNFα is a pivotal pro-inflammatory cytokine as it initiates a cascade of cytokines and biological effects resulting in the inflammatory state. Therefore, agents which inhibit TNFα are currently being used for the treatment of inflammatory diseases, e.g. infliximab.

Pro-inflammatory cytokines are thought to play a major role in the pathogenesis of many inflammatory diseases, including inflammatory bowel disease (IBD). Current therapies for treating IBD are aimed at reducing the levels of these pro-inflammatory cytokines, including IL-8 and TNFα. Such therapies may also play a significant role in the treatment of systemic inflammatory diseases such as rheumatoid arthritis.

The strains of the present invention may have potential application in the treatment of a range of inflammatory diseases, particularly if used in combination with other anti-inflammatory therapies, such as non-steroid anti-inflammatory drugs (NSAIDs) or Infliximab.

The production of multifunctional cytokines across a wide spectrum of tumour types suggests that significant inflammatory responses are ongoing in patients with cancer. It is currently unclear what protective effect this response has against the growth and development of tumour cells in vivo. However, these inflammatory responses could adversely affect the tumour-bearing host. Complex cytokine interactions are involved in the regulation of cytokine production and cell proliferation within tumour and normal tissues. It has long been recognized that weight loss (cachexia) is the single most common cause of death in patients with cancer and initial malnutrition indicates a poor prognosis. For a tumour to grow and spread it must induce the formation of new blood vessels and degrade the extracellular matrix. The inflammatory response may have significant roles to play in the above mechanisms, thus contributing to the decline of the host and progression of the tumour. Due to the anti-inflammatory properties of *Bifidobacterium longum* these bacterial strains they may reduce the rate of malignant cell transformation. Furthermore, intestinal bacteria can produce, from dietary compounds, substances with genotoxic, carcinogenic and tumour-promoting activity and gut bacteria can activate pro-carcinogens to DNA reactive agents. In general, species of *Bifidobacterium* have low activities of xenobiotic metabolizing enzymes compared to other populations within the gut such as *bacteroides*, eubacteria and clostridia. Therefore, increasing the number of *Bifidobacterium* bacteria in the gut could beneficially modify the levels of these enzymes.

The majority of pathogenic organisms gain entry via mucosal surfaces. Efficient vaccination of these sites protects against invasion by a particular infectious agent. Oral vaccination strategies have concentrated, to date, on the use of attenuated live pathogenic organisms or purified encapsulated antigens. Probiotic bacteria, engineered to produce antigens from an infectious agent, in vivo, may provide an attractive alternative as these bacteria are considered to be safe for human consumption (GRAS status).

Murine studies have demonstrated that consumption of probiotic bacteria expressing foreign antigens can elicit protective immune responses. The gene encoding tetanus toxin fragment C (TTFC) was expressed in *Lactococcus lactis* and mice were immunized via the oral route. This system was able to induce antibody titers significantly high enough to protect the mice from lethal toxin challenge. In addition to antigen presentation, live bacterial vectors can produce bioactive compounds, such as immunostimulatory cytokines, in vivo. *L. lactis* secreting bioactive human IL-2 or IL-6 and TTFC induced 10-15 fold higher serum IgG titres in mice immunized intranasally. However, with this particular bacterial strain, the total IgA level was not increased by co-expression with these cytokines. Other bacterial strains, such as *Streptococcus gordonii*, are also being examined for their usefulness as mucosal vaccines. Recombinant *S. gordonii* colonizing the murine oral and vaginal cavities induced both mucosal and systemic antibody responses to antigens expressed by this bacterial. Thus, oral immunization using probiotic bacteria as vectors would not only protect the host from infection but may replace the immunological stimuli that the pathogen would normally elicit thus contributing to the immunological education of the host.

Prebiotics

The introduction of probiotic organisms is accomplished by the ingestion of the micro-organism in a suitable carrier. It would be advantageous to provide a medium that would promote the growth of these probiotic strains in the large bowel. The addition of one or more oligosaccharides, polysaccharides, or other prebiotics enhances the growth of lactic acid bacteria in the gastrointestinal tract. Prebiotics refers to any non-viable food component that is specifically fermented in the colon by indigenous bacteria thought to be of positive value, e.g. bifidobacteria, lactobacilli. Types of prebiotics may include those that contain fructose, xylose, soya, galactose, glucose and mannose. The combined administration of a probiotic strain with one or more prebiotic compounds may enhance the growth of the administered probiotic in vivo resulting in a more pronounced health benefit and is termed synbiotic.

Other Active Ingredients

It will be appreciated that the probiotic strains may be administered prophylactically or as a method of treatment either on its own or with other probiotic and/or prebiotic materials as described above. In addition, the bacteria may be used as part of a prophylactic or treatment regime using other active materials such as those used for treating inflammation or other disorders especially those with an immunological involvement. Such combinations may be administered in a single formulation or as separate formulations administered at the same or different times and using the same or different routes of administration.

Pharmaceutical Compositions

A pharmaceutical composition is a composition that comprises or consists of a therapeutically effective amount of a pharmaceutically active agent. It preferably includes a pharmaceutically acceptable carrier, diluent or excipients (including combinations thereof). Acceptable carriers or diluents for therapeutic use are well known in the pharmaceutical art, and are described, for example, in Remington's Pharmaceutical Sciences. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s), propellants(s).

Examples of pharmaceutically acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like.

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in a mixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration, the compositions may be administered in the form of tablets or lozenges which can be formulated in a conventional manner.

The strains and/or cell wall fractions in some cases are administered to the mouth, larynx, nasal cavity and/or oropharynx and/or nasopharynx. In some cases the strains and/or cell wall fractions are not swallowed and in some cases are not substantially delivered to the gastrointestinal tract. The formulation may or may not be swallowed.

Intranasal administration can be accomplished using a nasal spray, nasal wash solution or direct application within the nose.

Administration to the lung could be in the form of a dry powder, inhaled using an inhaler device. In some cases the formulation is in the form of an aerosol. The aerosol may be a solution, suspension, spray, mist, vapour, droplets, particles, or a dry powder, for example, using a method dose inhaler including HFA propellant, a metered dose inhaler with non-HFA propellant, a nebulizer, a pressurized can, of a continuous sprayer.

The formulation may be designed to encapsulate, remove and/or inactivate a virus. The formulation alternatively or additionally may deter a virus from further infecting the respiratory tract.

To aid delivery to and maintenance in the respiratory tract such as in the nasal cavity, the formulation may have a desired viscosity of 1 centipoise to 2,000 centipoise, for example, 5 cps to 500 cps, or 5 cps to 300 cps. Any suitable viscosity modifying agent may be used to achieve the desired viscosity. Such agents may be suitable natural or synthetic polymeric materials such as hydroxypropyl methylcellulose.

There may be different composition/formulation requirements dependent on the different delivery systems. By way of example, the pharmaceutical composition of the present invention may be formulated to be delivered using a mini-pump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by both routes. The formulation may also be delivered by infusion.

The references mentioned in this specification are incorporated herein in their entirety.

The invention is not limited to the embodiment hereinbefore described, which may be varied in detail.

REFERENCES

Xu Z, Shi L, Wang Y, Zhang J, Huang L, Zhang C, Liu S, Zhao P, Liu H, Zhu L, Tai Y, Bai C, Gao T, Song J, Xia P, Dong J, Zhao J, Wang F S. Pathological findings of COVID-19 associated with acute respiratory distress syndrome Lancet Respir Med. 2020 Feb. 18. pii: S2213-2600 (20)30076-X.

Zhiqi Song, Yanfeng Xu, Linlin Bao, Ling Zhang, Pin Yu Yajin Qu, Hua Zhu Wenjie Zhao Yunlin Han and Chuan Qin*From SARS to MERS, Thrusting Coronaviruses into the Spotlight Viruses. 2019 January; 11(1): 59.

Scheuplein V A, Seifried J, Malczyk A H, Miller L, Höcker L, Vergara-Alert J, Dolnik O, Zielecki F, Becker B, Spreitzer I, König R, Becker S, Waibler Z, Mühlebach M D High secretion of interferons by human plasmacytoid dendritic cells upon recognition of Middle East respiratory syndrome coronavirus. J Virol. 2015 April; 89(7): 3859-69. doi: 10.1128/JVI.03607-14.

Channappanavar R, Fehr A R, Vijay R, Mack M, Zhao J, Meyerholz D K, Perlman S. Dysregulated Type I Interferon and Inflammatory Monocyte-Macrophage Responses Cause Lethal Pneumonia in SARS-CoV-Infected Mice.

Cell Host Microbe. 2016 Feb. 10; 19(2):181-93. Channappanavar R Fehr A R, Zheng J, Wohlford-Lenane C, Abrahante J E, Mack M, Sompallae R, McCray P B Jr, Meyerholz D K, Perlman S J Clin Invest. 2019 Jul. 29; 130:3625-3639 IFN-I response timing relative to virus replication determines MERS coronavirus infection outcomes.

Ding Y, Wang H, Shen H, et al. The clinical pathology of severe acute respiratory syndrome (SARS): a report from China. J Pathol 2003; 200: 282-89.

Ng D L, Al Hosani F, Keating M K, et al. Clinicopathologic, immunohistochemical, and ultrastructural findings of a fatal case of Middle East respiratory syndrome coronavirus infection in the United Arab Emirates, April 2014. Am J Pathol 2016; 186: 652-58.

Ronald Dijkman*, Rudragouda Channappanavar*, . . . Stanley Perlman and Volker Thiel (2018). Protective role of interferon lambda during MERS-CoV infection (manuscript in preparation).

Irani Thevarajan, Thi H O Nguyen, Marios Koutsakos, Julian Druce, Leon Caly, Carolien E van de Sandt, Xiaoxiao Jia, Suellen Nicholson, Mike Catton, Benjamin Cowie, View ORCID ProfileSteven Tong, Sharon Lewin, View ORCID ProfileKatherine Kedzierska Breadth of concomitant immune responses underpinning viral clearance and patient recovery in a non-severe case of COVID-19 MedRxiv Zhao X, Sehgal M, Hou Z, Cheng J, Shu S, Wu S, Guo F, Le Marchand S J, Lin H, Chang J, Guo J T. Identification of Residues Controlling Restriction versus Enhancing Activities of IFITM Proteins on Entry of Human Coronaviruses. J Virol. 2018 Feb. 26; 92(6). pii: e01535-17. doi: 10.1128/JVI.01535-17. Print 2018 Mar. 15.

Leth-Larsen R, Zhong F, Chow V T, Holmskov U, Lu J. The SARS coronavirus spike glycoprotein is selectively recognized by lung surfactant protein D and activates macrophages. Immunobiology. 2007; 212(3):201-11. Epub 2007 Jan. 26.

Xu K, Cai H, Shen Y, Ni Q, Chen Y, Hu S, Li J, Wang H, Yu L, Huang H, Qiu Y, Wei G, Fang Q, Zhou J, Sheng J, Liang T, Li L. [Management of corona virus disease-19 (COVID-19): the Zhejiang experience]. [Article in Chinese]Zhejiang Da Xue Xue Bao Yi Xue Ban. 2020 Feb. 21; 49(1):0.

Channappanavar, R. and Perlman, S. (2017) Pathogenic human coronavirus infections: causes and consequences of cytokine storm and immunopathology. Semin Immunopathol 39, 529-539.

Minfeng Liao, Yang Liu, Jin Yuan, Yanling Wen, Gang Xu, Juanjuan Zhao, Lin Chen, Jinxiu Li, Xin Wang, Fuxiang Wang, Lei Liu, Shuye Zhang, Zheng Zhang The landscape of lung bronchoalveolar immune cells in COVID-19 revealed by single-cell RNA sequencing MedRXIV February 2020

Liu J, Zheng X, Tong Q, Li W, Wang B, Sutter K, Trilling M, Lu M, Dittmer U Yang D. Overlapping and discrete aspects of the pathology and pathogenesis of the emerging human pathogenic coronaviruses SARS-CoV, MERS-CoV, and 2019-nCoV. J Med Virol. 2020 Feb. 13.

Bouhnik, Y., Survie et effets chez l'homme des bactéries ingérées dans les laits fermentés. Lait 1993, 73; 241-247.

O'Mahoiy L., McCarthy J., Kelly P., Hurley G., Luo F., Chen K., O'Sullilvan G C., Kiely B., Collins J K., Shanahan F., Quigley E M. Lactobacillus and Bifidobacterium in irritable bowel syndrome: symptom responses and relationship to cytokine profiles. Gastroenterology. 2005 March; 128(3):541-51.

O'Mahony C. et al., PLoS Pathogens 2008.

Konieczna P., Groeger D., Ziegler M., Frei R., Ferstl R., Shanahan F., Quigley E M., Kiely B., Akdis C A., O'Mahony L. Bifidobacterium infantis 35624 administration includes Foxp3 T regulatory cells in human peripherial blood: potential role for myeloid and plasmacytoid dendritic cells. Gut. 2012 March; 61(3):354-66. doi: 10.1136/gutjnl-2011-300936.

Groeger D., O'Mahony L., Murphy E F., Bourke J F., Dinan T G., Kiely B., Shanahan F., Quigley E M. *Bifidobacterium* infantis 35624 modulates host inflammatory processes beyond the gut. Gut Microbes. 2013 July-August; 4(4):325-39. doi: 10.4161/gmic.25487

Bartlett N W l., Singanayagam A., Johnston S L. Mouse models of rhinovirus infection and airways disease. Methods Mol Biol. 2015; 1221:181-8. doi: 10.1007/978-1-4939-1571-2_14.

Ivashkiv L B., and Donlin L T. Regulation of type I interferon responses. Nat Rev Immunol. 2014 January; 14(1): 36-49.

Lazear H M., Nice T J., Diamond M S. Interferon-□□□Immune Functions at Barrier Surfaces and Beyond. Immunity, 2015 Jul. 21; 43(1): 15-28.

Wack A., Terczynska-Fyla E., Hartmann R. Guarding the frontiers: the biology of the type III interferons. Nat Immunol. 2015 August; 16(8): 802-9.

Durbin R K., Kotenko S V., Durbin J E. Interferon induction and function at the muscol surface. Immunol Rev. 2013 September; 255(1): 25-39.

Mendoza J L., Schneider W M., Hoffmann H H., Vercauteren K., Jude K M., Xiong A., Moraga I., Horton T M., Glenn J S., de Jong Y P., Rice C M., Garcia K C. The IFN-□-IFN-□R1-IL-10Rβ Complex Reveals Structural Features Underlying Type III IFN Functional Plasticity. Immunity. 2017 Mar. 21; 46(3): 379-392.

Ichikawa A., Kuba K., Morita M., Chida S., Tezuka H., Hara H., Sasaki T., Ohteki T., Ranieri V M., dos Santos C C., Kawaoka Y., Akira S., Luster A D., Lu B., Penninger J M., Uhlig S., Slutsky A S., Imai Y. CXCL10-CXCR3 enhances the development of neutrophil-mediated fulminant lung injury of viral and nonviral origin. Am J Respir Crit Care Med. 2013 Jan. 1; 187(1):65-77.

Wei Wang, Penghui Yang, et al. Monoclonal antibody against CXCL-10/IP-10 ameliorates influenza A (H1N1) virus induced acute lung injury. Cell Research (2013) 23:577-580.

Hartshorn K L., White M R., Shepherd V., Reid K., Jensenius J C., Crouch E C. Mechanisms of anti-influenza activity of surfactant proteins A and D: comparison with serum collectins. Am J Physiol 1997; 273: L1156-L1166.

Reading P C., Morey L S., Crouch E C., Anders E M. Collectin-mediated antiviral host defense of the lung: evidence from influenza virus infection of mice. J Virol 1997; 71: 8204-8212.

Hartshorn K L., White M R., Voelker D R., Coburn J., Zaner K., Crouch E C. Mechanism of binding of surfactant protein D to influenza A viruses: importance of binding to haemagglutinin to antiviral activity. Biochem J 2000; 351 (Pt 2): 449-458.

Tecle T., White M R., Crouch E C., Hartshorn K L. Inhibition of influenza viral neuraminidase activity by collectins. Arch Virol 2007; 152: 1731-1742.

LeVine A M., Whitsett J A., Hartshorn K L., Crouch E C., Korfhagen T R. SP-D enhances clearance of influenza A virus from the lung in in vivo mouse models. J Immunol 2001; 167:5868-5873.

Vigerust D J., Ulett K B., Boyd K L., Madsen J., Hawgood S., McCullers J A. N-linked glycosylation attenuates H3N2 influenza viruses. J Virol 2007; 81:8593-8600.

Hawgood S., Brown C., Edmondson J., Stumbaugh A., Allen L., Goerke J. et al. Pulmonary collectins modulate strain-specific influenza a virus infection and host responses. J Virol 2004; 78: 8565-8572.

LeVine A M(1)., Elliott J., Whitsett J A., Srikiatkhachorn A., Crouch E., DeSilva N., Korfhagen T. Surfactant protein-d enhances phagocytosis and pulmonary clearance of respiratory syncytial virus. Am J Respir Cell Mol Biol. 2004 August; 31(2):193-9.

Rich H., Robinson K E., McHugh K J., Clay M E., Alcorn J F. The role of interferon lambda during influenza, *Staphylococcus aureus* super-infection. J Immunol May 1, 2017, 198(1 Supplement) 77.16.

Jounblat R., Clark H., Eggleton P., Hawgood S., Andrew P W., Kadioglu A. The role of surfactant protein D in the colonisation of the respiratory tract and onset of bacteraemia during pneumococcal pneumonia Respir Res. 2005 Oct. 28; 6:126.

World Health Organisation 2007. Global surveillance, prevention and control of chronic respiratory diseases, a comprehensive approach. (Editors Jean Bousquet and Nikolai Khaltaev).

Jartti T., Gern J E. Role of viral infections in the development and exacerbation of asthma in children. J Allergy Clin Immunol. 2017 October; 140(4):895-906.

Almond M H 1., Edwards M R., Barclay W S., Johnston S L. Obesity and susceptibility to severe outcomes following respiratory viral infection. Thorax. 2013 July; 68(7): 684-6. doi: 10.1136/thoraxjnl-2012-203009.

Steinke J W., Borish L. Immune Responses in Rhinovirus-Induced Asthma Exacerbations. Curr Allergy Asthma Rep. 2016 November; 16(11):78.

Zhou X., Li Q., Zhou X. Exacerbation of Chronic Obstructive Pulmonary Disease. Cell Biochem Biophys. 2015 November; 73(2):349-55.

Sulli A, Gotelli E, Casabella A, Paolino S, Pizzomi C, Alessandri E, Grosso M, Ferone D, Smith V, Cutolo M. Vitamin D and Lung Outcomes in Elderly COVID-19 Patients. Nutrients. 2021 Feb. 24; 13(3):717. doi: 10.3390/nu13030717.

Baktash V, Hosack T, Patel N, Shah S, Kandiah P, Van den Abbeele K, Mandal A K J, Missouris C G. Vitamin D status and outcomes for hospitalised older patients with COVID-19. Postgrad Med J. 2020 Aug. 27:postgradmedj-2020-138712. doi: 10.1136/postgradmedj-2020-138712.

Munshi R, Hussein M H, Toraih E A, Elshazli R M, Jardak C, Sultana N, Youssef M R, Omar M, Attia A S, Fawzy M S, Killackey M, Kandil E, Duchesne J. Vitamin D insufficiency as a potential culprit in critical COVID-19 patients. J Med Virol. 2021 February; 93(2):733-740. doi: 10.1002/jmv.26360.

Blanco-Melo, D. et al. Imbalanced host response to SARS-CoV-2 drives development of COVID-19. Cell 181, 1036-1045 (2020).

Zhou, Z. et al. Heightened innate immune responses in the respiratory tract of COVID-19 patients. Cell Host Microbe 27, 883-890 (2020).

Wilk, A. J. et al. A single-cell atlas of the peripheral immune response in patients with severe COVID-19. Nat. Med. 26, 1070-1076 (2020).

Lee, J. S. et al. Immunophenotyping of COVID-19 and influenza highlights the role of type I interferons in development of severe COVID-19. Sci. Immunol. 5, eabd1554 (2020).

Lee, J. S. et al. Immunophenotyping of COVID-19 and influenza highlights the role of type I interferons in development of severe COVID-19. Sci. Immunol. 5, eabd1554 (2020).

Lucas, C. et al. Longitudinal analyses reveal immunological misfiring in severe COVID-19. Nature https://doi.org/10.1038/s41586-020-2588-y (2020).

Park, S. H. et al. Type I interferons and the cytokine TNF cooperatively reprogram the macrophage epigenome to promote inflammatory activation. Nat. Immunol. 18, 1104-1116 (2017).

Wang, N. et al. Retrospective multicenter cohort study shows early interferon therapy is associated with favor- Management of corona virus disease-19 (COVID-19): the Zhejiang experience. J. Nutr. 12; 1-7.

Watson A, Madsen J, Clark H W. SP-A and SP-D: Dual Functioning Immune Molecules With Antiviral and Immunomodulatory Properties. Front Immunol. 2021 Jan. 19; 11:622598. doi: 10.3389/fimmu.2020.622598.

```
                      SEQUENCE LISTING

<160> NUMBER OF SEQ ID NOS: 2

<210> SEQ ID NO 1
<211> LENGTH: 20
<212> TYPE: DNA
<213> ORGANISM: Bifidobacterium longum

<400> SEQUENCE: 1
ggactgcagc gtagacgctt                                          20

<210> SEQ ID NO 2
<211> LENGTH: 21
<212> TYPE: DNA
<213> ORGANISM: Bifidobacterium longum

<400> SEQUENCE: 2
catcctgtat atgaggccca t                                        21
``` able clinical responses in COVID-19 patients. Cell Host Microbe https://doi.org/10.1016/j.chom.2020.07.005 (2020).

Dinnon 3rd, K H Leist S R Schafer A et al. A mouse-adapted model of SARS-CoV-2 to test COVID-19 countermeasures. Nature. 2020; 586: 560-566

Vanderheiden A Ralfs P Chirkova T et al. Type I and type III interferons restrict SARS-CoV-2 infection of human airway epithelial cultures. J Virol. 2020; 94: e00985-e001020

J. J. Feld et al., Peginterferon lambda for the treatment of outpatients with COVID-19: a phase 2, placebo-controlled randomised trial. Lancet Respir Med, (2021).

I. Busnadiego et al., Antiviral Activity of Type I, II, and III Interferons Counterbalances ACE2 Inducibility and Restricts SARS-CoV-2. mBio 11, (2020).

A. Vanderheiden et al., Type I and Type III Interferons Restrict SARS-CoV-2 Infection of Human Airway Epithelial Cultures. J Virol 94, (2020).

M. L. Stanifer et al., Critical Role of Type III Interferon in Controlling SARS-CoV-2 Infection in Human Intestinal Epithelial Cells. Cell Rep 32, 107863 (2020).

I. E. Galani et al., Untuned antiviral immunity in COVID-19 revealed by temporal type I/III interferon patterns and flu comparison. Nat Immunol 22, 32-40 (2021).

U. Felgenhauer et al., Inhibition of SARS-CoV-2 by type I and type III interferons. J Biol Chem 295, 13958-13964 (2020).

T. R. O'Brien et al., Weak Induction of Interferon Expression by Severe Acute Respiratory Syndrome Coronavirus 2 Supports Clinical Trials of Interferon-lambda to Treat Early Coronavirus Disease 2019. Clin Infect Dis 71, 1410-1412 (2020).

Kerget B, Kerget F, Kogak A O, et al. Are Serum Interleukin 6 and Surfactant Protein D Levels Associated with the Clinical Course of COVID-19?. Lung. 2020; 198(5):777-784. doi:10.1007/s00408-020-00393-8

The invention claimed is:

1. A method for the treatment of a coronavirus infection in a subject, the method comprising administering to the subject in need thereof a formulation comprising at least one *Bifidobacterium longum* strain or a cell wall fraction isolated from a *Bifidobacterium longum* strain, wherein the coronavirus infection is a SARS-CoV-2 infection, wherein a genome of the at least one *Bifidobacterium longum* strain is not manipulated to produce acquisition or loss of a gene, and wherein the at least one *Bifidobacterium longum* strain is selected from one or more of the strain having the accession number NCIMB 41003, the strain having the accession number NCIMB 41715, the strain having the accession number NCIMB 41713, or the strain having the accession number NCIMB 42020.

2. A method of claim 1, wherein the coronavirus infection is caused by a coronavirus that is SARS-CoV-2, and wherein the *Bifidobacterium longum* or cell wall fraction attenuates a IP-10 response to the coronavirus, enhances a type III interferon response to the coronavirus, enhances a interferon lambda response to the coronavirus, suppresses a interferon type I response to the coronavirus, suppresses a interferon alpha response to the coronavirus, suppresses a interferon beta response to the coronavirus, and/or enhances a surfactant protein D response to the coronavirus.

3. A method of claim 1, wherein the subject has been diagnosed with an inflammatory lung disease, is an acute respiratory distress syndrome (ARDS) patient, is an asthma patient, is obese, is a chronic obstructive pulmonary disease (COPD) patient, and/or is an elderly person greater than 60 years of age.

4. A method of claim 1, wherein the formulation further comprises Vitamin D.

5. A method of claim 1, wherein the formulation is in the form of a chewable or dissolvable tablet, a nasal spray, or a spray for spraying orally into a nasopharynx region of the subject.

6. A method of claim 1, wherein the *Bifidobacterium longum* strain is in the form of viable cells, non-viable cells, or both viable cells and non-viable cells.

7. A method of claim 1, wherein the *Bifidobacterium longum* strain is in the form of a freeze-dried powder.

8. A method of claim 1, wherein the *Bifidobacterium longum* strain is present in an amount of more than $10^6$ cfu per gram of the formulation.

9. A method of claim 1, wherein the formulation further comprises Vitamin D, and the Vitamin D is present in an amount of at least 5 μg.

10. A method of claim 1, wherein the formulation further comprises an ingestible carrier.

11. A method of claim 1, wherein the formulation further comprises a probiotic material, a prebiotic material, or both a probiotic material and a prebiotic material.

12. A method of claim 4, wherein the formulation further comprises a protein, a peptide, a lipid, a carbohydrate, another vitamin, a mineral, a trace element, or a combination thereof.

* * * * *